US007868115B1

(12) United States Patent
McPhee

(10) Patent No.: US 7,868,115 B1
(45) Date of Patent: *Jan. 11, 2011

(54) FARNESENE INTERPOLYMER

(75) Inventor: Derek James McPhee, Fairfield, CA (US)

(73) Assignee: Amyris Biotechnologies, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/825,364

(22) Filed: Jun. 29, 2010

Related U.S. Application Data

(63) Continuation of application No. 12/694,120, filed on Jan. 26, 2010, now Pat. No. 7,759,444, which is a continuation of application No. 12/507,801, filed on Jul. 23, 2009, now Pat. No. 7,655,739.

(60) Provisional application No. 61/220,591, filed on Jun. 26, 2009.

(51) Int. Cl.
   C08F 236/22   (2006.01)
   C08F 36/00    (2006.01)
   C08F 36/22    (2006.01)

(52) U.S. Cl. .................... 526/340.3; 526/335; 526/336; 526/339; 526/340; 525/331.9; 525/332.1; 525/332.8; 525/332.9; 525/333.1; 522/159

(58) Field of Classification Search ................................. C08F 36/22, 36/08, 236/22
See application file for complete search history.

(56) References Cited

U.S. PATENT DOCUMENTS

| 5,209,971 | A  |   | 5/1993  | Babu et al.           |
|-----------|----|---|---------|-----------------------|
| 5,698,751 | A  | * | 12/1997 | Ishida et al. ............ 585/16 |
| 7,655,739 | B1 | * | 2/2010  | McPhee et al. .......... 526/72 |
| 7,759,444 | B1 | * | 7/2010  | McPhee .................. 526/335 |
| 2010/0056714 | A1 | * | 3/2010 | McPhee .................. 524/579 |

FOREIGN PATENT DOCUMENTS

EP    0007758    2/1980

OTHER PUBLICATIONS

Monakov et al., The Reactivity of Isoprene and Its Copolymerization with Straight-chain Tetraene, Prom.-et. Sint. Kauch., 1979, 4; Chem. Abstr. 1979, 91, 176428p.
Newmark et al., 13C-NMR Spectra of cis-Polymyrcene and cis-Polyfarnesene, J. of Polymer Sci.: Part A: Polymer Chemistry, 1988, vol. 26, p. 71-77.

* cited by examiner

*Primary Examiner*—Callie E Shosho
*Assistant Examiner*—Frank D Ducheneaux
(74) *Attorney, Agent, or Firm*—Jones Day

(57) ABSTRACT

Provided herein are farnesene interpolymers derived from a farnesene and at least one vinyl monomer. In certain embodiments, the farnesene is α-farnesene, β-farnesene or a combination thereof. In some embodiments, the at least one vinyl monomer is ethylene, an α-olefin such as styrene, or a substituted or unsubstituted vinyl halide, vinyl ether, acrylonitrile, acrylic ester, methacrylic ester, acrylamide or methacrylamide, or a combination thereof.

20 Claims, 40 Drawing Sheets

FARNESENE INTERPOLYMER

CROSS-REFERENCE TO RELATED APPLICATIONS

This application is a continuation application of U.S. application Ser. No. 12/694,120, filed Jan. 26, 2010, now U.S. Pat. No. 7,759,444, which is a continuation application of U.S. application Ser. No. 12/507,801, now U.S. Pat. No. 7,655,739, filed Jul. 23, 2009, which claims the benefit of U.S. Provisional Patent Application Ser. No. 61/220,591, filed Jun. 26, 2009, each of which is incorporated herein by reference in its entirety.

FIELD OF THE INVENTION

This invention provides a farnesene interpolymer derived from a farnesene and at least a vinyl monomer. This invention also provides a farnesene interpolymer derived from a farnesene and at least one vinyl monomer wherein the mole percent ratio of the farnesene to the at least one vinyl monomer is from about 1:4 to about 100:1.

BACKGROUND OF THE INVENTION

An adhesive is a substance capable of holding materials (e.g., adherends or substrates) together by surface attachment. Pressure sensitive adhesives (PSAs) generally are adhesive materials which bond to adherends when a required pressure is applied to effect an adhesion to the adherends. PSAs can be permanent or removable. Removable PSAs have been widely used in re-positionable applications, such as Post-it® notes. Pressure sensitive adhesives are generally based on a polymer, a tackifier and an oil. Some common PSAs are based on polymers such as natural rubbers, synthetic rubbers (e.g., styrene-butadiene rubber and styrene-isoprene-styrene copolymer), polyacrylates, polymethacrylates, and poly-alpha-olefins.

Hot-melt adhesives at ambient temperature are generally solid materials that can be heated to a melt to hold adherends or substrates together upon cooling and solidifying. In some applications, the bonded substrates can be detached by remelting the hot melt adhesive if the substrates can withstand the heat. The hot melt adhesives are generally used in paper products, packaging materials, laminated wood panels, kitchen countertops, vehicles, tapes, labels, and a variety of disposable goods such as disposable diapers, hospital pads, feminine sanitary napkins, and surgical drapes. Generally, these hot melt adhesives are based on a polymer, tackifier, and a wax. Some common hot melt adhesives are based on semi-crystalline polymers such as ethylene homopolymers, ethylene copolymers and styrene block copolymers (e.g., styrene-isoprene-styrene copolymer or styrene-butadiene-styrene copolymer). One desirable property of hot melt adhesives is the absence of a liquid carrier, thereby eliminating a potential costly and hazardous process associated with solvent removal.

Polymers derived from terpenes or isoprenoid compounds are useful polymeric materials. For example, polyisoprene, polypinene and polylimonene have been used in various applications such as in the manufacture of paper coatings, rubber compounds, and other industrial products. However, adhesive compositions comprising polymers derived from terpenes or isoprenoid compounds are rare, even rarer are polymers derived from isoprenoid compounds having at least 15 carbon atoms.

Despite the availability of a variety of hot melt adhesives and pressure sensitive adhesives, there are still needs for new adhesive compositions having unique adhesive properties to meet new requirements. Further, there is a need for environmentally friendly or renewable polymers, for instance, polymers derived from isoprenoid compounds that can be obtained from natural sources.

SUMMARY OF THE INVENTION

The aforementioned needs are met by various aspects disclosed herein. In one aspect, provided herein is a composition comprising a polyfarnesene and a tackifier. In some embodiments, the composition disclosed herein is a hot melt adhesive composition. In other embodiments, the composition disclosed herein is a pressure sensitive adhesive composition.

In certain embodiments, the polyfarnesene has formula (X'):

(X')

wherein n is an integer from 1 to about 100,000; m is an integer from 0 to about 100,000; X is derived from a farnesene; and Y is derived from a vinyl monomer, with the proviso that when m is 1 or greater, the mole percent ratio of X to Y is from about 1:4 to about 100:1.

In some embodiments, X of the polyfarnesene disclosed herein has one or more of formulae (I')-(VIII') and stereoisomers thereof:

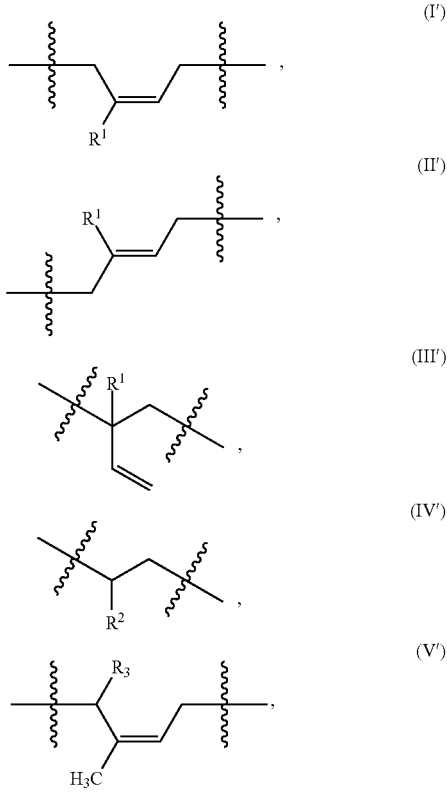

-continued

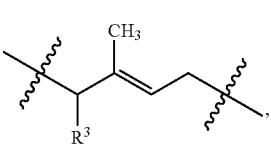
(VI')

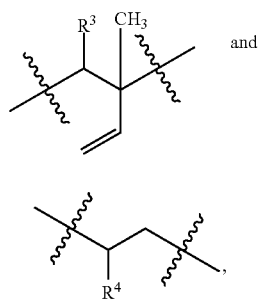
(VII')

and (VIII')

wherein R¹ has formula (XI):

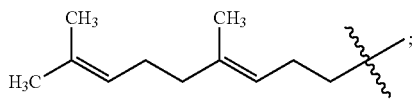
(XI)

R² has formula (XII):

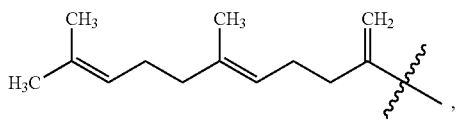
(XII)

R³ has formula (XIII):

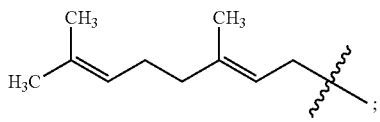
(XIII)

and

R⁴ has formula (XIV):

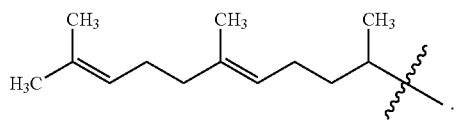
(XIV)

In certain embodiments, Y of the polyfarnesene disclosed herein has formula (IX') or a stereoisomer thereof:

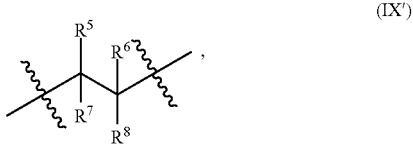
(IX')

wherein each of $R^5$, $R^6$, $R^7$ and $R^8$ is independently H, alkyl, cycloalkyl, aryl, alkenyl, cycloalkenyl, alkynyl, heterocyclyl, alkoxy, aryloxy, carboxy, alkoxycarbonyl, aminocarbonyl, alkylaminocarbonyl, dialkylaminocarbonyl, acyloxy, nitrile or halo.

In some embodiments, the amount of formula (I'), i.e., the cis-1,4-microstructure, in the polyfarnesene disclosed herein is at most about 80 wt. % and the amount of formula (II'), i.e., the trans-1,4-microstructure, in the polyfarnesene disclosed herein is from about 5 wt. % to about 99 wt. %, based on the total weight of the polyfarnesene.

In certain embodiments, the $M_w$ of the polyfarnesene is greater than about 60,000 daltons. In other embodiments, the $T_g$ of the polyfarnesene is less than about −60° C.

In some embodiments, the tackifier is present from about 5 wt. % to about 70 wt. %, based on the total weight of the composition. In other embodiments, the tackifier has a ring and ball (R&B) softening point equal to or greater than 80° C., as measured in accordance with ASTM 28-67.

In certain embodiments, the composition disclosed herein further comprises an additive selected from the group consisting of plasticizers, oils, waxes, antioxidants, UV stabilizers, colorants or pigments, fillers, flow aids, coupling agents, crosslinking agents, surfactants, solvents and combinations thereof.

In some embodiments, m is 0 and the polyfarnesene is a farnesene homopolymer. In other embodiments, the polyfarnesene disclosed herein is a random interpolymer. In further embodiments, m is from 1 to about 100,000 and the polyfarnesene is a random farnesene interpolymer. In certain embodiments, the polyfarnesene disclosed herein is a block interpolymer. In other embodiments, m is from 1 to about 100,000 and the polyfarnesene is a block farnesene interpolymer. In further embodiments, the polyfarnesene is a block interpolymer comprising one or more blocks of X and one or more blocks of Y. In some embodiments, the polyfarnesene is a block interpolymer comprising one block of X and two blocks of Y. In other embodiments, the polyfarnesene is a block interpolymer comprising one block of X and two blocks of Y wherein the X block is between the two Y blocks.

In certain embodiments, $R^5$ is aryl; and each of $R^6$, $R^7$ and $R^8$ is H. In other embodiments, $R^5$ is phenyl.

In some embodiments, the amount of formula (III') in the polyfarnesene disclosed herein is at least about 70 wt. %, based on the total weight of the polyfarnesene.

In certain embodiments, the polyfarnesene disclosed herein is obtained by polymerizing a farnesene (e.g., α-farnesene, β-farnesene or a combination thereof) in the presence of a catalyst. In other embodiments, the farnesene is β-farnesene.

In one aspect, provided herein is an adhesive composition comprising a polyfarnesene and a tackifier, wherein the polyfarnesene is prepared by polymerizing β-farnesene in the presence of a catalyst, wherein the amount of cis-1,4-microstructure in the polyfarnesene is at most about 80 wt. %, based on the total weight of the polyfarnesene.

In some embodiments, the β-farnesene is copolymerized with a vinyl monomer to form a farnesene interpolymer and wherein the mole percent ratio of the farnesene to the vinyl monomer is from about 1:4 to about 100:1.

In certain embodiments, the farnesene is copolymerized with a vinyl monomer to form a farnesene interpolymer. In other embodiments, the vinyl monomer is α-methylstyrene or divinylbenzene. In further embodiments, the vinyl monomer is styrene. In still further embodiments, the farnesene interpolymer is a block farnesene interpolymer.

In one aspect, provided herein is an article comprising a substrate partially or fully coated with the composition disclosed herein. In some embodiments, the article is a paper product, packaging material, laminated wood panel, kitchen countertop, vehicle, label, disposable diaper, hospital pad, feminine sanitary napkin, surgical drape, tape, case, carton, tray, medical device or bandage. In other embodiments, the article is a tape, case, carton, tray, medical device or bandage.

Additional aspects of the invention and characteristics and properties of various embodiments of the invention become apparent with the following description.

DETAILED DESCRIPTION OF THE INVENTION

General Definitions

Figure 1:
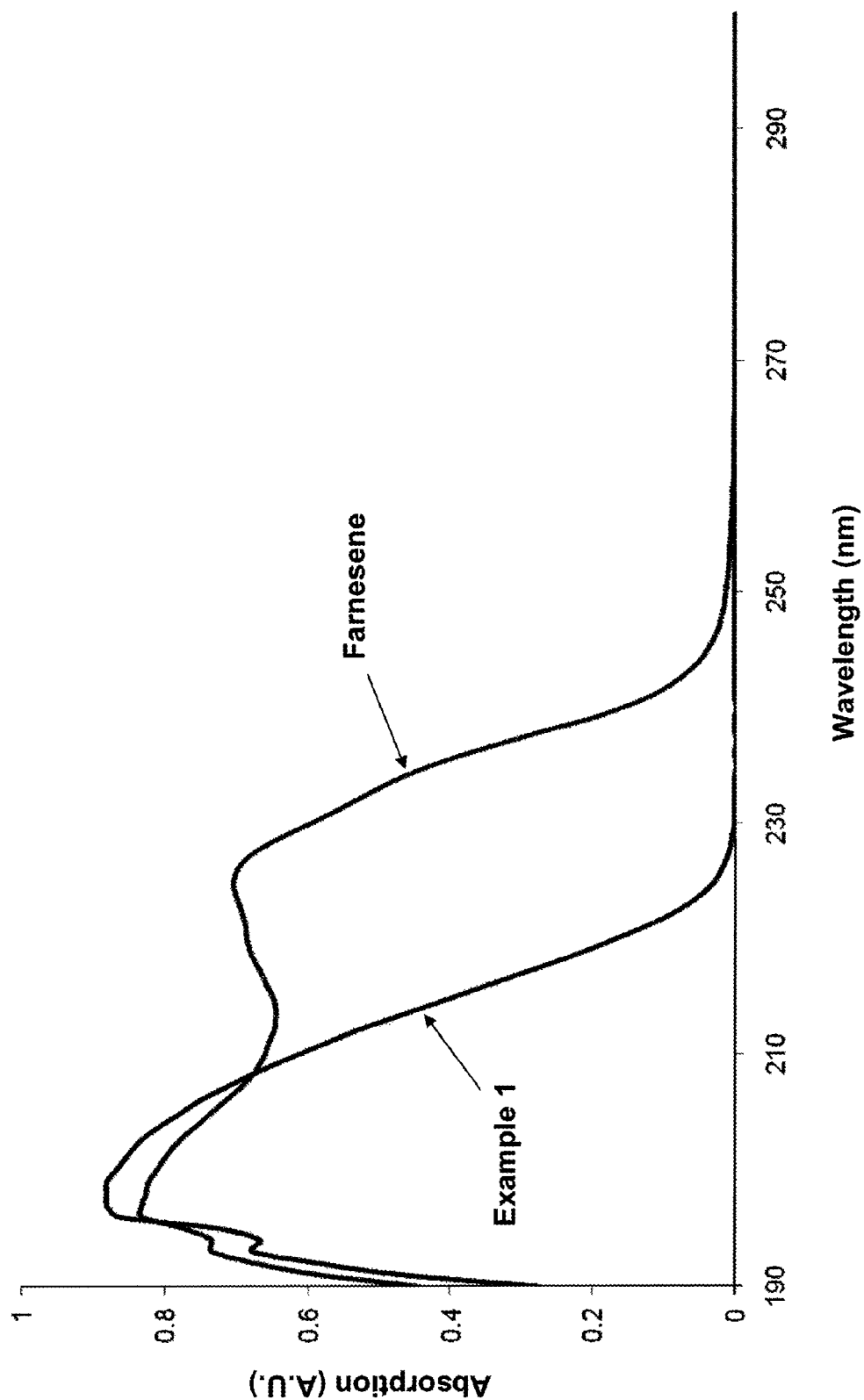
FIG. 1 depicts Ultraviolet-Visible (UV-Vis) spectra of Example 1 and β-farnesene.

"Polymer" refers to a polymeric compound prepared by polymerizing monomers, whether of the same or a different type. The generic term "polymer" embraces the terms "homopolymer," "copolymer," "terpolymer" as well as "interpolymer."

"Interpolymer" refers to a polymer prepared by the polymerization of at least two different types of monomers. The generic term "interpolymer" includes the term "copolymer" (which generally refers to a polymer prepared from two different monomers) as well as the term "terpolymer" (which generally refers to a polymer prepared from three different types of monomers). It also encompasses polymers made by polymerizing four or more types of monomers.

"Organyl" refers to any organic substituent group, regardless of functional type, having one free valence at a carbon atom, e.g., $CH_3CH_2$—, $ClCH_2$—, $CH_3C(=O)$—, 4-pyridylmethyl.

"Hydrocarbyl" refers to any univalent group formed by removing a hydrogen atom from a hydrocarbon, such as alkyl (e.g., ethyl), cycloalkyl (e.g., cyclohexyl) and aryl (e.g., phenyl).

"Heterocyclyl" refers to any univalent group formed by removing a hydrogen atom from any ring atom of a heterocyclic compound.

"Alkyl" or "alkyl group" refers to a univalent group having the general formula $C_nH_{2n+1}$ derived from removing a hydrogen atom from a saturated, unbranched or branched aliphatic hydrocarbon, where n is an integer, or an integer between 1 and 20, or between 1 and 8. Examples of alkyl groups include, but are not limited to, $(C_1-C_8)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl and octyl. Longer alkyl groups include nonyl and decyl groups. An alkyl group can be unsubstituted or substituted with one or more suitable substituents. Furthermore, the alkyl group can be branched or unbranched. In some embodiments, the alkyl group contains at least 2, 3, 4, 5, 6, 7, or 8 carbon atoms.

"Cycloalkyl" or "cycloalkyl group" refers to a univalent group derived from a cycloalkane by removal of a hydrogen atom from a non-aromatic, monocyclic or polycyclic ring comprising carbon and hydrogen atoms. Examples of cycloalkyl groups include, but are not limited to, $(C_3-C_7)$ cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Furthermore, the cycloalkyl group can be monocyclic or polycyclic. In some embodiments, the cycloalkyl group contains at least 5, 6, 7, 8, 9, or 10 carbon atoms.

"Aryl" or "aryl group" refers to an organic radical derived from a monocyclic or polycyclic aromatic hydrocarbon by removing a hydrogen atom. Non-limiting examples of the aryl group include phenyl, naphthyl, benzyl, or tolanyl group, sexiphenylene, phenanthrenyl, anthracenyl, coronenyl, and tolanylphenyl. An aryl group can be unsubstituted or substituted with one or more suitable substituents. Furthermore, the aryl group can be monocyclic or polycyclic. In some embodiments, the aryl group contains at least 6, 7, 8, 9, or 10 carbon atoms.

"Isoprenoid" and "isoprenoid compound" are used interchangeably herein and refer to a compound derivable from isopentenyl diphosphate.

"Substituted" as used to describe a compound or chemical moiety refers to that at least one hydrogen atom of that compound or chemical moiety is replaced with a second chemical moiety. The second chemical moiety can be any desired substituent that does not adversely affect the desired activity of the compound. Examples of substituents are those found in the exemplary compounds and embodiments disclosed herein, as well as halogen; alkyl; heteroalkyl; alkenyl; alkynyl; aryl, heteroaryl, hydroxyl; alkoxyl; amino; nitro; thiol; thioether; imine; cyano; amido; phosphonato; phosphine; carboxyl; thiocarbonyl; sulfonyl; sulfonamide; carbonyl; formyl; carbonyloxy; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —$CO_2CH_3$; —$CONH_2$; —$OCH_2CONH_2$; —$NH_2$; —$SO_2NH_2$; —$OCHF_2$; —$CF_3$; —$OCF_3$; —NH (alkyl); —N(alkyl)$_2$; —NH(aryl); —N(alkyl)(aryl); —N(aryl)$_2$; —CHO; —CO(alkyl); —CO(aryl); —$CO_2$ (alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise.

"Organolithium reagent" refers to an organometallic compound with a direct bond between a carbon and a lithium atom. Some non-limiting examples of organolithium reagents include vinyllithium, aryllithium (e.g., phenyllithium), and alkyllithium (e.g., n-butyl lithium, sec-butyl lithium, tent-butyl lithium, methyllithium, isopropyllithium or other alkyllithium reagents having 1 to 20 carbon atoms).

A composition that is "substantially free" of a compound means that the composition contains less than about 20 wt. %, less than about 10 wt. %, less than about 5 wt. %, less than about 3 wt. %, less than about 1 wt. %, less than about 0.5 wt. %, less than about 0.1 wt. %, or less than about 0.01 wt. % of the compound, based on the total volume of the composition.

A polymer that is "substantially linear" means that the polymer contains less than about 20 wt. %, less than about 10 wt. %, less than about 5 wt. %, less than about 3 wt. %, less than about 1 wt. %, less than about 0.5 wt. %, less than about 0.1 wt. %, or less than about 0.01 wt. % of the branched, star-shaped or other regular or irregular structures, based on the total volume of the composition.

A polymer that is "substantially branched" means that the polymer contains less than about 20 wt. %, less than about 10 wt. %, less than about 5 wt. %, less than about 3 wt. %, less than about 1 wt. %, less than about 0.5 wt. %, less than about 0.1 wt. %, or less than about 0.01 wt. % of the linear, star-shaped or other regular or irregular structures, based on the total volume of the composition.

A polymer that is "substantially star-shaped" means that the polymer contains less than about 20 wt. %, less than about 10 wt. %, less than about 5 wt. %, less than about 3 wt. %, less than about 1 wt. %, less than about 0.5 wt. %, less than about 0.1 wt. %, or less than about 0.01 wt. % of the branched, linear or other regular or irregular structures, based on the total volume of the composition.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

The compositions disclosed herein generally comprise a polyfarnesene and optionally a tackifier. In other embodiments, the compositions disclosed herein do not comprise a tackifier. In further embodiments, the compositions disclosed herein comprise a tackifier.

In some embodiments, the polyfarnesene is a farnesene homopolymer, a farnesene interpolymer or a combination thereof. In certain embodiments, the polyfarnesene is a farnesene homopolymer comprising units derived from at least one farnesene such as α-farnesene, β-farnesene or a combination thereof. In other embodiments, the polyfarnesene is a farnesene interpolymer comprising units derived from at least one farnesene and units derived from at least one copolymerizable vinyl monomer. In further embodiments, the farnesene interpolymer is derived from styrene and at least one farnesene. In still further embodiments, the farnesene interpolymer is a random, block or alternating interpolymer. In still further embodiments, the farnesene interpolymer is a di-block, tri-block or other multi-block interpolymer.

In some embodiments, the farnesene homopolymer is prepared by polymerizing β-farnesene in the presence of any catalyst suitable for polymerizing olefins such as ethylene, styrene or isoprene. In other embodiments, the farnesene homopolymer comprises one or more units having formula (I), (II), (III), (IV), a stereoisomer thereof or a combination thereof:

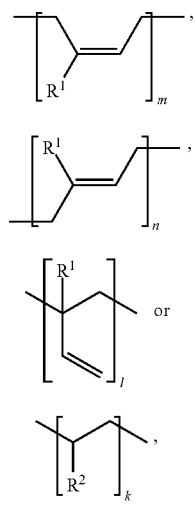

wherein $R^1$ has formula (XI):

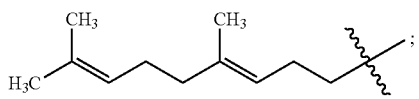

and
$R^2$ has formula (XII):

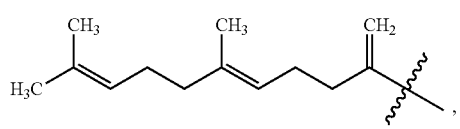

wherein each of m, n, l and k is independently an integer from 1 to about 5,000, from 1 to about 10,000, from 1 to about 50,000, from 1 to about 100,000, from 1 to about 200,000, from 1 to about 500,000, from 2 to about 10,000, from 2 to about 50,000, from 2 to about 100,000, from 2 to about 200,000, or from 2 to about 500,000. In some embodiments, each of m, n, l and k is independently an integer from 1 to 100,000. In other embodiments, each of m, n, l and k is independently an integer from 2 to 100,000.

In certain embodiments, the farnesene homopolymer comprises at least one unit having formula (I) wherein m is greater than about 300, greater than about 500 or greater than about 1000. In other embodiments, the farnesene homopolymer comprises at least one unit having formula (II) wherein n is greater than about 300, greater than about 500 or greater than about 1000. In further embodiments, the farnesene homopolymer comprises at least one unit having formula (III) wherein l is greater than about 300, greater than about 500 or greater than about 1000. In still further embodiments, the farnesene homopolymer comprises at least one unit having formula (IV) wherein k is greater than about 300, greater than about 500 or greater than about 1000.

In some embodiments, the farnesene homopolymer comprises at least one unit having formula (I) and at least one unit having formula (II), wherein the sum of m and n is greater than about 300, greater than about 500 or greater than about 1000. In other embodiments, the farnesene homopolymer comprises at least one unit having formula (I) and at least one unit having formula (III), wherein the sum of m and l is greater than about 300, greater than about 500 or greater than about 1000. In other embodiments, the farnesene homopolymer comprises at least one unit having formula (II) and at least one unit having formula (III), wherein the sum of n and l is greater than about 300, greater than about 500 or greater than about 1000. In still further embodiments, the farnesene homopolymer comprises at least one unit having formula (I), at least one unit having formula (II) and at least one unit having formula (III), wherein the sum of m, n and l is greater than about 300, greater than about 500 or greater than about 1000. In still further embodiments, the farnesene homopolymer comprises at least one unit having formula (I), at least one unit having formula (II), at least one unit having formula (III) and at least one unit having formula (IV), wherein the sum of m, n, l and k is greater than about 300, greater than about 500 or greater than about 1000. In still further embodiments, the one or more units having formula (I), (II), (III) or (IV) in the farnesene homopolymer disclosed herein can be in any order.

In certain embodiments, the farnesene homopolymer is prepared by polymerizing α-farnesene in the presence of any catalyst suitable for polymerizing olefins. In other embodiments, the farnesene homopolymer comprises one or more units having formula (V), (VI), (VII), (VIII), a stereoisomer thereof or a combination thereof:

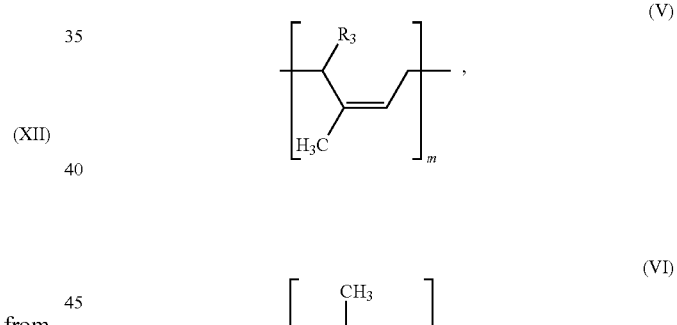

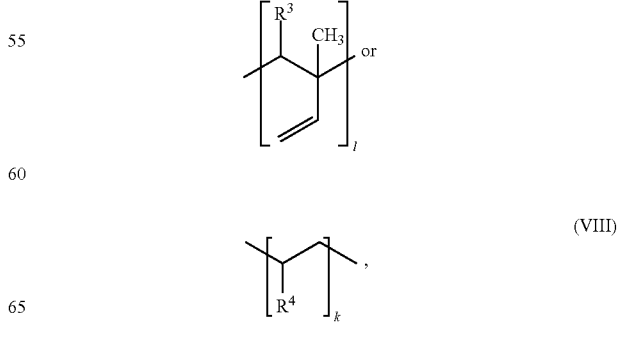

wherein R³ has formula (XIII):

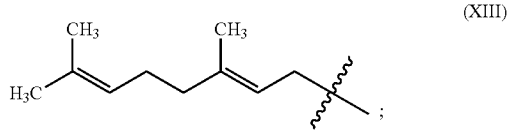

(XIII)

and

R⁴ has formula (XIV):

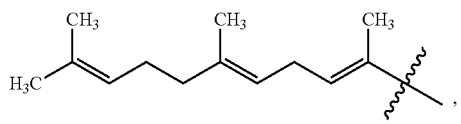

(XIV)

wherein each of m, n, l and k is independently an integer from 1 to about 5,000, from 1 to about 10,000, from 1 to about 50,000, from 1 to about 100,000, from 1 to about 200,000, from 1 to about 500,000, from 2 to about 10,000, from 2 to about 50,000, from 2 to about 100,000, from 2 to about 200,000, or from 2 to about 500,000. In some embodiments, each of m, n, l and k is independently an integer from 1 to 100,000. In other embodiments, each of m, n, l and k is independently an integer from 2 to 100,000.

In certain embodiments, the farnesene homopolymer comprises at least one unit having formula (V) wherein m is greater than about 300, greater than about 500 or greater than about 1000. In other embodiments, the farnesene homopolymer comprises at least one unit having formula (VI) wherein n is greater than about 300, greater than about 500 or greater than about 1000. In further embodiments, the farnesene homopolymer comprises at least one unit having formula (VII) wherein l is greater than about 300, greater than about 500 or greater than about 1000. In still further embodiments, the farnesene homopolymer comprises at least one unit having formula (VIII) wherein k is greater than about 300, greater than about 500 or greater than about 1000.

In some embodiments, the farnesene homopolymer comprises at least one unit having formula (V) and at least one unit having formula (VI), wherein the sum of m and n is greater than about 300, greater than about 500 or greater than about 1000. In other embodiments, the farnesene homopolymer comprises at least one unit having formula (V) and at least one unit having formula (VII), wherein the sum of m and l is greater than about 300, greater than about 500 or greater than about 1000. In other embodiments, the farnesene homopolymer comprises at least one unit having formula (VI) and at least one unit having formula (VII), wherein the sum of n and l is greater than about 300, greater than about 500 or greater than about 1000. In still further embodiments, the farnesene homopolymer comprises at least one unit having formula (V), at least one unit having formula (VI) and at least one unit having formula (VII), wherein the sum of m, n and l is greater than about 300, greater than about 500 or greater than about 1000. In still further embodiments, the farnesene homopolymer comprises at least one unit having formula (V), at least one unit having formula (VI), at least one unit having formula (VII) and at least one unit having formula (VIII), wherein the sum of m, n, l and k is greater than about 300, greater than about 500 or greater than about 1000. In still further embodiments, the one or more units having formula (V), (VI), (VII) or (VIII) in the farnesene homopolymer disclosed herein can be in any order.

In some embodiments, the farnesene homopolymer is prepared by polymerizing a mixture of α-farnesene and β-farnesene in the presence of any catalyst suitable for polymerizing olefins. In other embodiments, the farnesene homopolymer comprises one or more units having formula (I), (II), (III), (IV), (V), (VI), (VII) or (VIII) disclosed herein, a stereoisomer thereof or a combination thereof. In further embodiments, the one or more units having formula (I), (II), (III), (IV), (V), (VI), (VII) or (VIII) in the farnesene homopolymer disclosed herein can be in any order.

In some embodiments, the farnesene homopolymer comprises two or more units having two different formulae selected from formulae (I), (II), (III), (IV), (V), (VI), (VII), (VIII), stereoisomers thereof and combinations thereof. In other embodiments, such farnesene homopolymer can be represented by the following formula: $A_xB_y$, wherein each of x and y is at least 1, and wherein each of A and B independently has formula (I), (II), (III), (IV), (V), (VI), (VII) or (VIII) and A and B are different. In further embodiment, each of x and y is independently greater than 1, such as 2, 3, 4, 5, 6, 7, 8, 9, 10, 15, 20, 25, 30, 35, 40, or higher. In some embodiment, the As and Bs are linked in a substantially linear fashion, as opposed to a substantially branched or substantially star-shaped fashion. In other embodiments, the As and Bs are randomly distributed along the farnesene homopolymer chain. In other embodiments, the As and Bs are in two "segments" to provide a farnesene homopolymer having a segmented structure, for example, AA—A-BB—-B. In other embodiments, the As and Bs are alternatively distributed along the farnesene homopolymer chain to provide a farnesene homopolymer having an alternative structure, for example, A-B, A-B-A, A-B-A-B, A-B-A-B-A or the like.

In some embodiments, the farnesene homopolymer comprises three or more units having three different formulae selected from formulae (I), (II), (III), (IV), (V), (VI), (VII), (VIII), stereoisomers thereof and combinations thereof. In other embodiments, such farnesene homopolymer can be represented by the following formula: $A_xB_yC_z$ wherein each of x, y and z is at least 1, and wherein each of A, B and C independently has formula (I), (II), (III), (IV), (V), (VI), (VII) or (VIII) and A, B and C are different. In further embodiment, each of x, y and z is independently greater than 1, such as 2, 3, 4, 5, 6, 7, 8, 9, 10, 15, 20, 25, 30, 35, 40, or higher. In some embodiment, the As, Bs and Cs are linked in a substantially linear fashion, as opposed to a substantially branched or substantially star-shaped fashion. In other embodiments, the As, Bs and Cs are randomly distributed along the farnesene homopolymer chain. In other embodiments, the As, Bs and Cs are in three "segments" to provide a farnesene homopolymer having a segmented structure, for example, AA—A-BB—B-CC—C. In other embodiments, the As, Bs and Cs are alternatively distributed along the farnesene homopolymer chain to provide a farnesene homopolymer having an alternative structure, for example, A-B-C-A-B, A-B-C-A-B-C or the like.

In certain embodiments, the polyfarnesene is a farnesene interpolymer. In other embodiments, the farnesene interpolymer is prepared by polymerizing at least one farnesene and at least one vinyl monomer in the presence of any catalyst suitable for polymerizing olefins and vinyl monomers. In further embodiments, the farnesene interpolymer disclosed herein comprises (a) one or more units having at least one of formulae (I), (II), (III) and (IV) disclosed herein; and (b) one or more units having formula (IX):

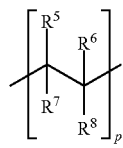

(IX)

wherein p is an integer from 1 to about 5,000, from 1 to about 10,000, from 1 to about 50,000, from 1 to about 100,000, from 1 to about 200,000, from 1 to about 500,000, from 2 to about 10,000, from 2 to about 50,000, from 2 to about 100,000, from 2 to about 200,000, or from 2 to about 500,000; and each of $R^5$, $R^6$, $R^7$ and $R^8$ is independently H, an organyl group, or a functional group. In some embodiments, each of $R^5$, $R^6$, $R^7$ and $R^8$ is not a monovalent hydrocarbon group containing 4-8 carbon atoms. In some embodiments, each of $R^5$, $R^6$, $R^7$ and $R^8$ is not an alkyl group containing 4-8 carbon atoms.

In some embodiments, the farnesene interpolymer disclosed herein comprises (a) one or more units having at least one of formulae (V), (VI), (VII) and (VIII) disclosed herein; and (b) one or more units having formula (IX) disclosed herein. In other embodiments, the farnesene interpolymer disclosed herein comprises (a) one or more units having at least one of formulae (I), (II), (III), (IV), (V), (VI), (VII) and (VIII) disclosed herein; and (b) one or more units having formula (IX) disclosed herein.

In some embodiments, the farnesene interpolymer disclosed herein is a random interpolymer. In other embodiments, the farnesene interpolymer disclosed herein is a random interpolymer wherein the vinyl monomer units and the farnesene units are randomly distributed. In further embodiments, the farnesene interpolymer disclosed herein is a random interpolymer wherein the vinyl monomer units and the farnesene units are randomly distributed and wherein two or more of formulae (I), (II), (III), (IV), (V), (VI), (VII), (VIII) and (XI) in the farnesene units are distributed randomly, alternatively or in blocks.

In some embodiments, the farnesene interpolymer disclosed herein is an alternating interpolymer. In other embodiments, the farnesene interpolymer disclosed herein is an alternating interpolymer wherein the vinyl monomer units and the farnesene units are alternatively distributed. In further embodiments, the farnesene interpolymer disclosed herein is an alternating interpolymer wherein the vinyl monomer units and the farnesene units are alternatively distributed and wherein two or more of formulae (I), (II), (III), (IV), (V), (VI), (VII), (VIII) and (XI) in the farnesene units are distributed randomly, alternatively or in blocks.

In certain embodiments, the farnesene interpolymer is a block interpolymer having one or more first blocks comprising the one or more units having formula (I), (II), (III), (IV) or a combination thereof and one or more second blocks comprising the one or more units having formula (IX). In further embodiments, the farnesene interpolymer is a block interpolymer having one or more first blocks comprising the one or more units having formula (V), (VI), (VII), (VIII) or a combination thereof and one or more second blocks comprising the one or more units having formula (IX). In still further embodiments, there are one first block and two second blocks and wherein the first block is between the two second blocks. In still further embodiments, each of the second blocks comprises units derived from styrene. In some embodiments, the farnesene block interpolymer is a polystyrene-polyfarnesene di-block polyfarnesene, polystyrene-polyfarnesene-polystyrene tri-block polyfarnesene or a combination thereof.

In some embodiments, the farnesene interpolymer can be represented by the following formula: $P_xQ_y$ wherein each of x and y is at least 1, and wherein P has formula (IX) and Q has formula (I), (II), (III), (IV), (V), (VI), (VII) or (VIII). In further embodiment, each of x and y is independently greater than 1, such as 2, 3, 4, 5, 6, 7, 8, 9, 10, 15, 20, 25, 30, 35, 40, or higher. In some embodiment, the Ps and Qs are linked in a substantially linear fashion, as opposed to a substantially branched or substantially star-shaped fashion. In other embodiments, the Ps and Qs are randomly distributed along the farnesene interpolymer chain. In other embodiments, the Ps and Qs are in two or more blocks or segments to provide a farnesene interpolymer having a block structure, for example, PP—P-QQ—-Q or PP—P-QQ—-Q-P—-PP. In other embodiments, the Ps and Qs are alternatively distributed along the farnesene interpolymer chain to provide a farnesene interpolymer having an alternative structure, for example, P-Q, P-Q-P, P-Q-P-Q, P-Q-P-Q-P or the like. In some embodiments, each Q has formula $A_xB_y$ or $A_xB_yC_z$ as disclosed herein.

In certain embodiments, the amount of formula (I) in the polyfarnesene disclosed herein is at most about 85 wt. %, at most about 80 wt. %, at most about 70 wt. %, at most about 60 wt. %, or at most about 50 wt. %, based on the total weight of the polyfarnesene. In other embodiments, the amount of formula (III) in the polyfarnesene disclosed herein is at least about 10 wt. %, at least about 15 wt. %, at least about 20 wt. %, at least about 25 wt. %, at least about 30 wt. %, at least about 40 wt. %, at least about 50 wt. %, at least about 60 wt. %, at least about 70 wt. %, at least about 80 wt. %, at least about 90 wt. %, at least about 95 wt. %, or at least about 99 wt. %, based on the total weight of the polyfarnesene. In further embodiments, the amount of formula (II) in the polyfarnesene disclosed herein is from about 1 wt. % to about 99 wt. %, from about 5 wt. % to about 99 wt. %, from about 10 wt. % to about 99 wt. %, or from about 15 wt. % to about 99 wt. %, based on the total weight of the polyfarnesene. In still further embodiments, the amount of formula (IV) in the polyfarnesene disclosed herein is at most about 0.1 wt. %, at most about 0.5 wt. %, at most about 1 wt. %, at most about 2 wt. %, or at most about 3 wt. %, based on the total weight of the polyfarnesene. In some embodiments, the polyfarnesene disclosed herein is substantially free of formula (I), (II), (III) or (IV).

In certain embodiments, the amount of formula (V), (VI), (VII) or (VIII) in the polyfarnesene disclosed herein is at most about 1 wt. %, at most about 5 wt. %, at most about 10 wt. %, at most about 20 wt. %, at most about 30 wt. %, at most about 40 wt. %, at most about 50 wt. %, at most about 60 wt. %, at most about 70 wt. %, at most about 80 wt. %, or at most about 90 wt. %, based on the total weight of the polyfarnesene. In other embodiments, the amount of formula (V), (VI), (VII) or (VIII) in the polyfarnesene disclosed herein is at least about 1 wt. %, at least about 2 wt. %, at least about 3 wt. %, at least about 5 wt. %, at least about 10 wt. %, at least about 20 wt. %, at least about 30 wt. %, at least about 40 wt. %, at least about 50 wt. %, at least about 60 wt. %, based on the total weight of the polyfarnesene. In further embodiments, the amount of formula (V), (VI), (VII) or (VIII) in the polyfarnesene disclosed herein is from about 1 wt. % to about 99 wt. %, from about 5 wt. % to about 99 wt. %, from about 10 wt. % to about 99 wt. %, or from about 15 wt. % to about 99 wt. %, based on the total weight of the polyfarnesene. In some embodiments, the polyfarnesene disclosed herein is substantially free of formula (V), (VI), (VII) or (VIII).

In other embodiments, the sum of m and n disclosed herein is greater than about 250, greater than about 300, greater than about 500, greater than about 750, greater than about 1000, or greater than about 2000. In further embodiments, the sum of m and l disclosed herein is greater than about 250, greater than about 300, greater than about 500, greater than about 750, greater than about 1000, or greater than about 2000. In certain embodiments, the sum of m, n and l disclosed herein is greater than about 250, greater than about 300, greater than about 500, greater than about 750, greater than about 1000, or greater than about 2000. In some embodiments, the sum of m, n, l and k disclosed herein is greater than about 250, greater than about 300, greater than about 500, greater than about 750, greater than about 1000, or greater than about 2000.

In certain embodiments, the number-average molecular weight ($M_n$), weight-average molecular weight ($M_w$), or viscosity-average molecular weight ($M_z$) of the polyfarnesene disclosed herein is greater than about 60,000 daltons, greater than about 100,000 daltons, greater than 200,000 daltons, greater than 300,000 daltons, greater than about 500,000 daltons, greater than 750,000 daltons, greater than 1,000,000 daltons, greater than 1,500,000 daltons, or greater than 2,000,000 daltons. In other embodiments, the $M_n$, $M_w$ or $M_z$ of the polyfarnesene disclosed herein is less than about 10,000,000 daltons, less than 5,000,000 daltons, less than 1,000,000 daltons, less than about 750,000 daltons, or less than 500,000 daltons.

In some embodiments, the polyfarnesene has at least a glass transition temperature ($T_g$) of less than −55° C., less than −60° C., less than −65° C., less than −70° C., or less than −75° C., as measured according to ASTM D7426-08 titled "Standard Test Method for Assignment of the DSC Procedure for Determining $T_g$ of a Polymer or an Elastomeric Compound," which is incorporated herein by reference.

In some embodiments, the amount of formula (I) is at most about 80 wt. %, based on the total weight of the polyfarnesene. In other embodiments, the sum of m, n and l is greater than about 300. In further embodiments, at least a portion of the double bonds in one or more of formulae (I), (II), (III), (IV), (IX), (XI), (XII) and stereoisomers thereof is hydrogenated.

In some embodiments, the polyfarnesene is a farnesene interpolymer. In further embodiments, the farnesene interpolymer disclosed herein comprises one or more units derived from a farnesene in an amount of at least about 5 mole percent, at least about 10 mole percent, at least about 15 mole percent, at least about 20 mole percent, at least about 30 mole percent, at least about 40 mole percent, at least about 50 mole percent, at least about 60 mole percent, at least about 70 mole percent, at least about 80 mole percent, or at least about 90 mole percent of the whole farnesene interpolymer. In still further embodiments, the farnesene interpolymer disclosed herein comprises one or more units derived from the vinyl monomer in an amount of at least about 5 mole percent, at least about 10 mole percent, at least about 15 mole percent, at least about 20 mole percent, at least about 30 mole percent, at least about 40 mole percent, at least about 50 mole percent, at least about 60 mole percent, at least about 70 mole percent, at least about 80 mole percent, or at least about 90 mole percent of the whole farnesene interpolymer.

In certain embodiments, the polyfarnesene comprises one or more polymer molecules having formula (X'):

(X')

wherein n is an integer from 1 to about 5,000, from 1 to about 10,000, from 1 to about 50,000, from 1 to about 100,000, from 1 to about 200,000, or from 1 to about 500,000; m is an integer from 0 to about 5,000, from 0 to about 10,000, from 0 to about 50,000, from 0 to about 100,000, from 0 to about 200,000, or from 0 to about 500,000; X is derived from a farnesene; and Y is derived from a vinyl monomer.

In some embodiments, X has one or more of formulae (I')-(VIII'):

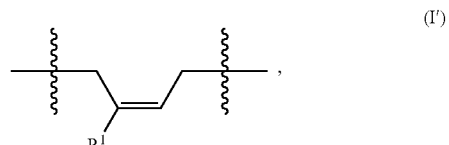

(I')

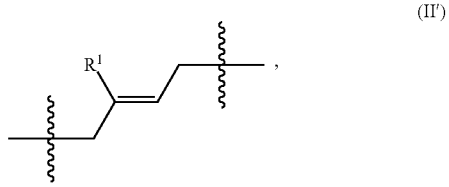

(II')

(III')

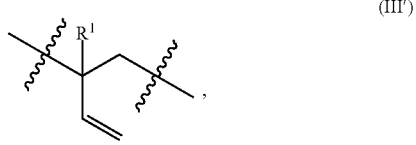

(IV')

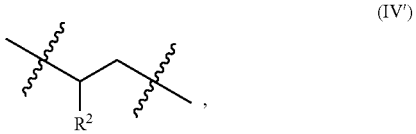

(V')

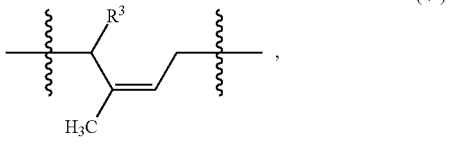

(VI')

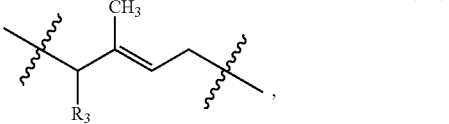

(VII')

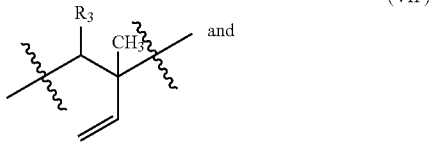

and (VIII')

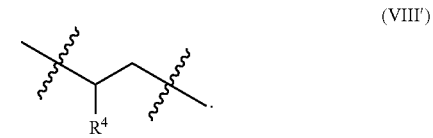

In certain embodiments, Y has formula (IX'):

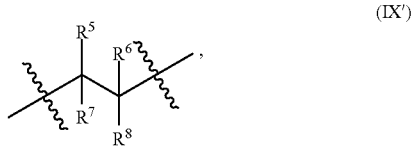

where $R^1$, $R^2$, $R^3$, $R^4$ are as defined herein and each of $R^5$, $R^6$, $R^7$ and $R^8$ is independently H, an organyl group or a functional group.

In general, the polyfarnesene comprising a mixture of polymer molecules, each of which has formula (X') wherein each of n and m independently has a specific value. The average and distribution of the n or m values disclosed herein depend on various factors such as the molar ratio of the starting materials, the reaction time and temperature, the presence or absence of a chain terminating agent, the amount of an initiator if there is any, and the polymerization conditions. The farnesene interpolymer of Formula (X') may include unreacted comonomers, although the concentrations of the comonomer would generally be small if not extremely small or undetectable. The extent of polymerization, as specified with n and m values, can affect the properties of the resulting polymer. In some embodiments, n is an integer from 1 to about 5,000, from 1 to about 10,000, from 1 to about 50,000, from 1 to about 100,000, from 1 to about 200,000, or from 1 to about 500,000; and m is an integer from 0 to about 5,000, from 0 to about 10,000, from 0 to about 50,000, from 0 to about 100,000, from 0 to about 200,000, or from 0 to about 500,000. In other embodiments, n is independently from about 1 to about 5000, from about 1 to about 2500, from about 1 to about 1000, from about 1 to about 500, from about 1 to about 100 or from about 1 to about 50; and m is from about 0 to about 5000, from about 0 to about 2500, from about 0 to about 1000, from about 0 to about 500, from about 0 to about 100 or from about 0 to about 50. A person of ordinary skill in the art will recognize that additional ranges of average n and m values are contemplated and are within the present disclosure.

In some embodiments, formula (X') comprises two end groups as shown by the following formula:

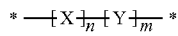

where each of the asterisks (*) in the formula represents an end group which may or may not vary between different polymer molecules of the polyfarnesene depending on many factors such as the molar ratio of the starting materials, the presence or absence of a chain terminating agent, and the state of the particular polymerization process at the end of the polymerization step.

In some embodiments, Xs and Ys of formula (X') are linked in a substantially linear fashion. In other embodiments, Xs and Ys of formula (X') are linked in substantially branched fashion. In further embodiments, Xs and Ys of formula (X') are linked in substantially star-shaped fashion. In still further embodiments, each of Xs and Ys independently forms at least a block along the polymer chain so as to provide a di-block, tri-block or multi-block farnesene interpolymer having at least one X block and at least one Y block. In still further embodiments, Xs and Ys are randomly distributed along the polymer chain so as to provide a random farnesene interpolymer. In still further embodiments, Xs and Ys are alternatively distributed along the polymer chain so as to provide an alternating farnesene interpolymer.

In some embodiments, the amount of the farnesene in the farnesene interpolymer disclosed herein is greater than about 1.5 mole %, greater than about 2.0 mole %, greater than about 2.5 mole %, greater than about 5 mole %, greater than about 10 mole %, greater than about 15 mole %, or greater than about 20 mole %, based on the total amount of the farnesene interpolymer. In other embodiments, the amount of the farnesene in the farnesene interpolymer disclosed herein is less than about 90 mole %, less than about 80 mole %, less than about 70 mole %, less than about 60 mole %, less than about 50 mole %, less than about 40 mole %, or less than about 30 mole %, based on the total amount of the farnesene interpolymer.

In some embodiments, the amount of the vinyl monomer in the farnesene interpolymer disclosed herein is greater than about 1.5 mole %, greater than about 2.0 mole %, greater than about 2.5 mole %, greater than about 5 mole %, greater than about 10 mole %, greater than about 15 mole %, or greater than about 20 mole %, based on the total amount of the farnesene interpolymer. In other embodiments, the amount of the vinyl monomer in the farnesene interpolymer disclosed herein is less than about 90 mole %, less than about 80 mole %, less than about 70 mole %, less than about 60 mole %, less than about 50 mole %, less than about 40 mole %, or less than about 30 mole %, based on the total amount of the farnesene interpolymer.

In certain embodiments, the mole percent ratio of the farnesene to the vinyl monomer (i.e., the mole percent ratio of X to Y) in the farnesene interpolymer disclosed herein is from about 1:5 to about 100:1. In other embodiments, the mole percent ratio of X to Y is from about 1:4 to about 100:1; from about 1:3.5 to about 100:1, from about 1:3 to about 100:1, from about 1:2.5 to about 100:1, or from about 1:2 to about 100:1. In some embodiments, m is 1 or greater, the mole percent ratio of X to Y is from about 1:4 to about 100:1

In certain embodiments, the amount of formula (I') in the polyfarnesene disclosed herein is at most about 85 wt. %, at most about 80 wt. %, at most about 70 wt. %, at most about 60 wt. %, or at most about 50 wt. %, based on the total weight of the polyfarnesene. In other embodiments, the amount of formula (III') in the polyfarnesene disclosed herein is at least about 10 wt. %, at least about 15 wt. %, at least about 20 wt. %, at least about 25 wt. %, at least about 30 wt. %, at least about 40 wt. %, at least about 50 wt. %, at least about 60 wt. %, at least about 70 wt. %, at least about 75 wt. %, at least about 80 wt. %, at least about 85 wt. %, at least about 90 wt. %, at least about 95 wt. %, or at least about 99 wt. %, based on the total weight of the polyfarnesene. In further embodiments, the amount of formula (II') in the polyfarnesene disclosed herein is from about 1 wt. % to about 99 wt. %, from about 5 wt. % to about 99 wt. %, from about 10 wt. % to about 99 wt. %, or from about 15 wt. % to about 99 wt. %, based on the total weight of the polyfarnesene. In still further embodiments, the amount of formula (IV') in the polyfarnesene disclosed herein is at most about 0.1 wt. %, at most about 0.5 wt. %, at most about 1 wt. %, at most about 2 wt. %, or at most about 3 wt. %, based on the total weight of the polyfarnesene. In some embodiments, the polyfarnesene disclosed herein is substantially free of formula (I'), (II'), (III') or (IV').

In certain embodiments, the amount of formula (V'), (VI'), (VII') or (VIII') in the polyfarnesene disclosed herein is at most about 1 wt. %, at most about 5 wt. %, at most about 10 wt. %, at most about 20 wt. %, at most about 30 wt. %, at most about 40 wt. %, at most about 50 wt. %, at most about 60 wt. %, at most about 70 wt. %, at most about 80 wt. %, or at most about 90 wt. %, based on the total weight of the polyfarnesene. In other embodiments, the amount of formula (V'), (VI'), (VII') or (VIII') in the polyfarnesene disclosed herein is at least about 1 wt. %, at least about 2 wt. %, at least about 3 wt. %, at least about 5 wt. %, at least about 10 wt. %, at least about 20 wt. %, at least about 30 wt. %, at least about 40 wt. %, at least about 50 wt. %, at least about 60 wt. %, based on the total weight of the polyfarnesene. In further embodiments, the amount of formula (V'), (VI'), (VII') or (VIII') in the polyfarnesene disclosed herein is from about 1 wt. % to about 99 wt. %, from about 5 wt. % to about 99 wt. %, from about 10 wt. % to about 99 wt. %, or from about 15 wt. % to about 99 wt. %, based on the total weight of the polyfarnesene. In some embodiments, the polyfarnesene disclosed herein is substantially free of formula (V'), (VI'), (VII') or (VIII').

Any compound containing a vinyl group, i.e., —CH=CH$_2$, that is copolymerizable with farnesene can be used as a vinyl monomer for making the farnesene interpolymer disclosed herein. Useful vinyl monomers disclosed herein include ethylene, i.e., CH$_2$=CH$_2$. In certain embodiments, the vinyl monomer has formula (XV):

where each of $R^5$, $R^6$, $R^7$ and $R^8$ is independently H, an organyl group or a functional group.

In some embodiments, at least one of $R^5$, $R^6$, $R^7$ and $R^8$ of formula (IX), (IX') or (XV) is an organyl group. In further embodiments, the organyl group is hydrocarbyl, substituted hydrocarbyl, heterocyclyl or substituted heterocyclyl. In certain embodiments, each of $R^5$, $R^6$, $R^7$ and $R^8$ of formula (IX), (IX') or (XV) is independently H, alkyl, cycloalkyl, aryl, alkenyl, cycloalkenyl, alkynyl, heterocyclyl, alkoxy, aryloxy, carboxy, alkoxycarbonyl, aminocarbonyl, alkylaminocarbonyl, dialkylaminocarbonyl, acyloxy, nitrile or halo. In other embodiments, each of $R^5$, $R^6$, $R^7$ and $R^8$ of formula (IX), (IX') or (XV) is independently H, alkyl, cycloalkyl, aryl, cycloalkenyl, alkynyl, heterocyclyl, alkoxy, aryloxy, carboxy, alkoxycarbonyl, aminocarbonyl, alkylaminocarbonyl, dialkylaminocarbonyl, acyloxy, nitrile or halo. In certain embodiments, $R^5$ of formula (IX), (IX') or (XV) is aryl; and each of $R^6$, $R^7$ and $R^8$ is H. In further embodiments, $R^5$ of formula (IX), (IX') or (XV) is phenyl; and each of $R^6$, $R^7$ and $R^8$ is H.

In certain embodiments, at least one of $R^5$, $R^6$, $R^7$ and $R^8$ of formula (IX), (IX') or (XV) is H. In other embodiments, each of $R^5$, $R^6$, $R^7$ and $R^8$ of formula (IX), (IX') or (XV) is H. In further embodiments, $R^5$ of formula (IX), (IX') or (XV) is hydrocarbyl; and each of $R^6$, $R^7$ and $R^8$ is H. In still further embodiments, the hydrocarbyl is alkyl, cycloalkyl or aryl. In still further embodiments, none of $R^5$, $R^6$, $R^7$ and $R^8$ of formula (IX), (IX') or (XV) is or comprises alkenyl, cycloalkenyl or alkynyl. In still further embodiments, none of $R^5$, $R^6$, $R^7$ and $R^8$ of formula (IX), (IX') or (XV) is or comprises a hydrocarbyl, substituted hydrocarbyl, heterocyclyl or substituted heterocyclyl.

In certain embodiments, at least one of $R^5$, $R^6$, $R^7$ and $R^8$ of formula (IX), (IX') or (XV) is a functional group containing halo, O, N, S, P or a combination thereof. Some non-limiting examples of suitable functional groups include hydroxy, alkoxy, aryloxy, amino, nitro, thiol, thioether, imine, cyano, amido, phosphonato (—P(=O)(O-alkyl)$_2$, —P(=O)(O-aryl)$_2$, or —P(=O)(O-alkyl))O-aryl), phosphinato (—P(=O)(O-alkyl)alkyl, —P(=O)(O-aryl)alkyl, —P(=O)(O-alkyl)aryl, or —P(=O)(O-aryl)aryl), carboxyl, thiocarbonyl, sulfonyl (—S(=O)$_2$alkyl, or —S(=O)$_2$aryl), sulfonamide (—SO$_2$NH$_2$, —SO$_2$NH(alkyl), —SO$_2$NH(aryl), —SO$_2$N(alkyl)$_2$, —SO$_2$N(aryl)$_2$, or —SO$_2$N(aryl)(alkyl)), ketone, aldehyde, ester, oxo, amino (primary, secondary or tertiary), —CO$_2$CH$_3$, —CONH$_2$, —OCH$_2$CONH$_2$, —NH$_2$, —OCHF$_2$, —OCF$_3$, —NH(alkyl), —N(alkyl)$_2$, —NH(aryl), —N(alkyl)(aryl), —N(aryl)$_2$, —CHO, —CO(alkyl), —CO(aryl), —CO$_2$(alkyl), or —CO$_2$(aryl). In some embodiments, the functional group is or comprises alkoxy, aryloxy, carboxy, alkoxycarbonyl, aminocarbonyl, alkylaminocarbonyl, dialkylaminocarbonyl, acyloxy, nitrile or halo. In other embodiments, none of $R^5$, $R^6$, $R^7$ and $R^8$ of formula (IX), (IX') or (XV) is or comprises a functional group. In other embodiments, none of $R^5$, $R^6$, $R^7$ and $R^8$ of formula (IX), (IX') or (XV) is or comprises alkoxy, aryloxy, carboxy, alkoxycarbonyl, aminocarbonyl, alkylaminocarbonyl, dialkylaminocarbonyl, acyloxy, nitrile or halo.

In some embodiments, the vinyl monomer is a substituted or unsubstituted olefin such as ethylene or styrene, vinyl halide, vinyl ether, acrylonitrile, acrylic ester, methacrylic ester, acrylamide, methacrylamide or a combination thereof. In other embodiments, the vinyl monomer is ethylene, an α-olefin or a combination thereof. Some non-limiting examples of suitable α-olefins include styrene, propylene, 1-butene, 1-hexene, 1-octene, 4-methyl-1-pentene, norbornene, 1-decene, 1,5-hexadiene and combinations thereof.

In some embodiments, the vinyl monomer is an aryl such as styrene, α-methyl styrene, or di-vinyl benzene. Additional examples include the functionalized vinyl aryls such as those disclosed by U.S. Pat. No. 7,041,761 which is incorporated herein by reference.

In some embodiments, the farnesene interpolymers disclosed herein are derived from at least one farnesene and at least one olefin monomer. An olefin refers to an unsaturated hydrocarbon-based compound with at least one carbon-carbon double bond. In certain embodiments, the olefin is a conjugated diene. Depending on the selection of catalysts, any olefin may be used in embodiments of the invention. Some non-limiting examples of suitable olefins include C$_{2-20}$ aliphatic and C$_{8-20}$ aromatic compounds containing vinylic unsaturation, as well as cyclic compounds, such as cyclobutene, cyclopentene, dicyclopentadiene, and norbornene, including but not limited to, norbornene substituted in the 5 and 6 position with C$_{1-20}$ hydrocarbyl or cyclohydrocarbyl groups. Other non-limiting examples of suitable olefins include mixtures of such olefins as well as mixtures of such olefins with C$_{4-40}$ diolefin compounds.

Some non-limiting examples of suitable olefin or α-olefin monomers include styrene, ethylene, propylene, isobutylene, 1-butene, 1-pentene, 1-hexene, 1-heptene, 1-octene, 1-nonene, 1-decene, and 1-dodecene, 1-tetradecene, 1-hexadecene, 1-octadecene, 1-eicosene, 3-methyl-1-butene, 3-methyl-1-pentene, 4-methyl-1-pentene, 4,6-dimethyl-1-heptene, 4-vinylcyclohexene, vinylcyclohexane, norbornadiene, ethylidene norbornene, cyclopentene, cyclohexene, dicyclopentadiene, cyclooctene, C$_{4-40}$ dienes, including but not limited to 1,3-butadiene, 1,3-pentadiene, 1,4-hexadiene, 1,5-hexadiene, 1,7-octadiene, 1,9-decadiene, other C$_{4-40}$ α-olefins, and the like. In certain embodiments, the olefin monomer is propylene, 1-butene, 1-pentene, 1-hexene, 1-octene or a combination thereof.

The farnesene interpolymers disclosed herein may derived from a farnesene and styrene. The farnesene interpolymers may further comprise at least one $C_{2-20}$ olefin, at least one $C_{4-18}$ diolefin, at least one alkenylbenzene or a combination thereof. Suitable unsaturated comonomers useful for polymerizing with farnesene include, for example, ethylenically unsaturated monomers, polyenes such as conjugated or non-conjugated dienes, alkenylbenzenes, and the like. Examples of such comonomers include ethylene, $C_{2-20}$ olefins such as propylene, isobutylene, 1-butene, 1-hexene, 1-pentene, 4-methyl-1-pentene, 1-heptene, 1-octene, 1-nonene, 1-decene, and the like. Other suitable monomers include styrene, halo- or alkyl-substituted styrenes, vinylbenzocyclobutane, 1,4-hexadiene, 1,7-octadiene, and cycloalkenes such as cyclopentene, cyclohexene and cyclooctene.

Some suitable non-conjugated diene monomers can be a straight chain, branched chain or cyclic hydrocarbon diene having from 6 to 15 carbon atoms. Some non-limiting examples of suitable non-conjugated dienes include straight chain acyclic dienes, such as 1,4-hexadiene, 1,6-octadiene, 1,7-octadiene, 1,9-decadiene, branched chain acyclic dienes, such as 5-methyl-1,4-hexadiene; 3,7-dimethyl-1,6-octadiene; 3,7-dimethyl-1,7-octadiene and mixed isomers of dihydromyricene and dihydroocinene, single ring alicyclic dienes, such as 1,3-cyclopentadiene; 1,4-cyclohexadiene; 1,5-cyclooctadiene and 1,5-cyclododecadiene, and multi-ring alicyclic fused and bridged ring dienes, such as tetrahydroindene, methyl tetrahydroindene, dicyclopentadiene, bicyclo-(2,2,1)-hepta-2,5-diene; alkenyl, alkylidene, cycloalkenyl and cycloalkylidene norbornenes, such as 5-methylene-2-norbornene (MNB); 5-propenyl-2-norbornene, 5-isopropylidene-2-norbornene, 5-(4-cyclopentenyl)-2-norbornene, 5-cyclohexylidene-2-norbornene, 5-vinyl-2-norbornene, and norbornadiene. Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD). In certain embodiments, the diene is 5-ethylidene-2-norbornene (ENB) or 1,4-hexadiene (HD). In other embodiments, the farnesene interpolymers are not derived from a polyene such as dienes, trienes, tetraenes and the like.

In some embodiments, the farnesene interpolymers are interpolymers of farnesene, styrene, and a $C_{2-20}$ olefin. Some non-limiting examples of suitable olefins include ethylene, propylene, isobutylene, 1-butene, 1-pentene, 1-hexene, 4-methyl-1-pentene, and 1-octene. In some embodiments, the farnesene interpolymers disclosed herein are not derived from ethylene. In some embodiments, the farnesene interpolymers disclosed herein are not derived from one or more $C_{2-20}$ olefins.

In certain embodiments, the vinyl monomer does not comprise a terpene. In other embodiments, the vinyl monomer does not comprise a terpene selected from isoprene, dipentene, α-pinene, β-pinene, terpinolene, limonene (dipentene), terpinene, thujene, sabinene, 3-carene, camphene, cadinene, caryophyllene, myrcene, ocimene, cedrene, bisalbone, bisalbone, bisalbone, zingiberene, humulene, citronellol, linalool, geraniol, nerol, ipsenol, terpineol, D-terpineol-(4), dihydrocarveol, nerolidol, farnesol, eudesmol, citral, D-citronellal, carvone, D-pulegone, piperitone, carvenone, bisabolene, selinene, santalene, vitamin A, abietic acid or a combination thereof. In further embodiments, the vinyl monomer does not comprise an isoprene.

The farnesene interpolymers can be functionalized by incorporating at least one functional group in their polymer structure. Exemplary functional groups may include, for example, ethylenically unsaturated mono- and di-functional carboxylic acids, ethylenically unsaturated mono- and di-functional carboxylic acid anhydrides, salts thereof and esters thereof. Such functional groups may be grafted to the farnesene interpolymers, or they may be copolymerized farnesene with an optional additional comonomer to form an interpolymer of farnesene, the functional comonomer and optionally other comonomer(s). Any means for grafting functional groups known to a skilled artisan can be used. One particularly useful functional group is maleic anhydride.

The amount of the functional group present in the functionalized farnesene interpolymer may vary. In some embodiments, the functional group is present in an amount of at least about 1.0 wt. %, at least about 2.5 wt. %, at least about 5 wt. %, at least about 7.5 wt. %, or at least about 10 wt. %, based on the total weight of the farnesene interpolymer. In other embodiments, the functional group is present in an amount of less than about 40 wt. %, less than about 30 wt. %, less than about 25 wt. %, less than about 20 wt. %, or less than about 15 wt. %, based on the total weight of the farnesene interpolymer.

Any catalyst that can polymerize or copolymerize farnesene can be used for making the polyfarnesenes disclosed herein. Some non-limiting examples of suitable catalysts include organolithium reagents, Ziegler-Natta catalysts, Kaminsky catalysts and other metallocene catalysts. In some embodiments, the catalyst is a Ziegler-Natta catalyst, a Kaminsky catalyst, a metallocene catalyst or a combination thereof.

In some embodiments, the catalyst further comprises a cocatalyst. In further embodiments, the cocatalyst is a hydride, alkyl or aryl of a metal or a combination thereof. In still further embodiments, the metal is aluminum, lithium, zinc, tin, cadmium, beryllium or magnesium.

In some embodiments, the catalyst is an organolithium reagent. Any organolithium reagent that can act as a catalyst to polymerize olefins can be used herein. Some non-limiting examples of suitable organolithium reagents include n-butyllithium, sec-butyllithium or tert-butyllithium. Some non-limiting examples of suitable Lewis bases include TMEDA, PMDTA or sparteine. Some organolithium reagents are disclosed in Zvi Rappoport et al., "*The Chemistry of Organolithium Compounds*," Part 1 (2004) and Vol. 2 (2006), both of which are incorporated herein by reference.

In some embodiments, the catalyst is a mixture of an organolithium reagent and a Lewis base. Any Lewis base that can deaggregate organolithium reagents, making them more soluble and more reactive, can be used herein. An aggregated organolithium reagent generally has one lithium coordinating to more than one carbon atom and one carbon coordinating to more than one lithium atom. Some non-limiting examples of suitable Lewis bases include 1,2-bis(dimethylamino)ethane (also known as tetramethylethylenediamine or TMEDA), N,N,N',N',N"-pentamethyldiethylenetriamine (PMDTA), sparteine and combinations thereof.

In some embodiments, the catalyst is a Ziegler-Natta catalyst. Generally, Ziegler-Natta catalysts can be heterogeneous or homogeneous. In some embodiments, the Ziegler-Natta catalyst used for polymerizing the polyfarnesenes disclosed herein is a heterogeneous Ziegler-Natta catalyst. Some useful Ziegler-Natta catalysts are disclosed in J. Boor, "Ziegler-Natta Catalysts and Polymerizations," Saunders College Publishing, pp. 1-687 (1979); and Malcolm P. Stevens, "*Polymer*

*Chemistry, an Introduction,*" Third Edition, Oxford University Press, pp. 236-245 (1999), both of which are incorporated herein by reference.

Heterogeneous Ziegler-Natta catalysts generally comprise (1) a transition metal compound comprising an element from groups IV to VIII; and (2) an organometallic compound comprising a metal from groups I to III of the periodic table. The transition metal compound is referred as the catalyst while the organometallic compound is regarded as the cocatalyst or activator. The transition metal compound generally comprises a metal and one or more anions and ligands. Some non-limiting examples of suitable metals include titanium, vanadium, chromium, molybdenum, zirconium, iron and cobalt. Some non-limiting examples of suitable anions or ligands include halides, oxyhalides, alkoxy, acetylacetonyl, cyclopentadienyl, and phenyl.

Any cocatalyst or activator that can ionize the organometallic complex to produce an active olefin polymerization catalyst can be used herein. Generally, the organometallic cocatalysts are hydrides, alkyls, or aryls of metals, such as aluminum, lithium, zinc, tin, cadmium, beryllium, and magnesium. Some non-limiting examples of suitable cocatalysts include alumoxanes (methyl alumoxane (MAO), PMAO, ethyl alumoxane, diisobutyl alumoxane), alkylaluminum compounds (trimethylaluminum, triethylaluminum, diethyl aluminum chloride, trimethylaluminum, triisobutylaluminum, trioctylaluminum), diethylzinc, di(1-butyl)zinc, di(n-hexyl)zinc, and ethylzinc (t-butoxide) and the like. Other suitable cocatalysts include acid salts that contain non-nucleophilic anions. These compounds generally consist of bulky ligands attached to boron or aluminum. Some non-limiting examples of such compounds include lithium tetrakis(pentafluorophenyl)borate, lithium tetrakis(pentafluorophenyl)aluminate, anilinium tetrakis(pentafluorophenyl)borate, and the like. Some non-limiting examples of suitable cocatalysts also include organoboranes, which include boron and one or more alkyl, aryl, or aralkyl groups. Other non-limiting examples of suitable cocatalysts include substituted and unsubstituted trialkyl and triarylboranes such as tris(pentafluorophenyl)borane, triphenylborane, tri-n-octylborane, and the like. These and other suitable boron-containing cocatalysts or activators are described in U.S. Pat. Nos. 5,153,157, 5,198,401, and 5,241,025, both of which are incorporated herein by reference.

In certain embodiments, the Ziegler-Natta catalyst can be impregnated on a support material. Some suitable support materials are disclosed in Malcolm P. Stevens, "*Polymer Chemistry, an Introduction,*" Third Edition, Oxford University Press, p. 251 (1999), which is incorporated herein by reference.

The support material is generally a material inert or substantially inert to olefin polymerization reactions. Non-limiting examples of suitable support materials include $MgCl_2$, MgO, alumina such as activated alumina and microgel alumina, silica, magnesia, kieselguhr, fuller's earth, clays, alumina silicates, porous rare earth halides and oxylalides, and combinations thereof. The support material can have a surface area between about 5 $m^2/g$ and about 450 $m^2/g$, as determined by the BET (Brunauer-Emmet-Teller) method of measuring surface area, as described by S. Brunauer, P. H. Emmett, and E. Teller, Journal of the American Chemical Society, 60, 309 (1938), which is incorporated herein by reference. In some embodiments, the surface area of the support material is between about 10 $m^2/g$ and about 350 $m^2/g$. In further embodiments, the surface area of the support material is between about 25 $m^2/g$ and about 300 $m^2/g$.

The support material can have an average particle size ranging from about 20 to about 300 microns, from about 20 to about 250 microns, from about 20 to about 200 microns, from about 20 to about 150 microns, from about 20 to about 120 microns, from about 30 to about 100 microns, or from about 30 to about 90 microns. The compacted or tamped bulk density of the support material can vary between about 0.6 and about 1.6 g/cc, between about 0.7 and about 1.5 g/cc, between about 0.8 and about 1.4 g/cc, or between about 0.9 and about 1.3 g/cc.

In certain embodiments, the catalyst used herein is or comprises a Kaminsky catalyst, also known as homogeneous Ziegler-Natta catalyst. The Kaminsky catalyst can be used to produce polyolefins such as the polyfarnesenes disclosed herein with unique structures and physical properties. Some Kaminsky catalysts or homogeneous Ziegler-Natta catalysts are disclosed in Malcolm P. Stevens, "*Polymer Chemistry, an Introduction,*" Third Edition, Oxford University Press, pp. 245-251 (1999); and John Scheirs and Walter Kaminsky, "*Metallocene-Based Polyolefins: Preparation, Properties, and Technology,*" Volume 1, Wiley (2000), both of which are incorporated herein by reference.

In some embodiments, the Kaminsky catalyst suitable for making the polyfarnesene disclosed herein comprises a transition-metal atom sandwiched between ferrocene ring structures. In other embodiments, the Kaminsky catalyst can be represented by the formula $Cp_2MX_2$, where M is a transition metal (e.g., Zr, Ti or Hf); X is halogen (e.g., Cl), alkyl or a combination thereof; and Cp is a ferrocenyl group. In further embodiments, the Kaminsky catalyst has formula (XVI):

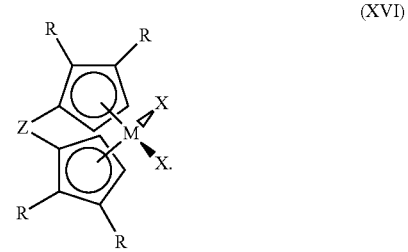

(XVI)

wherein Z is an optional divalent bridging group, usually $C(CH_3)_2$, $Si(CH_3)_2$, or $CH_2CH_2$; R is H or alkyl; M is a transition metal (e.g., Zr, Ti or Hf); X is halogen (e.g., Cl), alkyl or a combination thereof. Some non-limiting examples of Kaminsky catalysts have formulae (XVII) to (XIX):

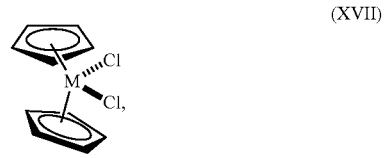

(XVII)

-continued (XVIII)

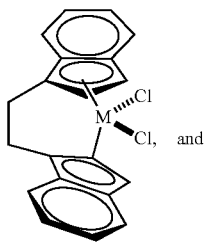

and (XIX)

wherein M is Zr, Hf or Ti.

In some embodiments, a cocatalyst is used with the Kaminsky catalyst. The cocatalyst may be any of the cocatalyst disclosed herein. In certain embodiments, the cocatalyst is methylaluminoxane (MAO). MAO is an oligomeric compound having a general formula $(CH_3AlO)_n$—, where n is from 1 to 10. MAO may play several roles: it alkylates the metallocene precursor by replacing chlorine atoms with methyl groups; it produces the catalytic active ion pair $Cp_2MCH_3^+/MAO^-$, where the cationic moiety is considered responsible for polymerization and $MAO^-$ acts as weakly coordinating anion. Some non-limiting examples of MAO include formulae (XX) to (XXI):

(XX)

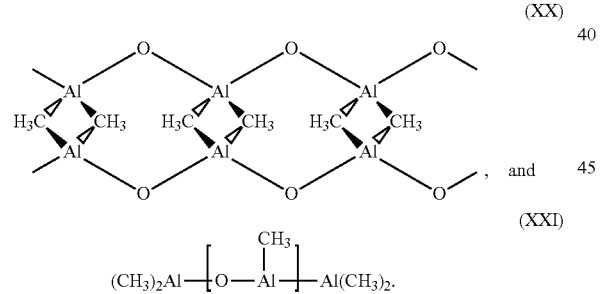

and (XXI)

$(CH_3)_2Al$—[$O$—$Al(CH_3)$]—$Al(CH_3)_2$.

In certain embodiments, the catalyst for making the farnesene interpolymer disclosed herein is or comprises a metallocene catalyst. Some metallocene catalysts are disclosed in Tae Oan Ahn et al., "*Modification of a Ziegler-Natta catalyst with a metallocene catalyst and its olefin polymerization behavior*," Polymer Engineering and Science, 39(7), p. 1257 (1999); and John Scheirs and Walter Kaminsky, "*Metallocene-Based Polyolefins: Preparation, Properties, and Technology*," Volume 1, Wiley (2000), both of which are incorporated herein by reference.

In other embodiments, the metallocene catalyst comprises complexes with a transition metal centre comprising a transition metal, such as Ni and Pd, and bulky, neutral ligands comprising alpha-diimine or diketimine. In further embodiments, the metallocene catalyst has formula (XXII):

(XXII)

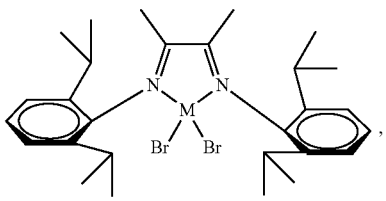

wherein M is Ni or Pd.

In some embodiments, the catalyst used herein is or comprises a metallocene catalyst bearing mono-anionic bidentate ligands. A non-limiting example of such a metallocene catalyst has structure (XXIII):

(XXIII)

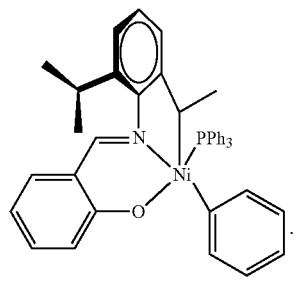

In other embodiments, the catalyst used herein is or comprises a metallocene catalyst comprising iron and a pyridyl is incorporated between two imine groups giving a tridentate ligand. A non-limiting example of such a metallocene catalyst has structure (XXIV):

(XXIV)

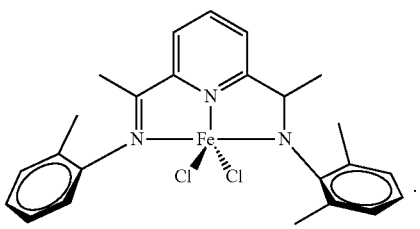

In some embodiments, the catalyst used herein is or comprises a metallocene catalyst comprising a salicylimine catalyst system based on zirconium. A non-limiting example of such a metallocene catalyst has structure (XXV):

(XXV)

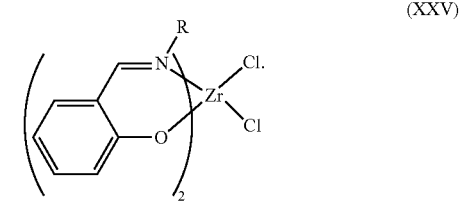

In some embodiments, the farnesene homopolymer disclosed herein is prepared by a process comprising the steps of:

(a) making a farnesene from a simple sugar or non-fermentable carbon source by using a microorganism; and (b) polymerizing the farnesene in the presence of a catalyst disclosed herein.

In certain embodiments, the farnesene interpolymer disclosed herein is prepared by a process comprising the steps of:

(a) making a farnesene from a simple sugar or non-fermentable carbon source by using a microorganism; and (b) copolymerizing the farnesene and at least one vinyl monomer in the presence of a catalyst disclosed herein.

In some embodiments, the polyfarnesene disclosed herein is prepared by polymerizing β-farnesene in the presence of a catalyst, wherein the amount of the cis-1,4-microstructure in the polyfarnesene is at most about 80 wt. %, at most about 75 wt. %, at most about 70 wt. %, at most about 65 wt. %, or at most about 60 wt. %, based on the total weight of the polyfarnesene. In some embodiments, the β-farnesene is copolymerized with a vinyl monomer to form a farnesene copolymer. In other embodiments, the vinyl monomer is styrene. In further embodiments, the farnesene copolymer is a block copolymer.

In certain embodiments, the polyfarnesene disclosed herein is prepared by polymerizing an α-farnesene in the presence of a catalyst. wherein the amount of the cis-1,4-microstructure in the polyfarnesene is from about 1 wt. % to about 99 wt. %, from about 10 wt. % to about 99 wt. %, from about 20 wt. % to about 99 wt. %, from about 30 wt. % to about 99 wt. %, from about 40 wt. % to about 99 wt. %, from about 50 wt. % to about 99 wt. %, from about 1 wt. % to about 99 wt. %, from about 1 wt. % to about 90 wt. %, from about 1 wt. % to about 80 wt. %, from about 1 wt. % to about 70 wt. %, or from about 1 wt. % to about 60 wt. %, based on the total weight of the polyfarnesene. In some embodiments, the α-farnesene is copolymerized with a vinyl monomer to form a farnesene copolymer. In other embodiments, the vinyl monomer is styrene. In further embodiments, the farnesene copolymer is a block copolymer.

In some embodiments, the polyfarnesene disclosed herein can be hydrogenated partially or completely by any hydrogenating agent known to a skilled artisan. For example, a saturated polyfarnesene can be prepared by (a) polymerizing a farnesene disclosed herein in the presence of a catalyst disclosed herein to form a polyfarnesene; and (b) hydrogenating at least a portion of the double bonds in the polyfarnesene in the presence of a hydrogenation reagent. In some embodiments, the farnesene is copolymerized with a vinyl monomer disclosed herein to form a farnesene copolymer. In other embodiments, the vinyl monomer is styrene. In further embodiments, the farnesene copolymer is a block copolymer. In still further embodiments, the farnesene is α-farnesene or β-farnesene or a combination thereof.

In certain embodiments, the hydrogenation reagent is hydrogen in the presence of a hydrogenation catalyst. In some embodiments, the hydrogenation catalyst is Pd, Pd/C, Pt, $PtO_2$, $Ru(PPh_3)_2Cl_2$, Raney nickel or a combination thereof. In one embodiment, the catalyst is a Pd catalyst. In another embodiment, the catalyst is 5% Pd/C. In a further embodiment, the catalyst is 10% Pd/C in a high pressure reaction vessel and the hydrogenation reaction is allowed to proceed until completion. Generally, after completion, the reaction mixture can be washed, concentrated, and dried to yield the corresponding hydrogenated product. Alternatively, any reducing agent that can reduce a C=C bond to a C—C bond can also be used. For example, the polyfarnesene can be hydrogenated by treatment with hydrazine in the presence of a catalyst, such as 5-ethyl-3-methyllumiflavinium perchlorate, under an oxygen atmosphere to give the corresponding hydrogenated products. The reduction reaction with hydrazine is disclosed in Imada et al., *J. Am. Chem. Soc.*, 127, 14544-14545 (2005), which is incorporated herein by reference.

In some embodiments, at least a portion of the C=C bonds of the polyfarnesene disclosed herein is reduced to the corresponding C—C bonds by hydrogenation in the presence of a catalyst and hydrogen at room temperature. In other embodiments, at least a portion of the C=C bonds of one or more of formulae (I')-(III'), (V')-(VII'), and (XI)-(XIV) and stereoisomers thereof is reduced to the corresponding C—C bonds by hydrogenation in the presence of a catalyst and hydrogen at room temperature. In further embodiments, the hydrogenation catalyst is 10% Pd/C.

In certain embodiments, the vinyl monomer is styrene. In some embodiments, the farnesene is α-farnesene or β-farnesene or a combination thereof. In other embodiments, the farnesene is prepared by using a microorganism. In further embodiments, the farnesene is derived from a simple sugar or non-fermentable carbon source.

Farnesene

The farnesene can be derived from any source or prepared by any method known to a skilled artisan. In some embodiments, the farnesene is derived from a chemical source (e.g., petroleum or coal) or obtained by a chemical synthetic method. In other embodiments, the farnesene is prepared by fractional distillation of petroleum or coal tar. In further embodiments, the farnesene is prepared by any known chemical synthetic method. One non-limiting example of suitable chemical synthetic method includes dehydrating nerolidol with phosphoryl chloride in pyridine as described in the article by Anet E. F. L. J., "*Synthesis of (E,Z)-α-,(Z,Z)-α-, and (Z)-β-farnesene*," *Aust. J. Chem.*, 23(10), 2101-2108 (1970), which is incorporated herein by reference.

In some embodiments, the farnesene can be obtained or derived from naturally occurring terpenes that can be produced by a wide variety of plants, such as *Copaifera langsdorfii*, conifers, and spurges; insects, such as swallowtail butterflies, leaf beetles, termites, and pine sawflies; and marine organisms, such as algae, sponges, corals, mollusks, and fish.

*Copaifera langsdorfii* or Copaifera tree is also known as the diesel tree and kerosene tree. It has many names in local languages, including kupa'y, cabismo, and copaúva. Copaifera tree may produce a large amount of terpene hydrocarbons in its wood and leaves. Generally, one Copaifera tree can produce from about 30 to about 40 liters of terpene oil per year.

Terpene oils can also be obtained from conifers and spurges. Conifers belong to the plant division Pinophyta or Coniferae and are generally cone-bearing seed plants with vascular tissue. The majority of conifers are trees, but some conifers can be shrubs. Some non-limiting examples of suitable conifers include cedars, cypresses, douglas-firs, firs, junipers, kauris, larches, pines, redwoods, spruces, and yews. Spurges, also known as *Euphorbia*, are a very diverse worldwide genus of plants, belonging to the spurge family (Euphorbiaceae). Consisting of about 2160 species, spurges are one of the largest genera in the plant kingdom.

The farnesene is a sesquiterpene which are part of a larger class of compound called terpenes. A large and varied class of hydrocarbons, terpenes include hemiterpenes, monoterpenes, sesquiterpenes, diterpenes, sesterterpenes, triterpenes, tetraterpenes, and polyterpenes. As a result, the farnesene can be isolated or derived from terpene oils for use in the present invention.

In certain embodiments, the farnesene is derived from a biological source. In other embodiments, the farnesene can be obtained from a readily available, renewable carbon source. In further embodiments, the farnesene is prepared by contacting a cell capable of making a farnesene with a carbon source under conditions suitable for making the farnesene.

Any carbon source that can be converted into one or more isoprenoid compounds can be used herein. In some embodiments, the carbon source is a sugar or a non-fermentable carbon source. The sugar can be any sugar known to those of skill in the art. In certain embodiments, the sugar is a monosaccharide, disaccharide, polysaccharide or a combination thereof. In other embodiments, the sugar is a simple sugar (a monosaccharide or a disaccharide). Some non-limiting examples of suitable monosaccharides include glucose, galactose, mannose, fructose, ribose and combinations thereof. Some non-limiting examples of suitable disaccharides include sucrose, lactose, maltose, trehalose, cellobiose and combinations thereof. In still other embodiments, the simple sugar is sucrose. In certain embodiments, the bioengineered fuel component can be obtained from a polysaccharide. Some non-limiting examples of suitable polysaccharides include starch, glycogen, cellulose, chitin and combinations thereof.

The sugar suitable for making the farnesene can be found in a wide variety of crops or sources. Some non-limiting examples of suitable crops or sources include sugar cane, bagasse, *miscanthus*, sugar beet, sorghum, grain sorghum, switchgrass, barley, hemp, kenaf, potatoes, sweet potatoes, cassava, sunflower, fruit, molasses, whey or skim milk, corn, stover, grain, wheat, wood, paper, straw, cotton, many types of cellulose waste, and other biomass. In certain embodiments, the suitable crops or sources include sugar cane, sugar beet and corn. In other embodiments, the sugar source is cane juice or molasses.

A non-fermentable carbon source is a carbon source that cannot be converted by the organism into ethanol. Some non-limiting examples of suitable non-fermentable carbon sources include acetate and glycerol.

In certain embodiments, the farnesene can be prepared in a facility capable of biological manufacture of $C_{15}$ isoprenoids. The facility can comprise any structure useful for preparing the $C_{15}$ isoprenoids, such as α-farnesene, β-farnesene, nerolidol or farnesol, using a microorganism. In some embodiments, the biological facility comprises one or more of the cells disclosed herein. In other embodiments, the biological facility comprises a cell culture comprising at least a $C_{15}$ isoprenoid in an amount of at least about 1 wt. %, at least about 5 wt. %, at least about 10 wt. %, at least about 20 wt. %, or at least about 30 wt. %, based on the total weight of the cell culture. In further embodiments, the biological facility comprises a fermentor comprising one or more cells described herein.

Any fermentor that can provide cells or bacteria a stable and optimal environment in which they can grow or reproduce can be used herein. In some embodiments, the fermentor comprises a culture comprising one or more of the cells disclosed herein. In other embodiments, the fermentor comprises a cell culture capable of biologically manufacturing farnesyl pyrophosphate (FPP). In further embodiments, the fermentor comprises a cell culture capable of biologically manufacturing isopentenyl diphosphate (IPP). In certain embodiments, the fermentor comprises a cell culture comprising at least a $C_{15}$ isoprenoid in an amount of at least about 1 wt. %, at least about 5 wt. %, at least about 10 wt. %, at least about 20 wt. %, or at least about 30 wt. %, based on the total weight of the cell culture.

The facility can further comprise any structure capable of manufacturing the fuel component or fuel additive from the $C_{15}$ isoprenoid, such as α-farnesene, β-farnesene, nerolidol or farnesol. The structure may comprise a reactor for dehydrating the nerolidol or farnesol to α-farnesene or β-farnesene. Any reactor that can be used to convert an alcohol into an alkene under conditions known to skilled artisans may be used herein. The reactor may comprise a dehydrating catalyst disclosed herein. In some embodiments, the structure further comprises a mixer, a container, and a mixture of the dehydrating products from the dehydrating step.

The biosynthetic process of making $C_{15}$ isoprenoid compounds are disclosed in U.S. Pat. No. 7,399,323; U.S. Application Number US 2008/0274523; and PCT Publication Numbers WO 2007/140339 and WO 2007/139924, which are incorporated herein by reference.

α-Farnesene
α-Farnesene, whose structure is

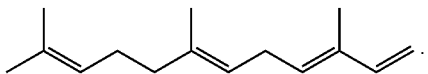

is found in various biological sources including, but not limited to, the Dufour's gland in ants and in the coating of apple and pear peels. Biochemically, α-farnesene is made from FPP by α-farnesene synthase. Some non-limiting examples of suitable nucleotide sequences that encode such an enzyme include (DQ309034; *Pyrus communis* cultivar d'Anjou) and (AY182241; *Malus domestica*). See Pechouus et al., *Planta* 219(1):84-94 (2004).

β-Farnesene
β-Farnesene, whose structure is

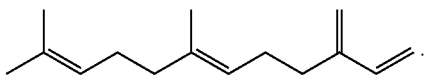

is found in various biological sources including, but not limited to, aphids and essential oils such as peppermint oil. In some plants such as wild potato, β-farnesene is synthesized as a natural insect repellent. Biochemically, β-farnesene is made from FPP by β-farnesene synthase. Some non-limiting examples of suitable nucleotide sequences that encode such an enzyme include (AF024615; *Menthaxpiperita*) and (AY835398; *Artemisia annua*). See Picaud et al., *Phytochemistry* 66(9): 961-967 (2005).

Farnesol
Farnesol, whose structure is

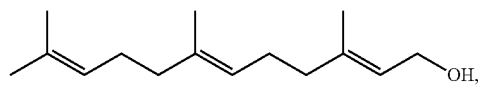

is found in various biological sources including insects and essential oils from citronella, neroli, cyclamen, lemon grass, tuberose, and rose. Biochemically, farnesol is made from FPP by a hydroxylase such as farnesol synthase. Some non-limiting examples of suitable nucleotide sequences that encode such an enzyme include (AF529266; *Zea mays*) and (YDR481C; *Saccharomyces cerevisiae*). See Song, L., *Applied Biochemistry and Biotechnology* 128:149-158 (2006).

Nerolidol

Nerolidol, whose structure is

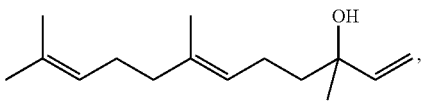

is also known as peruviol which is found in various biological sources including essential oils from neroli, ginger, jasmine, lavender, tea tree, and lemon grass. Biochemically, nerolidol is made from FPP by a hydroxylase such as nerolidol synthase. A non-limiting example of a suitable nucleotide sequence that encodes such an enzyme includes AF529266 from *Zea mays* (maize; gene tps1).

The farnesol and nerolidol disclosed herein may be converted into α-farnesene, β-farnesene or a combination thereof by dehydration with a dehydrating agent or an acid catalyst. Any dehydrating agent or an acid catalyst that can convert an alcohol into an alkene can be used herein. Some non-limiting examples of suitable dehydrating agents or acid catalysts include phosphoryl chloride, anhydrous zinc chloride, phosphoric acid and sulfuric acid.

General Procedures of Making Polyfarnesenes

The polymerization of a farnesene or the copolymerization of a farnesene with a vinyl comonomer can be performed over a wide temperature range. In certain embodiments, the polymerization temperature is from about −30° C. to about 280° C., from about 30° C. to about 180° C., or from about 60° C. to about 100° C. The partial pressures of the vinyl comonomers can range from about 15 psig (0.1 MPa) to about 50,000 psig (245 MPa), from about 15 psig (0.1 MPa) to about 25,000 psig (172.5 MPa), from about 15 psig (0.1 MPa) to about 10,000 psig (69 MPa), from about 15 psig (0.1 MPa) to about 5,000 psig (34.5 MPa) or from about 15 psig (0.1 MPa) to about 1,000 psig (6.9 MPa).

The concentration of the catalyst used for making the polyfarnesenes disclosed herein depends on many factors. In some embodiment, the concentration ranges from about 0.01 micromoles per liter to about 100 micromoles per liter. The polymerization time depends on the type of process, the catalyst concentration, and other factors. Generally, the polymerization time is within several minutes to several hours.

A non-limiting example of solution polymerization procedure for farnesene homopolymer is outlined below. A farnesene such as β-farnesene can be added to a solvent such as cyclohexane to form a solution in a reactor which may be optionally under a nitrogen or argon atmosphere. The solution can be dried over a drying agent such as molecular sieves. A catalyst such as organolithium reagent can be added into the reactor, and then the reactor is heated to an elevated temperature until all or a substantial portion of farnesene is consumed. The farnesene homopolymer can then be precipitated from the reaction mixture and dried in a vacuum oven.

A non-limiting example of solution polymerization procedure for farnesene interpolymer is outlined below. A farnesene such as β-farnesene can be added to a solvent such as cyclohexane to form a farnesene solution in a reactor optionally under a nitrogen or argon atmosphere. The farnesene solution can be dried over a drying agent such as molecular sieves. In a second reactor optionally under nitrogen or argon atmosphere, a solution of styrene in cyclohexane with 10% is similarly prepared and dried over a drying agent such as molecular sieves. The styrene is polymerized by a catalyst such as organolithium reagent at an elevated temperature until all or a substantial portion of styrene is consumed. Then, the farnesene solution is transferred to the second reactor. The reaction is allowed to react until all or a substantial portion of farnesene is consumed. Then a dichlorosilane coupling agent (e.g., dichlorodimethylsilane in 1,2-dichloroethane) is then added into the second reactor to form a farnesene interpolymer.

Polyfarnesene Compositions

The polyfarnesene disclosed herein can be used to prepare useful compositions or polyfarnesene compositions such as adhesives compositions. In some embodiments, the polyfarnesene compositions comprise the polyfarnesene and an optional tackifier. In other embodiments, the polyfarnesene compositions comprise the polyfarnesene and an optional second polymer. In further embodiments, the polyfarnesene compositions comprise the polyfarnesene and a tackifier. In still further embodiments, the polyfarnesene compositions comprise the polyfarnesene, a tackifier and a second polymer. In certain embodiments, the polyfarnesene compositions do not comprise a tackifier or second polymer.

The second polymer can be a vinyl polymer or copolymer, a non-vinyl polymer or copolymer, or a combination thereof. Some non-limiting examples of vinyl polymers and copolymers are disclosed in Malcolm P. Stevens, "*Polymer Chemistry, an Introduction*," Third Edition, Oxford University Press, pp. 17-21 and 167-279 (1999), which is incorporated herein by reference. Some non-limiting examples of suitable second polymer include a polyolefin, polyurethane, polyester, polyamide, styrenic polymer, phenolic resin, polyacrylate, polymethacrylate or a combination thereof.

In certain embodiments, the ratio of the farnesene interpolymer to the second polymer is from about 1:99 to about 99:1, from about 1:50 to about 50:1, from about 1:25 to about 25:1 or from about 1:10 to about 10:1.

In some embodiments, the second polymer is a polyolefin (e.g., polyethylene, polypropylene, an ethylene/α-olefin interpolymer, a copolymer of ethylene and propylene, and a copolymer of ethylene and vinyl acetate (EVA)), polyurethane, polyester, polyamide, styrenic polymer (e.g., polystyrene, poly(acrylonitrile-butadiene-styrene), poly(styrene-butadiene-styrene) and the like), phenolic resin, polyacrylate, polymethacrylate or a combination thereof. In some embodiments, the second polymer is polyethylene, polypropylene, polystyrene, a copolymer of ethylene and vinyl acetate, poly(acrylonitrile-butadiene-styrene), poly(styrene-butadiene-styrene) or a combination thereof. The second polymer may be blended with the farnesene interpolymer before it is added to the polyfarnesene composition. In some embodiments, the second polymer is added directly to the polyfarnesene composition without pre-blending with the farnesene interpolymer.

The weight ratio of the polyfarnesene to the second polymer, such as EVA, in the polyfarnesene composition can be between about 1:99 and about 99:1, between about 1:50 and about 50:1, between about 1:25 and about 25:1, between about 1:10 and about 10:1, between about 1:9 and about 9:1, between about 1:8 and about 8:1, between about 1:7 and about 7:1, between about 1:6 and about 6:1, between about 1:5 and about 5:1, between about 1:4 and about 4:1, between about 1:3 and about 3:1, between about 1:2 and about 2:1, between about 3:7 and about 7:3 or between about 2:3 and about 3:2.

In some embodiments, the second polymer is a polyolefin. Any polyolefin that is partially or totally compatible with the farnesene interpolymer may be used. Non-limiting examples of suitable polyolefins include polyethylenes; polypropylenes; polybutylenes (e.g., polybutene-1); polypentene-1; polyhexene-1; polyoctene-1; polydecene-1; poly-3-methylbutene-1; poly-4-methylpentene-1; polyisoprene; polybutadiene; poly-1,5-hexadiene; interpolymers derived from olefins; interpolymers derived from olefins and other polymers such as polyvinyl chloride, polystyrene, polyurethane, and the like; and mixtures thereof. In some embodiments, the polyolefin is a homopolymer such as polyethylene, polypropylene, polybutylene, polypentene-1, poly-3-methylbutene-1, poly-4-methylpentene-1, polyisoprene, polybutadiene, poly-1,5-hexadiene, polyhexene-1, polyoctene-1 and polydecene-1.

Some non-limiting examples of suitable polyethylenes include ultra low density polyethylene (ULDPE), linear low density polyethylene (LLDPE), low density polyethylene (LDPE), medium density polyethylene (MDPE), high density polyethylene (HDPE), high molecular weight high density polyethylene (HMW-HDPE), ultra high molecular weight polyethylene (UHMW-PE) and combinations thereof. Some non-limiting examples of polypropylenes include low density polypropylene (LDPP), high density polypropylene (HDPP), high-melt strength polypropylene (HMS-PP) and combination thereof. In some embodiments, the second polymer is or comprises high-melt-strength polypropylene (HMS-PP), low density polyethylene (LDPE) or a combination thereof.

Any material that can be added to an elastomer to produce an adhesive can be used herein as a tackifier. Some non-limiting examples of tackifiers include a natural and modified resin; a glycerol or pentaerythritol ester of natural or modified rosin; a copolymer or terpolymer of natured terpene; a polyterpene resin or a hydrogenated polyterpene resin; a phenolic modified terpene resin or a hydrogenated derivative thereof; an aliphatic or cycloaliphatic hydrocarbon resin or a hydrogenated derivative thereof; an aromatic hydrocarbon resin or a hydrogenated derivative thereof; an aromatic modified aliphatic or cycloaliphatic hydrocarbon resin or a hydrogenated derivative thereof; or a combination thereof. In certain embodiments, the tackifier has a ring and ball (R&B) softening point equal to or greater than 60° C., 70° C., 75° C., 80° C., 85° C., 90° C. or 100° C., as measured in accordance with ASTM 28-67, which is incorporated herein by reference. In certain embodiments, the tackifier has a R&B softening point equal to or greater than 80° C., as measured in accordance with ASTM 28-67.

In certain embodiments, the amount of tackifier in the compositions disclosed herein is from about 0.1 wt. % to about 70 wt. %, from about 0.1 wt. % to about 60 wt. %, from about 1 wt. % to about 50 wt. %, or from about 0.1 wt. % to about 40 wt. % or from about 0.1 wt. % to about 30 wt. % or from about 0.1 wt. % to about 20 wt. %, or from about 0.1 wt. % to about 10 wt. %, based on the total weight of the composition. In other embodiments, the amount of tackifier in the compositions disclosed herein is from about 1 wt. % to about 70 wt. %, from about 5 wt. % to about 70 wt. %, from about 10 wt. % to about 70 wt. %, from about 15 wt. % to about 70 wt. %, from about 20 wt. % to about 70 wt. %, or from about 25 wt. % to about 70 wt. %, based on the total weight of the composition.

Optionally, the compositions disclosed herein comprise at least another additive for the purposes of improving and/or controlling the processability, appearance, physical, chemical, and/or mechanical properties of the polyfarnesene compositions. In some embodiments, the compositions do not comprise an additive. Any plastics additive known to a person of ordinary skill in the art may be used in the compositions disclosed herein. Non-limiting examples of suitable additives include plasticizers, oils, waxes, antioxidants, UV stabilizers, colorants or pigments, fillers, flow aids, coupling agents, crosslinking agents, surfactants, solvents, and combinations thereof. In certain embodiments, the additive is plasticizer, such as a mineral oil, liquid polybutene or a combination thereof.

The total amount of the additives can range from about greater than 0 to about 80%, from about 0.001% to about 70%, from about 0.01% to about 60%, from about 0.1% to about 50%, from about 1% to about 40%, or from about 10% to about 50% of the total weight of the polyfarnesene composition. The amount of each of the additives can range from about greater than 0 to about 25%, from about 0.001% to about 20%, from about 0.01% to about 15%, from about 0.1% to about 10%, from about 0.1% to about 5%, or from about 0.1% to about 2.5% of the total weight of the polyfarnesene composition. Some polymer additives have been described in Zweifel Hans et al., "*Plastics Additives Handbook*," Hanser Gardner Publications, Cincinnati, Ohio, 5th edition (2001), which is incorporated herein by reference in its entirety.

Optionally, the compositions disclosed herein can comprise a wax, such as a petroleum wax, a low molecular weight polyethylene or polypropylene, a synthetic wax, a polyolefin wax, a beeswax, a vegetable wax, a soy wax, a palm wax, a candle wax or an ethylene/α-olefin interpolymer having a melting point of greater than 25° C. In certain embodiments, the wax is a low molecular weight polyethylene or polypropylene having a number average molecular weight of about 400 to about 6,000 g/mole. The wax can be present from about 10% to about 50% or 20% to about 40% by weight of the total composition.

Optionally, the compositions disclosed herein can comprise a plasticizer. In general, a plasticizer is a chemical that can increase the flexibility and lower the glass transition temperature of polymers. Any plasticizer known to a person of ordinary skill in the art may be added to the polyfarnesene compositions disclosed herein. Non-limiting examples of plasticizers include mineral oils, abietates, adipates, alkyl sulfonates, azelates, benzoates, chlorinated paraffins, citrates, epoxides, glycol ethers and their esters, glutarates, hydrocarbon oils, isobutyrates, oleates, pentaerythritol derivatives, phosphates, phthalates, esters, polybutenes, ricinoleates, sebacates, sulfonamides, tri- and pyromellitates, biphenyl derivatives, stearates, difuran diesters, fluorine-containing plasticizers, hydroxybenzoic acid esters, isocyanate adducts, multi-ring aromatic compounds, natural product derivatives, nitriles, siloxane-based plasticizers, tar-based products, thioesters and combinations thereof. Where used, the amount of the plasticizer in the polyfarnesene composition can be from greater than 0 to about 15 wt. %, from about 0.5 wt. % to about 10 wt. %, or from about 1 wt. % to about 5 wt. % of the total weight of the polyfarnesene composition. Some plasticizers have been described in George Wypych, "*Handbook of Plasticizers*," ChemTec Publishing, Toronto-Scarborough, Ontario (2004), which is incorporated herein by reference.

In some embodiments, the compositions disclosed herein optionally comprise an antioxidant that can prevent the oxidation of polymer components and organic additives in the polyfarnesene compositions. Any antioxidant known to a person of ordinary skill in the art may be added to the polyfarnesene compositions disclosed herein. Non-limiting examples of suitable antioxidants include aromatic or hindered amines such as alkyl diphenylamines, phenyl-α-naphthylamine, alkyl or aralkyl substituted phenyl-α-naphthylamine, alkylated p-phenylene diamines, tetramethyl-diaminodiphenylamine and the like; phenols such as 2,6-di-t-butyl-4-methylphenol; 1,3,5-trimethyl-2,4,6-tris(3',5'-di-t-butyl-4'-hydroxybenzyl)benzene; tetrakis[(methylene(3,5-di-t-butyl-4-hydroxyhydrocinnamate)]methane (e.g., IRGANOX™1010, from Ciba Geigy, New York); acryloyl modified phenols; octadecyl-3,5-di-t-butyl-4-hydroxycinnamate (e.g., IRGANOX™ 1076, commercially available from Ciba Geigy); phosphites and phosphonites; hydroxylamines; benzofuranone derivatives; and combinations thereof. Where used, the amount of the antioxidant in the polyfarnesene composition can be from about greater than 0 to about 5 wt. %, from about 0.0001 to about 2.5 wt. %, from about 0.001 wt. % to about 1 wt. %, or from about 0.001 wt. % to about 0.5 wt. % of the total weight of the polyfarnesene composition. Some antioxidants have been described in Zweifel Hans et al., "*Plastics Additives Handbook*," Hanser Gardner Publications, Cincinnati, Ohio, 5th edition, Chapter 1, pages 1-140 (2001), which is incorporated herein by reference.

In other embodiments, the compositions disclosed herein optionally comprise an UV stabilizer that may prevent or reduce the degradation of the polyfarnesene compositions by UV radiations. Any UV stabilizer known to a person of ordinary skill in the art may be added to the polyfarnesene compositions disclosed herein. Non-limiting examples of suitable UV stabilizers include benzophenones, benzotriazoles, aryl esters, oxanilides, acrylic esters, formamidines, carbon black, hindered amines, nickel quenchers, hindered amines, phenolic antioxidants, metallic salts, zinc compounds and combinations thereof. Where used, the amount of the UV stabilizer in the polyfarnesene composition can be from about greater than 0 to about 5 wt. %, from about 0.01 wt. % to about 3 wt. %, from about 0.1 wt. % to about 2 wt. %, or from about 0.1 wt. % to about 1 wt. % of the total weight of the polyfarnesene composition. Some UV stabilizers have been described in Zweifel Hans et al., "*Plastics Additives Handbook*," Hanser Gardner Publications, Cincinnati, Ohio, 5th edition, Chapter 2, pages 141-426 (2001), which is incorporated herein by reference.

In further embodiments, the compositions disclosed herein optionally comprise a colorant or pigment that can change the look of the polyfarnesene compositions to human eyes. Any colorant or pigment known to a person of ordinary skill in the art may be added to the polyfarnesene compositions disclosed herein. Non-limiting examples of suitable colorants or pigments include inorganic pigments such as metal oxides such as iron oxide, zinc oxide, and titanium dioxide, mixed metal oxides, carbon black, organic pigments such as anthraquinones, anthanthrones, azo and monoazo compounds, arylamides, benzimidazolones, BONA lakes, diketopyrrolo-pyrroles, dioxazines, disazo compounds, diarylide compounds, flavanthrones, indanthrones, isoindolinones, isoindolines, metal complexes, monoazo salts, naphthols, b-naphthols, naphthol AS, naphthol lakes, perylenes, perinones, phthalocyanines, pyranthrones, quinacridones, and quinophthalones, and combinations thereof. Where used, the amount of the colorant or pigment in the polyfarnesene composition can be from about greater than 0 to about 10 wt. %, from about 0.1 wt. % to about 5 wt. %, or from about 0.25 wt. % to about 2 wt. % of the total weight of the polyfarnesene composition. Some colorants have been described in Zweifel Hans et al., "*Plastics Additives Handbook*," Hanser Gardner Publications, Cincinnati, Ohio, 5th edition, Chapter 15, pages 813-882 (2001), which is incorporated herein by reference.

Optionally, the compositions disclosed herein can comprise a filler which can be used to adjust, inter alia, volume, weight, costs, and/or technical performance. Any filler known to a person of ordinary skill in the art may be added to the polyfarnesene compositions disclosed herein. Non-limiting examples of suitable fillers include talc, calcium carbonate, chalk, calcium sulfate, clay, kaolin, silica, glass, fumed silica, mica, wollastonite, feldspar, aluminum silicate, calcium silicate, alumina, hydrated alumina such as alumina trihydrate, glass microsphere, ceramic microsphere, thermoplastic microsphere, barite, wood flour, glass fibers, carbon fibers, marble dust, cement dust, magnesium oxide, magnesium hydroxide, antimony oxide, zinc oxide, barium sulfate, titanium dioxide, titanates and combinations thereof. In some embodiments, the filler is barium sulfate, talc, calcium carbonate, silica, glass, glass fiber, alumina, titanium dioxide, or a mixture thereof. In other embodiments, the filler is talc, calcium carbonate, barium sulfate, glass fiber or a mixture thereof. Where used, the amount of the filler in the polyfarnesene composition can be from about greater than 0 to about 80 wt. %, from about 0.1 wt. % to about 60 wt. %, from about 0.5 wt. % to about 40 wt. %, from about 1 wt. % to about 30 wt. %, or from about 10 wt. % to about 40 wt. % of the total weight of the polyfarnesene composition. Some fillers have been disclosed in U.S. Pat. No. 6,103,803 and Zweifel Hans et al., "*Plastics Additives Handbook*," Hanser Gardner Publications, Cincinnati, Ohio, 5th edition, Chapter 17, pages 901-948 (2001), both of which are incorporated herein by reference.

Optionally, the polyfarnesene compositions disclosed herein may be crosslinked, partially or completely. When crosslinking is desired, the polyfarnesene compositions disclosed herein comprise a cross-linking agent that can be used to effect the cross-linking of the polyfarnesene compositions, thereby increasing their modulus and stiffness, among other things. An advantage of a polyfarnesene composition is that crosslinking can occur in its side chains instead of the polymer backbone like other polymers such as polyisoprene and polybutadiene. Any cross-linking agent known to a person of ordinary skill in the art may be added to the polyfarnesene compositions disclosed herein. Non-limiting examples of suitable cross-linking agents include organic peroxides (e.g., alkyl peroxides, aryl peroxides, peroxyesters, peroxycarbonates, diacylperoxides, peroxyketals, and cyclic peroxides) and silanes (e.g., vinyltrimethoxysilane, vinyltriethoxysilane, vinyltris(2-methoxyethoxy)silane, vinyltriacetoxysilane, vinylmethyldimethoxysilane, and 3-methacryloyloxypropyltrimethoxysilane). Where used, the amount of the cross-linking agent in the polymer composition can be from about greater than 0 to about 20 wt. %, from about 0.1 wt. % to about 15 wt. %, or from about 1 wt. % to about 10 wt. % of the total weight of the polymer composition. Some suitable cross-linking agents have been disclosed in Zweifel Hans et al., "*Plastics Additives Handbook*," Hanser Gardner Publications, Cincinnati, Ohio, 5th edition, Chapter 14, pages 725-812 (2001), both of which are incorporated herein by reference.

In some embodiments, the farnesene interpolymers disclosed herein includes farnesene-modified polymers prepared by copolymerizing one or more farnesene with one or more vinyl monomers. In certain embodiments, the unmodified polymer derived from the one or more vinyl monomers can be any known olefin homopolymer or interpolymer. In further embodiments, none of the one or more other vinyl monomers has an unsaturated side chain capable of reacting with a cross-linking agent. Because of the unsaturated side chains derived from the farnesene, the farnesene-modified polymer disclosed herein can be cross-linked by a cross-linking agent disclosed herein.

In certain embodiments, the amount of the farnesene in the farnesene-modified polymer disclosed herein is from about 1 wt. % to about 20 wt. %, from about 1 wt. % to about 10 wt. %, from about 1 wt. % to about 7.5 wt. %, from about 1 wt. % to about 5 wt. %, from about 1 wt. % to about 4 wt. %, from about 1 wt. % to about 3 wt. %, or from about 1 wt. % to about 2 wt. %, based on the total weight of the farnesene-modified polymer. In other embodiments, the amount of the one or more other vinyl monomers in the farnesene-modified polymer disclosed herein is from about 80 wt. % to about 99 wt. %, from about 90 wt. % to about 99 wt. %, from about 92.5 wt. % to about 99 wt. %, from about 95 wt. % to about 99 wt. %, from about 96 wt. % to about 99 wt. %, from about 97 wt. % to about 99 wt. %, or from about 98 wt. % to about 99 wt. %, based on the total weight of the farnesene-modified polymer.

The cross-linking of the polyfarnesene compositions can also be initiated by any radiation means known in the art, including, but not limited to, electron-beam irradiation, beta irradiation, gamma irradiation, corona irradiation, and UV radiation with or without cross-linking catalyst. U.S. patent application Ser. No. 10/086,057 (published as US2002/0132923 A1) and U.S. Pat. No. 6,803,014 disclose electron-beam irradiation methods that can be used in embodiments of the invention.

Irradiation may be accomplished by the use of high energy, ionizing electrons, ultra violet rays, X-rays, gamma rays, beta particles and the like and combination thereof. Preferably, electrons are employed up to 70 megarads dosages. The irradiation source can be any electron beam generator operating in a range of about 150 kilovolts to about 6 megavolts with a power output capable of supplying the desired dosage. The voltage can be adjusted to appropriate levels which may be, for example, 100,000, 300,000, 1,000,000 or 2,000,000 or 3,000,000 or 6,000,000 or higher or lower. Many other apparati for irradiating polymeric materials are known in the art. The irradiation is usually carried out at a dosage between about 3 megarads to about 35 megarads, preferably between about 8 to about 20 megarads. Further, the irradiation can be carried out conveniently at room temperature, although higher and lower temperatures, for example, 0° C. to about 60° C., may also be employed. Preferably, the irradiation is carried out after shaping or fabrication of the article. Also, in a preferred embodiment, the farnesene interpolymer which has been incorporated with a pro-rad additive is irradiated with electron beam radiation at about 8 to about 20 megarads.

Crosslinking can be promoted with a crosslinking catalyst, and any catalyst that will provide this function can be used. Suitable catalysts generally include organic bases; carboxylic acids; organometallic compounds including organic titanates and complexes or carboxylates of lead, cobalt, iron, nickel, zinc and tin; dibutyltindilaurate, dioctyltinmaleate, dibutyltindiacetate, dibutyltindioctoate, stannous acetate, stannous octoate, lead naphthenate, zinc caprylate, cobalt naphthenate; and the like. The catalyst (or mixture of catalysts) is present in a catalytic amount, typically between about 0.015 and about 0.035 phr.

Blending of the Ingredients of the Polyfarnesene Compositions

The ingredients (i.e., the polyfarnesene, the optional second polymer and additives) of the polyfarnesene compositions disclosed herein, can be mixed or blended using methods known to a person of ordinary skill in the art. Non-limiting examples of suitable blending methods include melt blending, solvent blending, extruding, and the like.

In some embodiments, the ingredients of the compositions disclosed herein are melt blended by a method as described by Guerin et al. in U.S. Pat. No. 4,152,189. First, all solvents, if there are any, are removed from the ingredients by heating to an appropriate elevated temperature of about 100° C. to about 200° C. or about 150° C. to about 175° C. at a pressure of about 5 ton (667 Pa) to about 10 ton (1333 Pa). Next, the ingredients are weighed into a vessel in the desired proportions and the foam is formed by heating the contents of the vessel to a molten state while stirring.

In other embodiments, the ingredients of the compositions disclosed herein are processed using solvent blending. First, the ingredients are dissolved in a suitable solvent and the mixture is then mixed or blended. Next, the solvent is removed to provide the compositions disclosed herein.

In further embodiments, physical blending devices that can provide dispersive mixing, distributive mixing, or a combination of dispersive and distributive mixing can be used in preparing homogenous blends. Both batch and continuous methods of physical blending can be used. Non-limiting examples of batch methods include those methods using BRABENDER® mixing equipments (e.g., BRABENDER PREP CENTER®, available from C. W. Brabender Instruments, Inc., South Hackensack, N.J.) or BANBURY® internal mixing and roll milling (available from Farrel Company, Ansonia, Conn.) equipment. Non-limiting examples of continuous methods include single screw extruding, twin screw extruding, disk extruding, reciprocating single screw extruding, and pin barrel single screw extruding. In some embodiments, the additives can be added into an extruder through a feed hopper or feed throat during the extrusion of the farnesene interpolymer, the optional second polymer or the foam. The mixing or blending of polymers by extrusion has been described in C. Rauwendaal, "*Polymer Extrusion*", Hanser Publishers, New York, N.Y., pages 322-334 (1986), which is incorporated herein by reference.

When one or more additives are required in the compositions disclosed herein, the desired amounts of the additives can be added in one charge or multiple charges to the polyfarnesene, the second polymer or the composition. Furthermore, the addition can take place in any order. In some embodiments, the additives are first added and mixed or blended with the polyfarnesene and then the additive-containing polyfarnesene is blended with the second polymer. In other embodiments, the additives are first added and mixed or blended with the second polymer and then the additive-containing second polymer is blended with the polyfarnesene. In further embodiments, the polyfarnesene is blended with the second polymer first and then the additives are blended with the composition.

The ingredients of the composition disclosed herein can be mixed or blended in any suitable mixing or blending devices known to skilled artisans. The ingredients in the composition disclosed herein can then be mixed at a temperature below the decomposition temperature of the ingredients to ensure that all ingredients are homogeneously mixed and remain intact.

Applications of the Compositions Comprising the Polyfarnesenes

The polyfarnesene compositions disclosed herein can be used as hot melt adhesives or pressure sensitive adhesives. It can be applied to manufacture any article that requires or comprises a hot melt adhesive or a pressure sensitive adhesive. Non-limiting examples of suitable articles include paper products, packaging materials, laminated wood panels, kitchen countertops, vehicles, labels, disposable diapers, hospital pads, feminine sanitary napkins, surgical drapes, tapes, cases, cartons, trays, medical devices, and bandages. In a further embodiment, the adhesive composition can be used in tapes, cases, cartons, trays, medical devices, and bandages.

In some embodiments, the compositions disclosed herein are used as hot melt adhesives. Such hot melt adhesive compositions can be used in industrial applications including packaging, particularly for low temperature use such as for dairy products or for freezer packaging of food products, and in sanitary disposable consumer articles, for example, diapers, feminine care pads, napkins, and the like. Some other suitable applications include book-binding, wood working and labeling. Some hot melt adhesives are described in A. V. Pocius, "*Adhesion and Adhesives Technology*," Hanser Gardner Publications; 2nd edition, Chapter 10, pp. 270-280 (2002), and M. J Satriana, "*Hot melt adhesives: Manufacture and applications*," Noyes Data Corp (1974), both of which are incorporated herein as reference.

In other embodiments, the compositions disclosed herein may be used as PSAs. Such PSA adhesive compositions can be applied to sheeting products (e.g., decorative, reflective, and graphical), labelstock, and tape backings. The substrate can be any suitable type of material depending on the desired application. In certain embodiments, the substrate comprises a nonwoven, paper, polymeric film (e.g., polypropylene (e.g., biaxially oriented polypropylene (BOPP)), polyethylene, polyurea, or polyester (e.g., polyethylene terephthalate (PET)), or release liner (e.g., siliconized liner). Some PSAs are described in A. V. Pocius, "*Adhesion and Adhesives Technology*," Hanser Gardner Publications; 2nd edition, Chapter 9, pp. 238-259 (2002); and Istvan Benedek, "*Technology of Pressure-Sensitive Adhesives and Products*," CRC; (2008), both of which are incorporated herein as reference.

In still other embodiments, the compositions can be utilized to form tape. For example, the PSA or hot melt adhesive composition is applied to at least one side of the backing of the tape. The adhesive composition may then be crosslinked to further improve its shear strength. Any suitable crosslinking method (e.g., exposure to radiation, such as ultraviolet or electron beam) or crosslinker additive (e.g., phenolic and silane curatives) may be utilized.

The adhesive compositions disclosed herein may be applied to the desired substrate or adhered in any manner known in the art, particularly those methods used traditionally for making tapes, cases, cartons, trays, medical devices, and bandages. In other embodiments, the adhesive compositions can be applied by a coating head or nozzle, with associated equipment. The adhesive compositions can be applied as fine lines, dots or spray coatings, in addition to other traditional forms as desired.

In some embodiments, the adhesive compositions can be applied using melt extrusion techniques. The adhesive composition can be applied by either continuous or batch processes. An example of a batch process is the placement of a portion of the adhesive composition between a substrate to which the adhesive composition is to be adhered and a surface capable of releasing the adhesive to form a composite structure. An example of a continuous forming method includes drawing the adhesive composition out of a heated film die and subsequently contacting the drawn composition to a moving plastic web or other suitable substrate.

In other embodiments, the adhesive compositions can be coated using a solvent-based method. For example, the solvent-based adhesive composition can be coated by such methods as knife coating, roll coating, gravure coating, rod coating, curtain coating, and air knife coating. The coated solvent-based adhesive composition is then dried to remove the solvent. Preferably, the applied solvent-based adhesive composition is subjected to elevated temperatures, such as those supplied by an oven, to expedite drying.

In certain embodiments, the compositions are used as hot-melt pressure-sensitive adhesives. Some hot-melt pressure-sensitive adhesives are described in Istvan Benedek, "*Technology of Pressure-Sensitive Adhesives and Products*," CRC; Chapter 3, (2008), which is incorporated herein as reference.

In some embodiments, the compositions are used as rubber-based adhesives or contact bond adhesives. Some rubber-based adhesives or contact bond adhesives are described in A. V. Pocius, "*Adhesion and Adhesives Technology*," Hanser Gardner Publications; 2nd edition, Chapter 9, pp. 259-265 (2002), which is incorporated herein as reference.

The following examples are presented to exemplify embodiments of the invention but are not intended to limit the invention to the specific embodiments set forth. Unless indicated to the contrary, all parts and percentages are by weight. All numerical values are approximate. When numerical ranges are given, it should be understood that embodiments outside the stated ranges may still fall within the scope of the invention. Specific details described in each example should not be construed as necessary features of the invention.

EXAMPLES

Purification of Starting Materials

β-farnesene having 97.6% purity by weight was obtained from Amyris Biotechnologies Inc., Emeryville, Calif. β-Farnesene included hydrocarbon-based impurities such as zingiberene, bisabolene, farnesene epoxide, farnesol isomer, E,E-farnesol, squalene, ergosterol, and some dimers of farnesene. β-farnesene was purified with a 3 Å molecular sieve to remove the impurities and were then redistilled under nitrogen atmosphere to improve purity. Cyclohexane was distilled under nitrogen atmosphere to eliminate moisture and stored with a drying agent.

Differential Scanning Calorimetry

A TA Q200 differential scanning calorimeter was utilized to determine glass transition temperatures ($T_g$) of polymer samples disclosed herein. A 5 mg sample was placed in an aluminum pan. An empty reference pan and the sample pan were maintained within ±0.01 mg. Samples were scanned from about −175° C. to about 75° C. at a rate of 10° C./min. $T_g$ was identified as a step change transition in the heat flow. The mid-point of the transition was reported as the $T_g$ of the sample.

Gel Permeation Chromatography

GPC was utilized to determine the molecular weights and polydispersities of polymer samples. A Waters 2414 refractive index detector was used with a Waters 1515 isocratic HPLC pump. HPLC grade tetrahydrofuran was used as solvent. Polydispersed fractions were collected from GPC. The molecular weight of a sample was generally recorded as the number averaged molecular weight ($M_n$) or the weight average ($M_w$). When there were overlapping peaks which prohibited the determination of a unique polydispersity of each peak, a peak molecular weight ($M_p$) was incorporated herein.

Thermal Gravimetric Analysis

The degradation temperatures of samples were determined by thermal gravimetric analysis (TGA). About 20 mg of a sample was placed in a tarred pan. The pan was then loaded into a furnace. Air flow was allowed to equilibrate. The sample was then heated from room temperature to 580° C. at 10° C./min. Temperatures for 1% and 5% weight loss of samples were reported respectively.

Ultraviolet-Visible Spectroscopy

Ultraviolet-visible (UV-Vis) spectroscopy was utilized to monitor monomer consumption during the reaction. The reaction was allowed to continue until all monomers had been consumed. A Shimadzu UV-2450 UV-Vis spectrophotometer was utilized. Background measurement was averaged from five measurements with an empty quartz cuvette. Aliquots were periodically taken from the reaction vessel, which was then placed in a square quartz cuvette with having 1 cm beam distance. The absorbance of the sample is directly proportional to the concentration of the monomer in the aliquot. The progress of the reaction was monitored by UV-Vis spectroscopy with the characteristic absorption peak of β-farnesene at 230 nm.

Tensile Strength

Tensile strength of samples were determined using an INSTRON™ tensile tester. A sample was cast into films and cut to the appropriate dimensions. The thickness and width of the sample after processing were measured. A gauge length of 2.54 cm was used with a crosshead speed 25 mm/min.

Lap Test

Lap test was used to characterize adhesive properties of samples. Two substrates were held together by an adhesive. Substrates were then pulled apart, shearing the adhesive. The construct fails in one of three ways. When the substrate failed, it was called a substrate failure. When the adhesive was torn apart, it was called a cohesive failure. When the interface between the substrate and adhesive failed, it was called an adhesive failure. An INSTRON™ tensile tester was used to characterize the forces involved in the failure. The adhesive was applied to a 2 cm² section of the substrate with a crosshead speed of 25 mm/min. Aluminum was used as the substrate. Aluminum was cleaned with acetone before bonding.

$^1$H and $^{13}$C Nuclear Magnetic Resonance $^1$H and $^{13}$C Nuclear Magnetic Resonance was utilized to characterize chemical microstructures of the samples. A Varian Mercury 300 MHz NMR was utilized for these measurements. Deuterated chloroform was used as the solvent. Several measurements were repeated for collecting spectra.

Example 1

1,4-polyfarnesene Having a $M_n$ of 105,000

To a dried three-neck reactor under argon atmosphere, a pre-dried solution comprising 92.29 g of β-farnesene in 13.7% in cyclohexane was added. n-Butyl lithium ($1.85 \times 10^{-3}$ mol, obtained from Acros, Morris Plains, N.J.) was added into the reactor as an initiator, and the reactor was heated at about 50° C. for about 19 hours, until all β-farnesene was consumed, monitored by UV-Vis spectroscopy. Example 1 was precipitated from the reaction mixture with a 1% solution of ethanol and t-butyl catachol (obtained from Sigma-Aldrich, St. Louis, Mo.). After drying in a vacuum oven at about 60° C. for about 2 hours, Example 1 was kept under vacuum for about 16 hours. Afterwards, Example 1, collected at 89.83 g (yield 97%), was stored in a refrigerator to prevent any crosslinking before characterization.

The progress of synthesizing Example 1 was monitored by the disappearance of β-farnesene, as measured by UV-Vis in the reaction mixture. FIG. 1 shows the Ultraviolet-Visible (UV-Vis) spectra of Example 1 and β-farnesene. The characteristic absorption peak of β-farnesene at 230 nm is present in the UV-Vis spectrum for β-farnesene in FIG. 1, but absent in the UV-Vis spectrum for Example 1 in FIG. 1.

Figure 2:
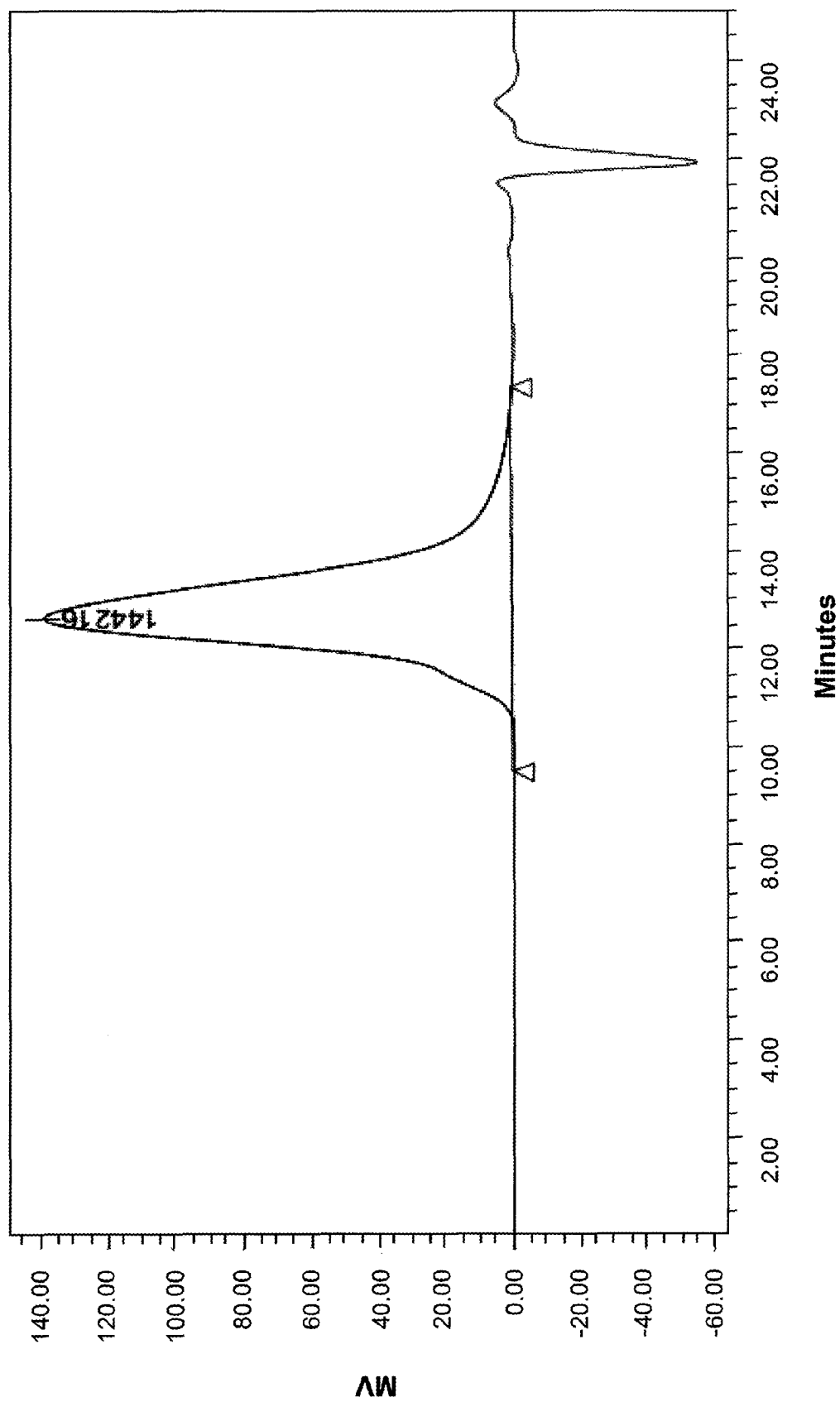
FIG. 2 depicts a Gel Permeation Chromatography (GPC) curve of Example 1.

The molecular weight and polydispersity of Example 1 were determined by GPC. FIG. 2 shows the GPC curve of Example 1. The number average molecular weight ($M_n$), weight average molecular weight ($M_w$), peak molecular weight ($M_p$), z average molecular weight ($M_z$), z+1 average molecular weight ($M_{z+1}$), $M_w/M_n$ (i.e., polydispersity), $M_z/M_w$, and $M_{z+1}/M_w$ of Example 1 are shown in Table 1. The definitions of $M_n$, $M_w$, $M_z$, $M_{z+1}$, $M_p$, and polydispersity can be found in Technical Bulletin TB021, "Molecular Weight Distribution and Definitions of MW Averages," published by Polymer Laboratories, which is incorporated herein by reference. Some methods of measuring the molecular weights of polymers can be found in the book by Malcolm P. Stevens, "*Polymer Chemistry: An Introduction*," Oxford University Press, Chapter 2 (1999), pp. 35-58, which is incorporated herein by reference. The number of farnesene units in Example 1 was calculated to be about 490.

TABLE 1

| Properties | Example 1 |
| --- | --- |
| $M_n$ | 104,838 g/mol |
| $M_w$ | 147,463 g/mol |
| $M_p$ | 144,216 g/mol |
| $M_z$ | 207,084 g/mol |
| $M_{z+1}$ | 314,887 g/mol |
| Polydispersity | 1.406588 |
| $M_z/M_w$ | 1.404311 |
| $M_{z+1}/M_w$ | 2.135360 |

Figure 3:
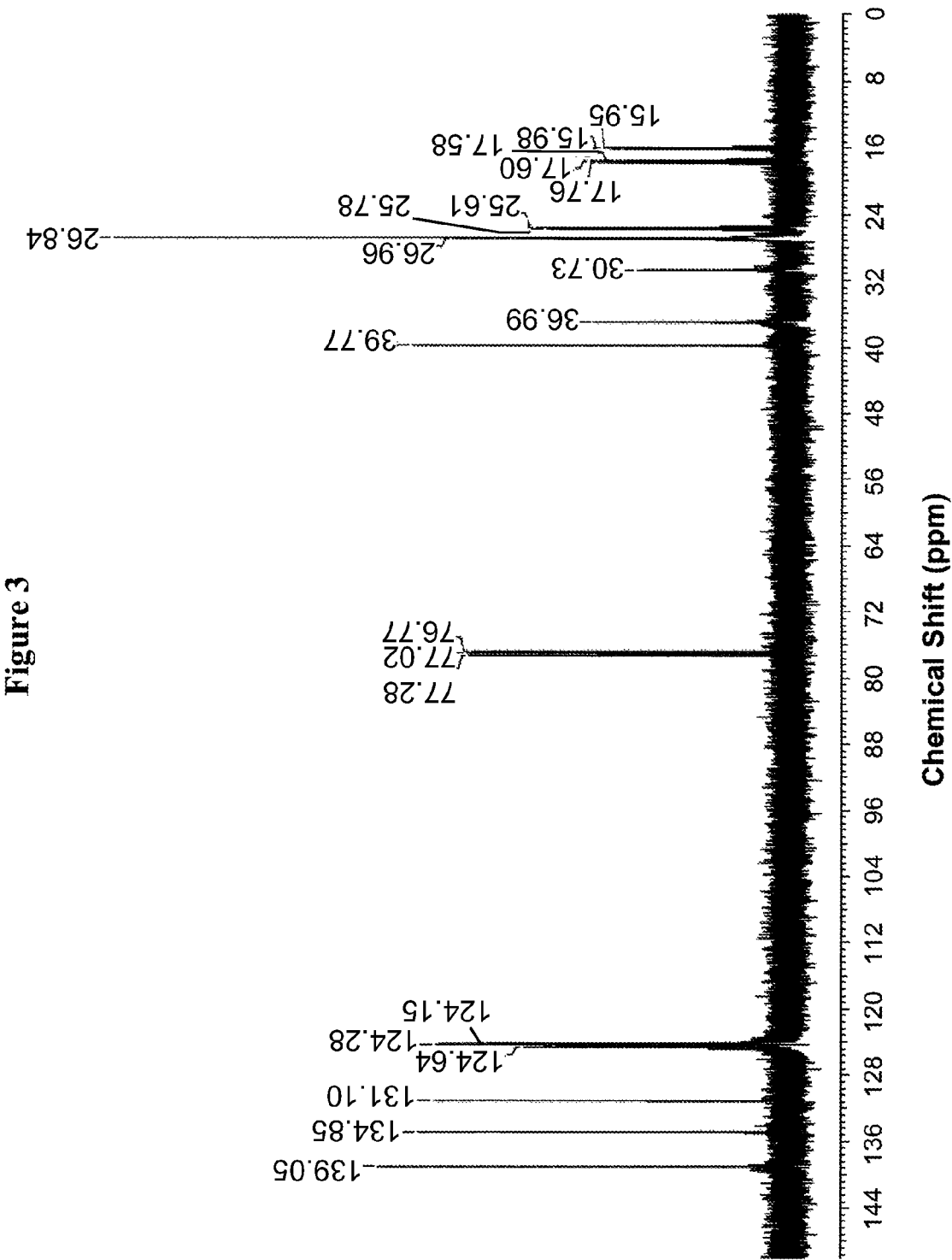
FIG. 3 depicts a $C^{13}$ Nuclear Magnetic Resonance (NMR) spectrum of Example 1.

FIG. 3 shows the $^{13}$C NMR spectrum of Example 1. Peaks at 77.28 ppm, 77.02 ppm, and 76.77 ppm were peaks associated with the deuterated chloroform used for collecting the $^{13}$C NMR spectrum. The characteristic peak identifying Example 1 was at 139.05 ppm.

Figure 4:
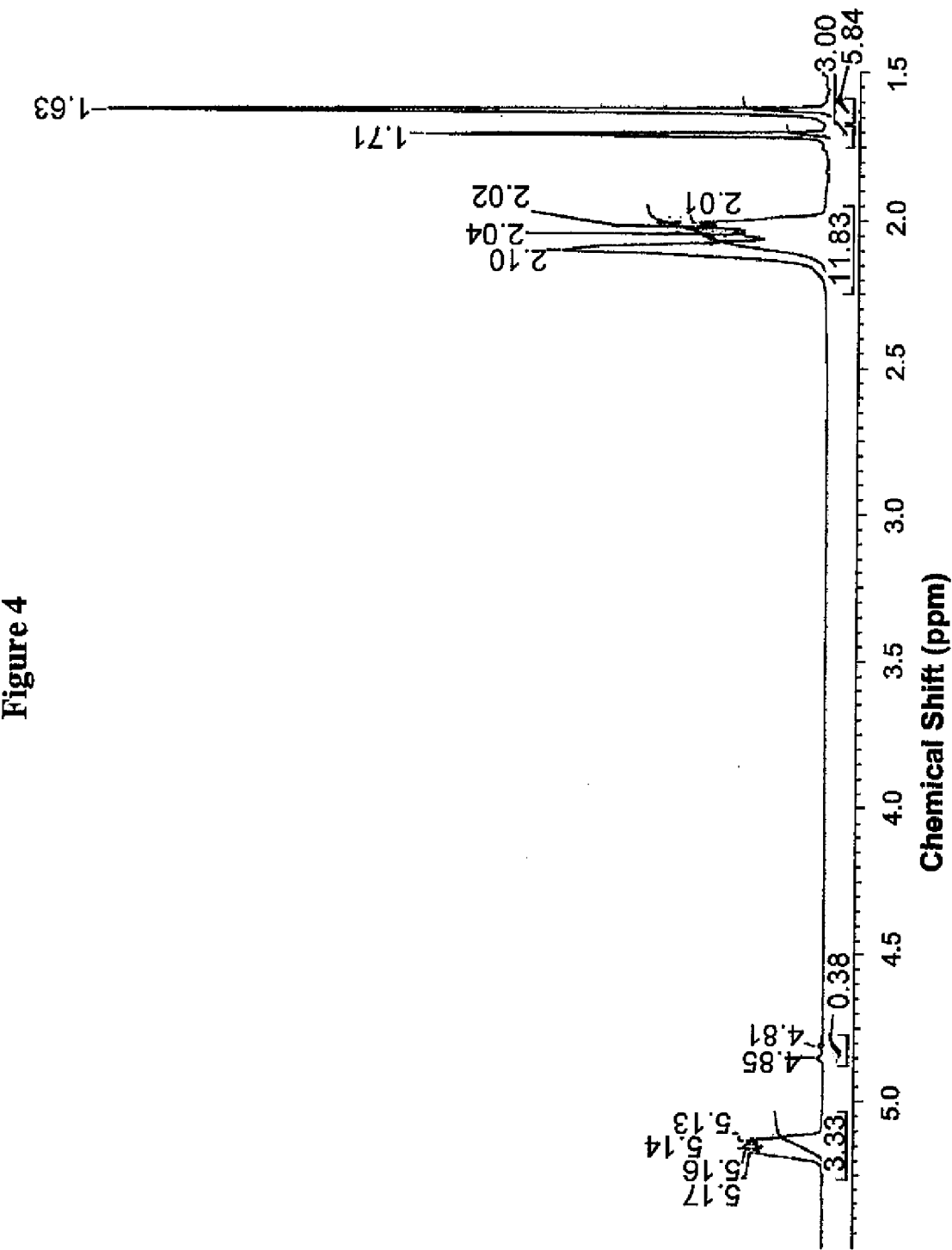
FIG. 4 depicts a $H^1$ NMR spectrum of Example 1.

FIG. 4 shows the $^1$H NMR spectrum of Example 1. Peaks at 4.85 ppm and 4.81 ppm were peaks associated with 3,4-microstructure. Peaks at 5.17 ppm, 5.16 ppm, 5.14 ppm, and 5.13 ppm were peaks associated with 1,4- and 3,4-microstructures. Based on the areas under the peaks of FIG. 4, about 12% of farnesene units in Example 1 was found to have 3,4-microstructure.

Figure 5:
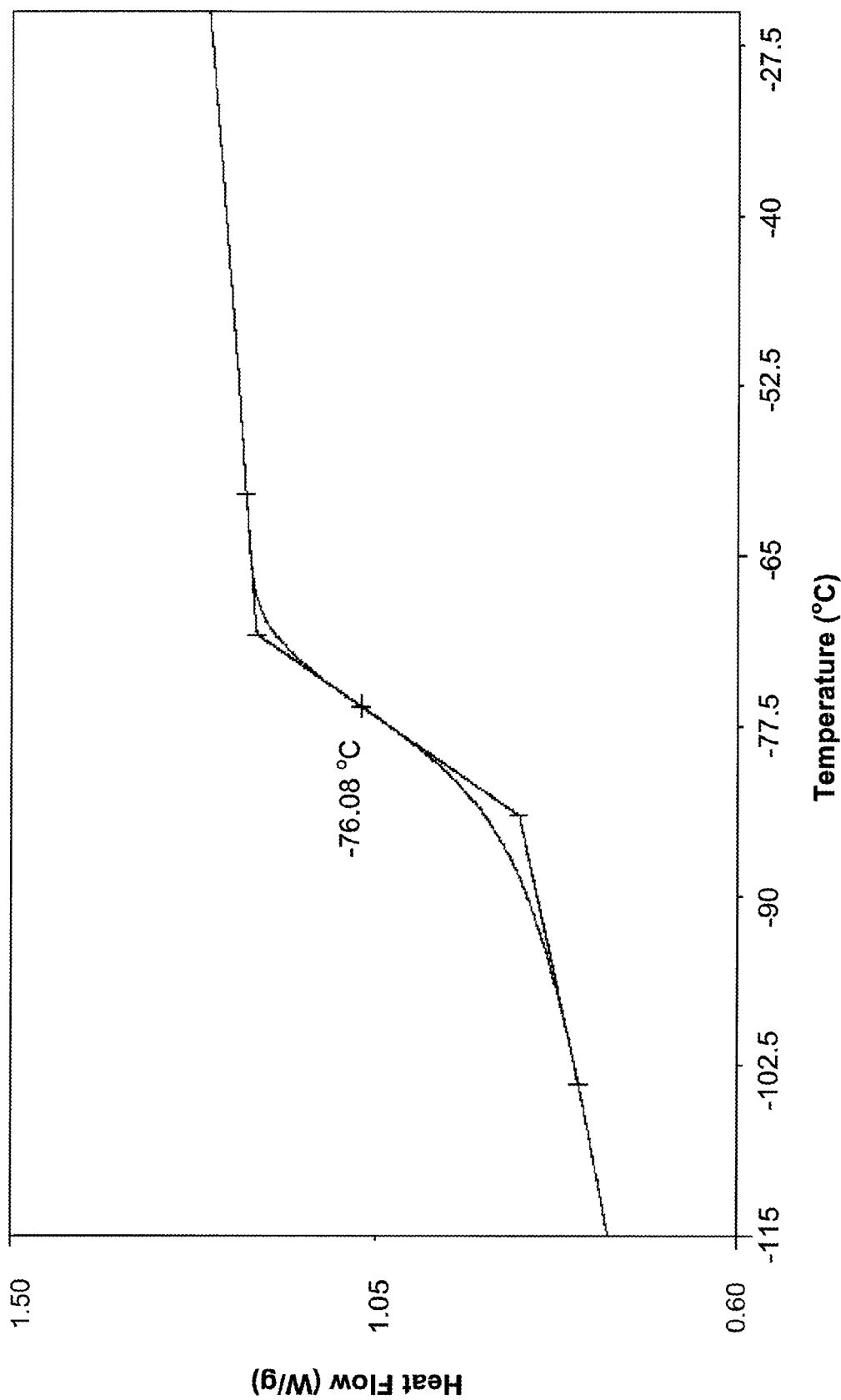
FIG. 5 depicts a Differential Scanning Calorimetry (DSC) curve of Example 1.

The DSC curve of Example 1 is shown in FIG. 5. The thermal characteristics of Example 1 were measured by DSC. The $T_g$ of Example 1 was found to be about −76° C. No other thermal event was detected between −175° C. and 75° C.

Figure 6:
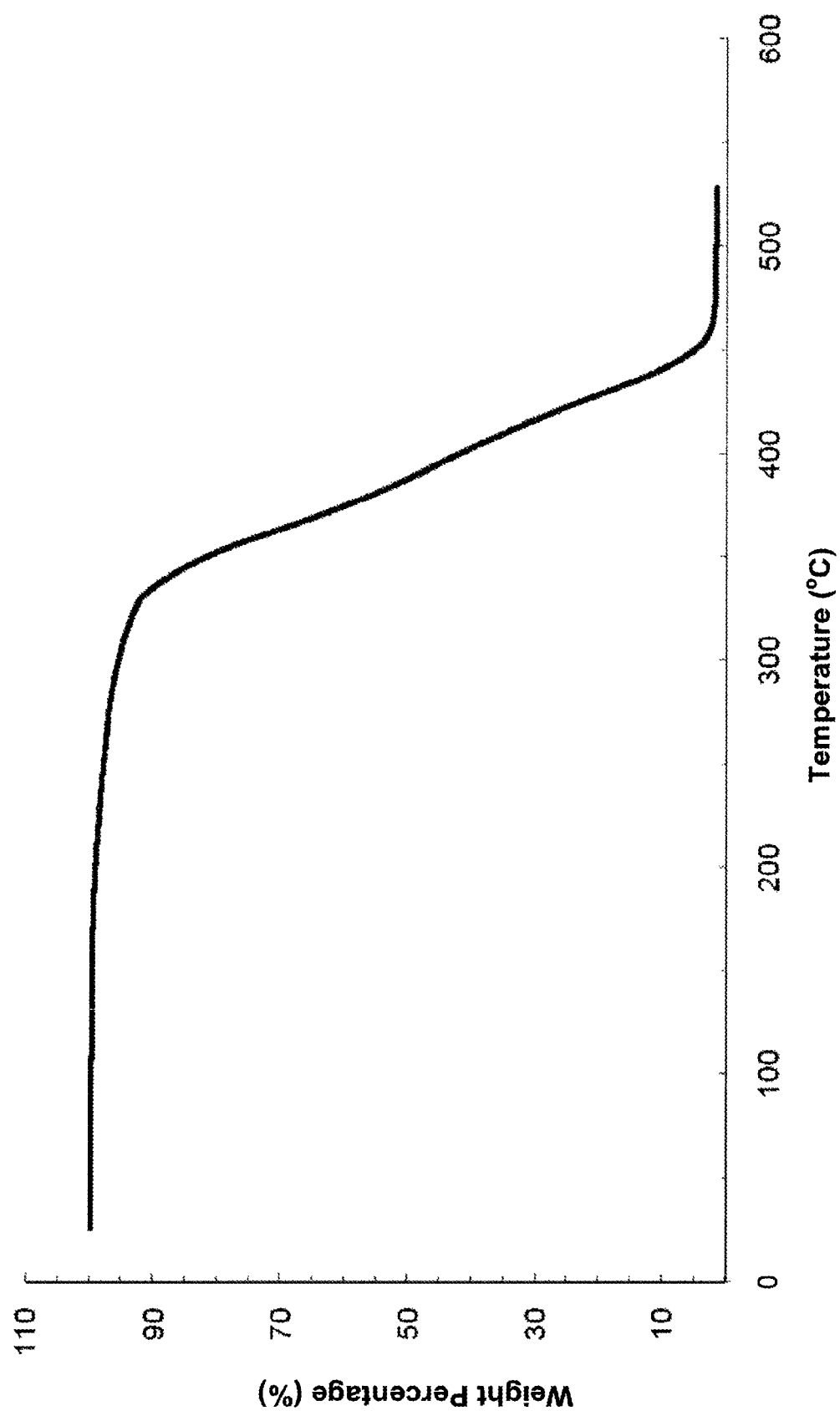
FIG. 6 depicts a Thermal Gravimetric Analysis (TGA) curve of Example 1 measured in air.

The TGA curve of Example 1 measured in air is shown in FIG. 6. The decomposition temperature of Example 1 in air was determined by TGA. The 1% weight loss of Example 1 in air was recorded at 210° C. and the 5% weight loss of Example 1 in air was recorded at 307° C.

Figure 7:
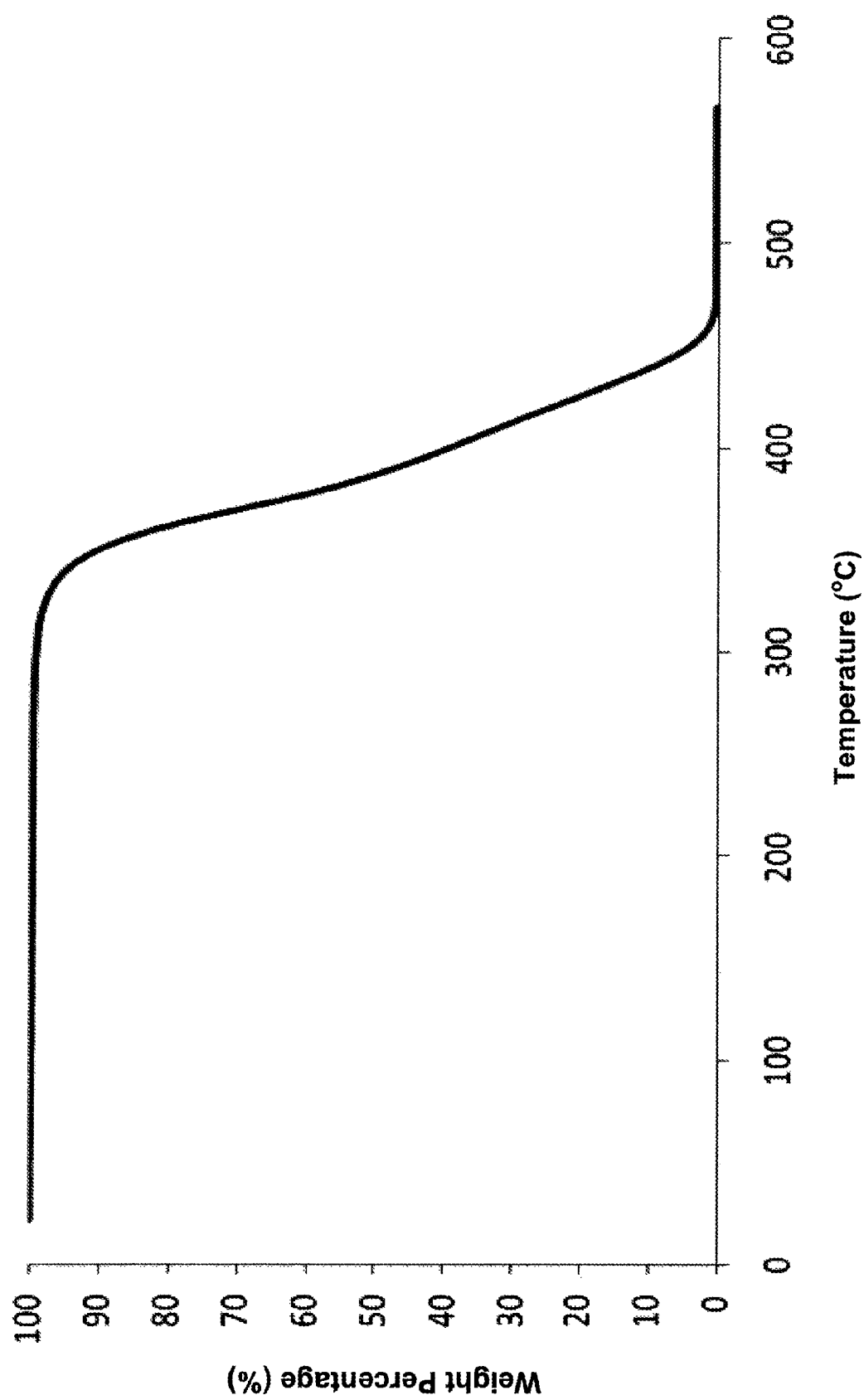
FIG. 7 depicts a TGA curve of Example 1 measured in nitrogen.

The TGA curve of Example 1 measured under nitrogen atmosphere is shown in FIG. 7. The 1% weight loss of Example 1 under nitrogen atmosphere was recorded at 307° C. and the 5% weight loss of Example 1 under nitrogen atmosphere was recorded at 339° C.

Figure 8:
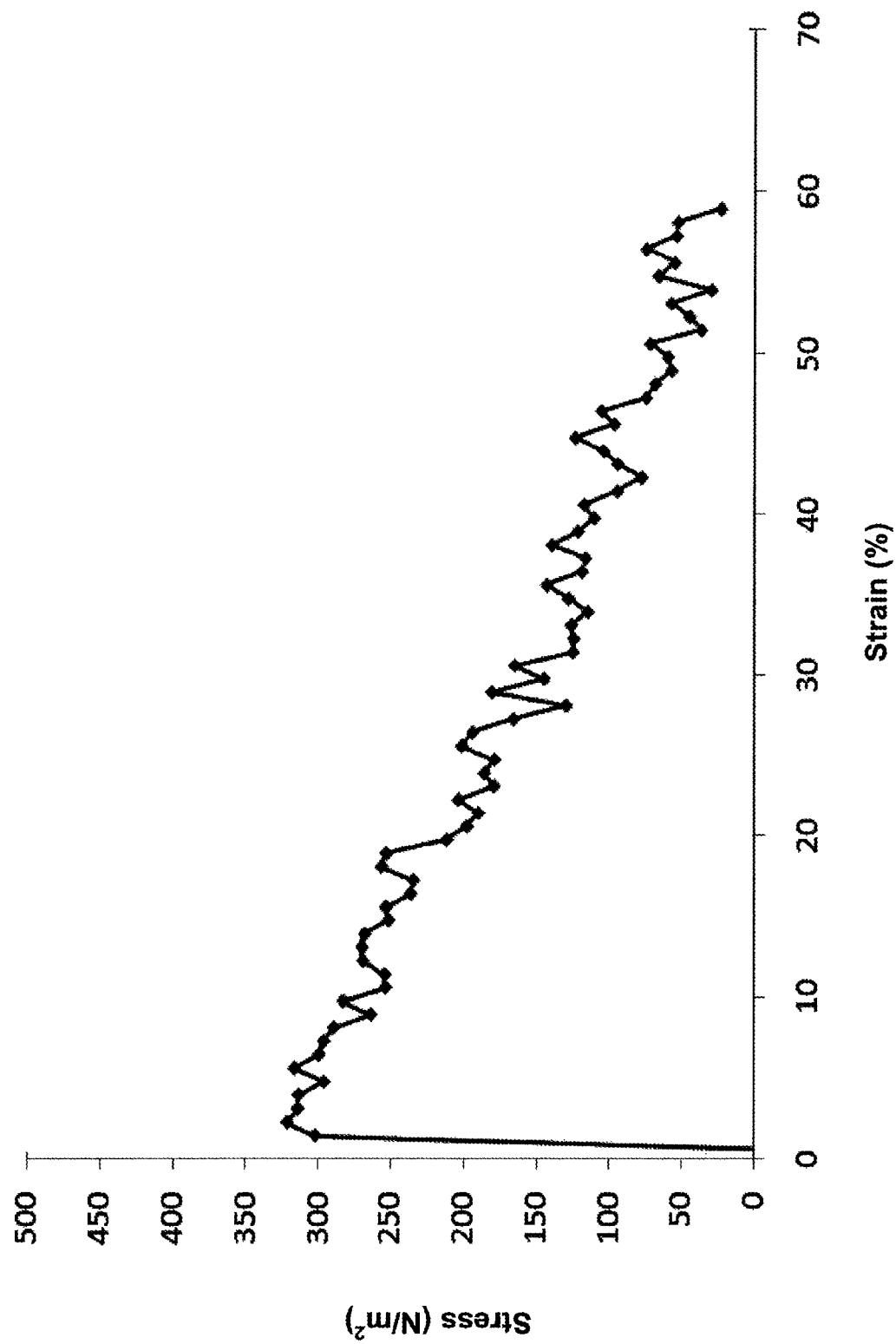
FIG. 8 depicts lap test results of Example 1.

Example 1 was observed to be tacky. The lap test results of Example 1 are shown in FIG. 8. The adhesive capability of Example 1 was measured by the lap test. The adhesive energy of Example 1 was found to be about 11,400 J/m² with a peak stress of about 314 N/m².

Example 2

1,4-polyfarnesene Having a $M_n$ of 245,000

Example 2 is a 1,4-polyfarnesene having a $M_n$ of about 245,000 g/mol. Example 2 was synthesized similarly according to the procedure for Example 1, except sec-butyl lithium was used as the initiator. The net weight of Example 2 was found to be 83.59 g (yield 71.4%). The yield is lower because aliquots were removed to monitor the progression of the reaction.

Figure 9:
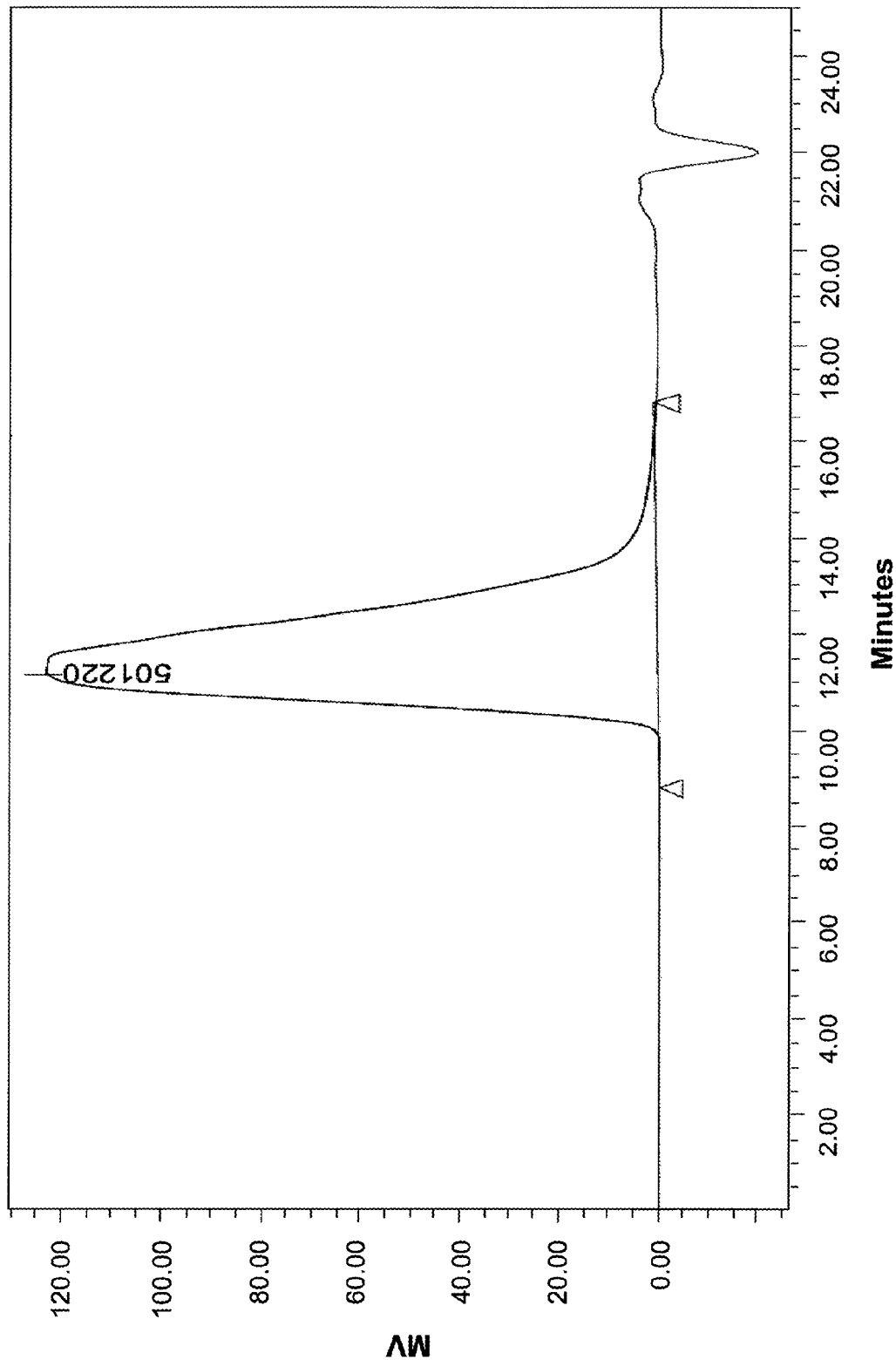
FIG. 9 depicts a GPC curve of Example 2.

The molecular weight and polydispersity of Example 2 were determined by GPC. FIG. 9 shows the GPC curve of Example 2. The $M_n$, $M_w$, $M_p$, $M_z$, $M_{z+1}$, polydispersity, $M_z/M_w$, and $M_{z+1}/M_w$ of Example 2 are shown in Table 2. The number of farnesene units in Example 2 was calculated to be about 2000. Because of the increased molecular weight of Example 2, it had a higher level of entanglement and longer relaxation time than Example 1.

TABLE 2

| Properties | Example 2 |
| --- | --- |
| $M_n$ | 244,747 g/mol |
| $M_w$ | 457,340 g/mol |
| $M_p$ | 501,220 g/mol |
| $M_z$ | 768,187 g/mol |
| $M_{z+1}$ | 1,132,362 g/mol |
| Polydispersity | 1.868622 |
| $M_z/M_w$ | 1.679684 |
| $M_{z+1}/M_w$ | 2.475971 |

Figure 10:
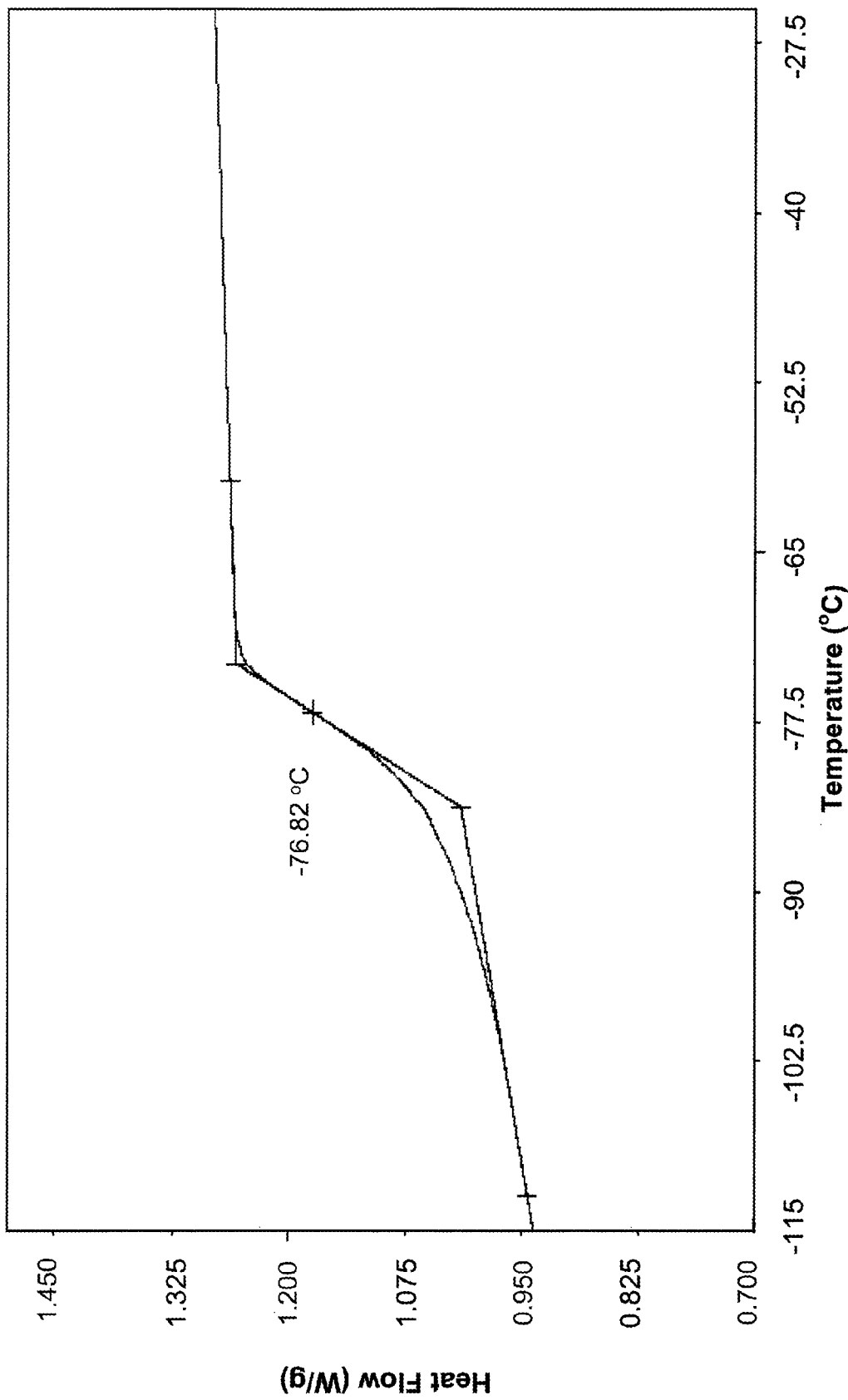
FIG. 10 depicts a DSC curve of Example 2.

The DSC curve of Example 2 is shown in FIG. 10. The thermal characteristics of Example 2 were measured by DSC. The $T_g$ of Example 2 was found to be about −76° C.

Figure 11:
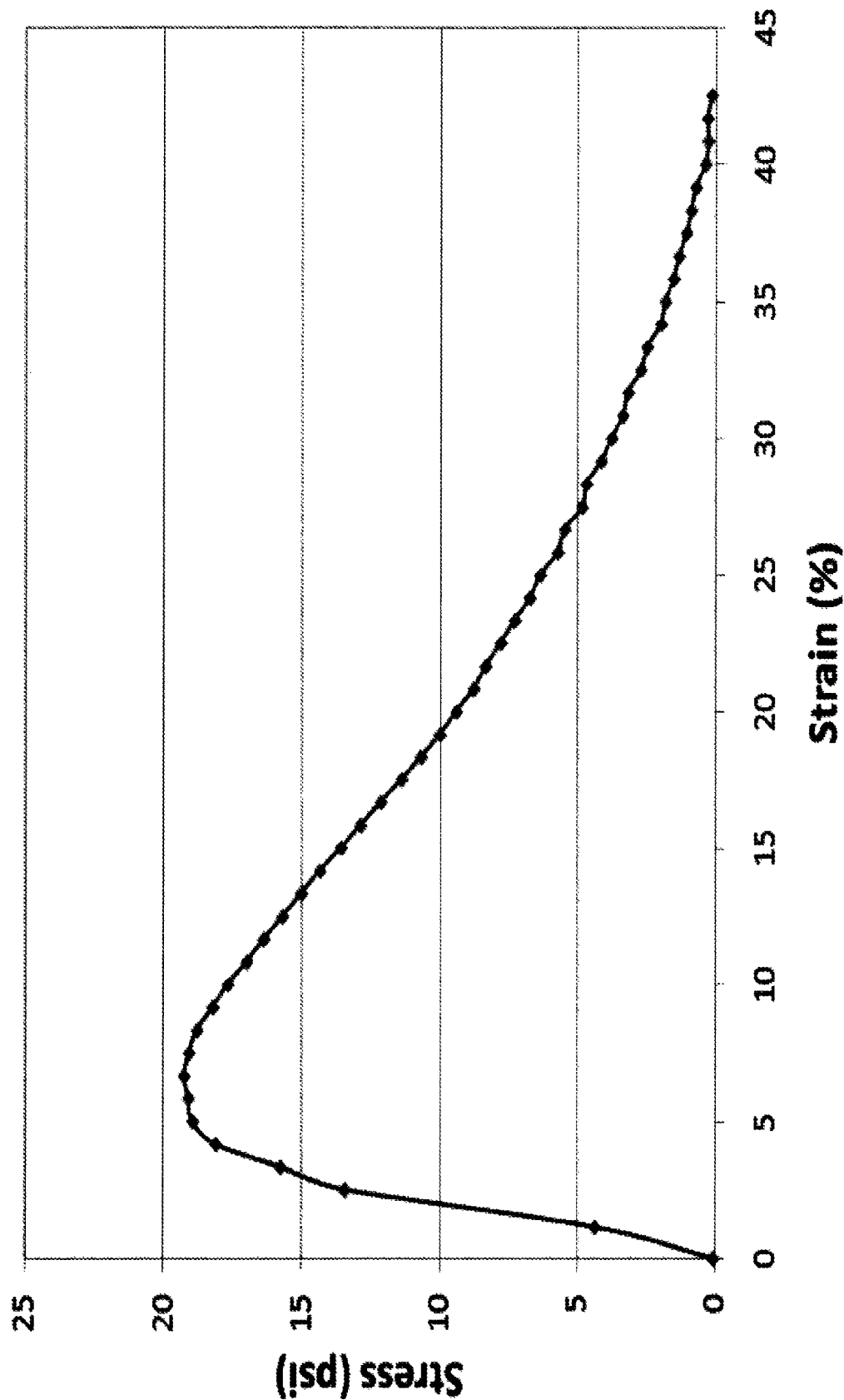
FIG. 11 depicts tensile test results of Example 2.

The tensile test results of Example 2 are shown in FIG. 11. The tensile strength of Example 2 was measured by a tensile test. Example 2 was observed to be soft, tacky and yielded quickly. As shown in FIG. 11, the peak elongation of Example 2 was found to be about 6% with a maximum tensile strength of about 19 psi. The modulus of Example 2 was calculated to be about 4.6 kpsi. Example 2 continued to yield to about 40% elongation.

Example 3

3,4-polyfarnesene

Example 3 was synthesized similarly according to the procedure for Example 1 except that n-butyl lithium (1.71×10⁻³ mol) was added in the presence of N,N,N',N'-tetramethylethylenediamine (1.71×10⁻³ mol, TMEDA, obtained from Sigma-Aldrich, St. Louis, Mo.). The net weight of Example 3 was found to be 82.72 g (yield 97%).

Figure 12:
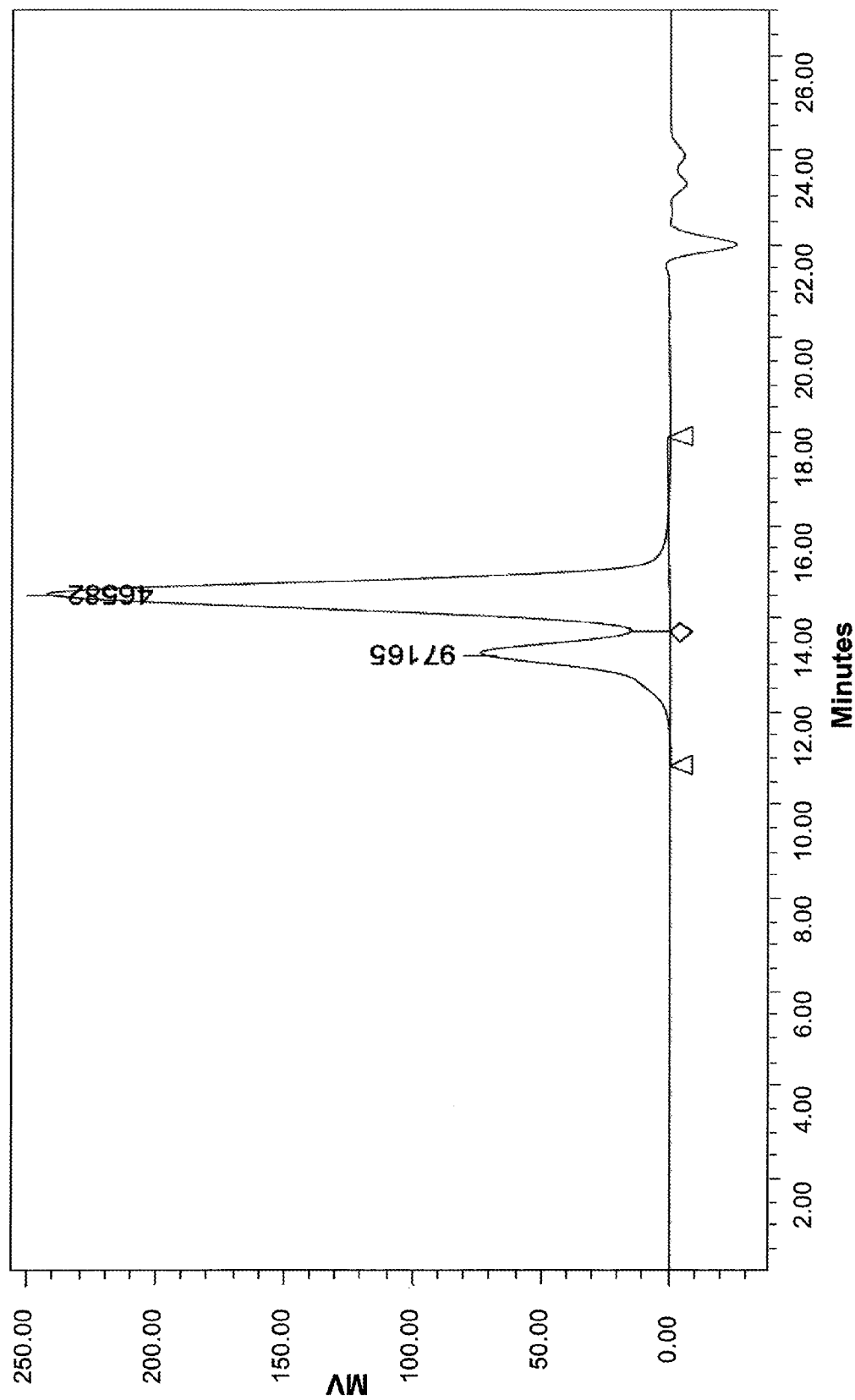
FIG. 12 depicts a GPC curve of Example 3.

The molecular weight and polydispersity of Example 3 were determined by GPC. FIG. 12 shows the GPC curve of Example 3. The two peaks in FIG. 12 indicated that two distinct weight fractions formed in Example 3. The $M_n$, $M_w$, $M_z$, $M_{z+1}$, polydispersity, $M_z/M_w$, and $M_{z+1}/M_w$ of Example 3 are shown in Table 3. The $M_p$ of the first peak in FIG. 12 was about 97,165 g/mol. The $M_p$ of the second peak in FIG. 12 was about 46,582 g/mol. The number of farnesene units in Example 3 was calculated to be about 240.

TABLE 3

| Properties | Example 3 |
| --- | --- |
| $M_n$ | 45,818 g/mol |
| $M_w$ | 47,644 g/mol |
| $M_z$ | 49,134 g/mol |
| $M_{z+1}$ | 50,527 g/mol |
| Polydispersity | 1.039844 |
| $M_z/M_w$ | 1.031269 |
| $M_{z+1}/M_w$ | 1.060509 |

Figure 13:
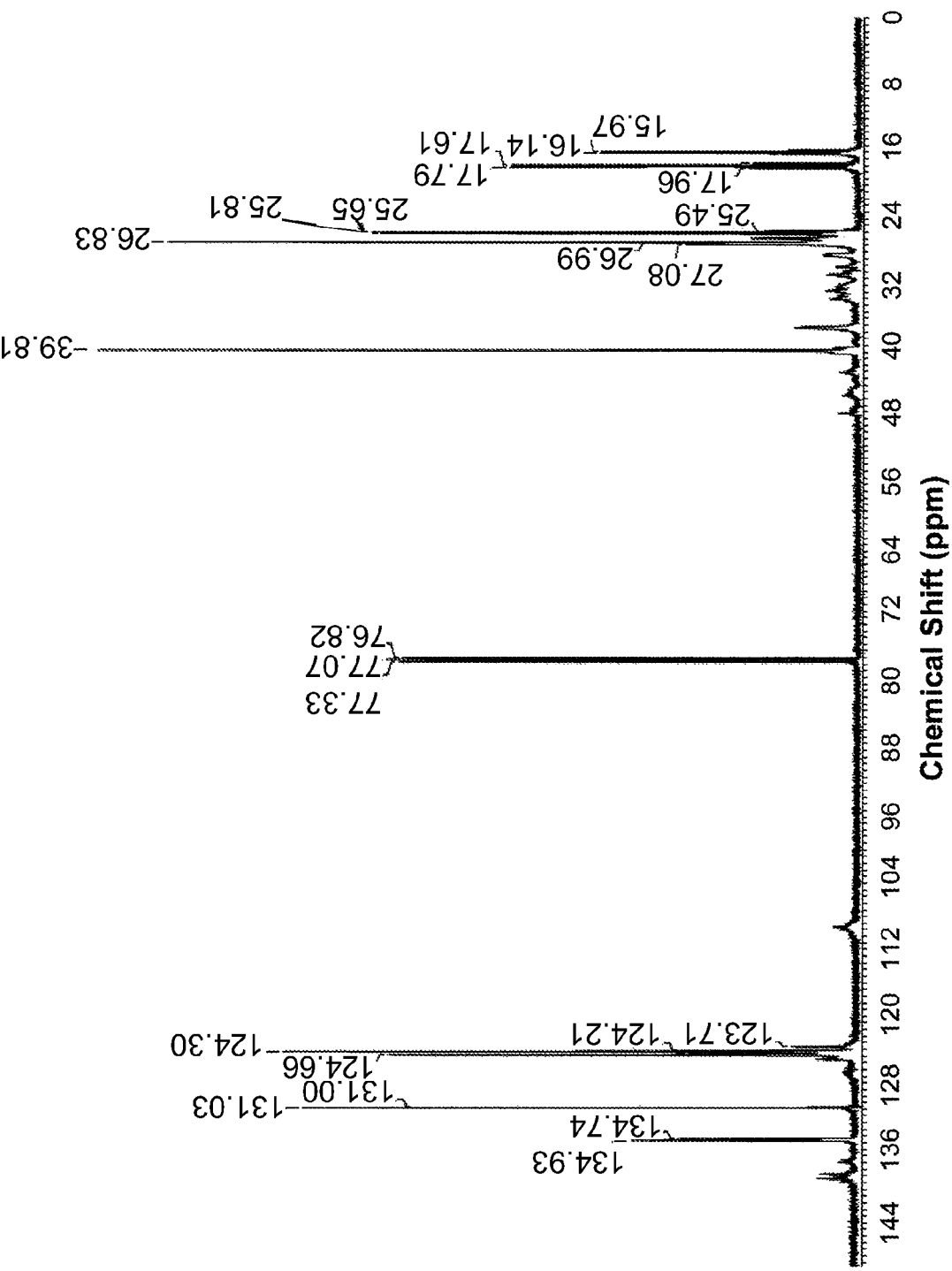
FIG. 13 depicts a $C^{13}$ NMR spectrum of Example 3.

FIG. 13 shows the ¹³C NMR spectrum of Example 3. Peaks at 77.33 ppm, 77.07 ppm, and 76.82 ppm were peaks of deuterated chloroform used for collecting the ¹³C NMR spectrum. The characteristic peak identifying Example 1 at 139.05 ppm was absent in FIG. 13, indicating a regular microstructure of Example 3.

Figure 14:
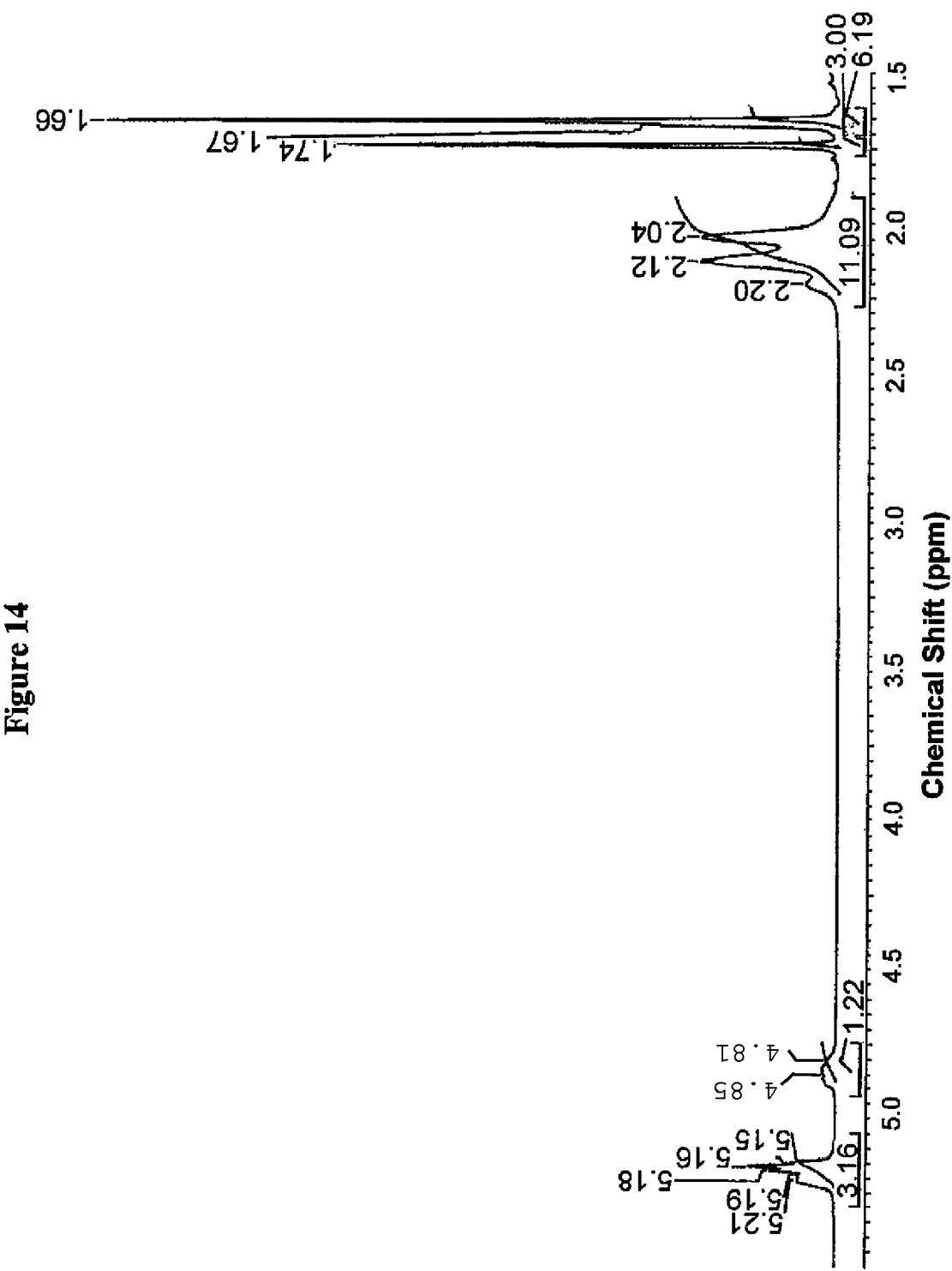
FIG. 14 depicts a $H^1$ NMR spectrum of Example 3.

FIG. 14 shows the ¹H NMR spectrum of Example 3. Peaks at 4.85 ppm and 4.81 ppm were peaks associated with 3,4-microstructure. Peaks at 5.21 ppm, 5.19 ppm, 5.18 ppm, 5.16 ppm, and 5.15 ppm were peaks associated with 1,4- and 3,4-microstructures. Based on the areas under the peaks of FIG. 14, about 10% of farnesene units in Example 3 was found to have 1,4-microstructure.

Figure 15:
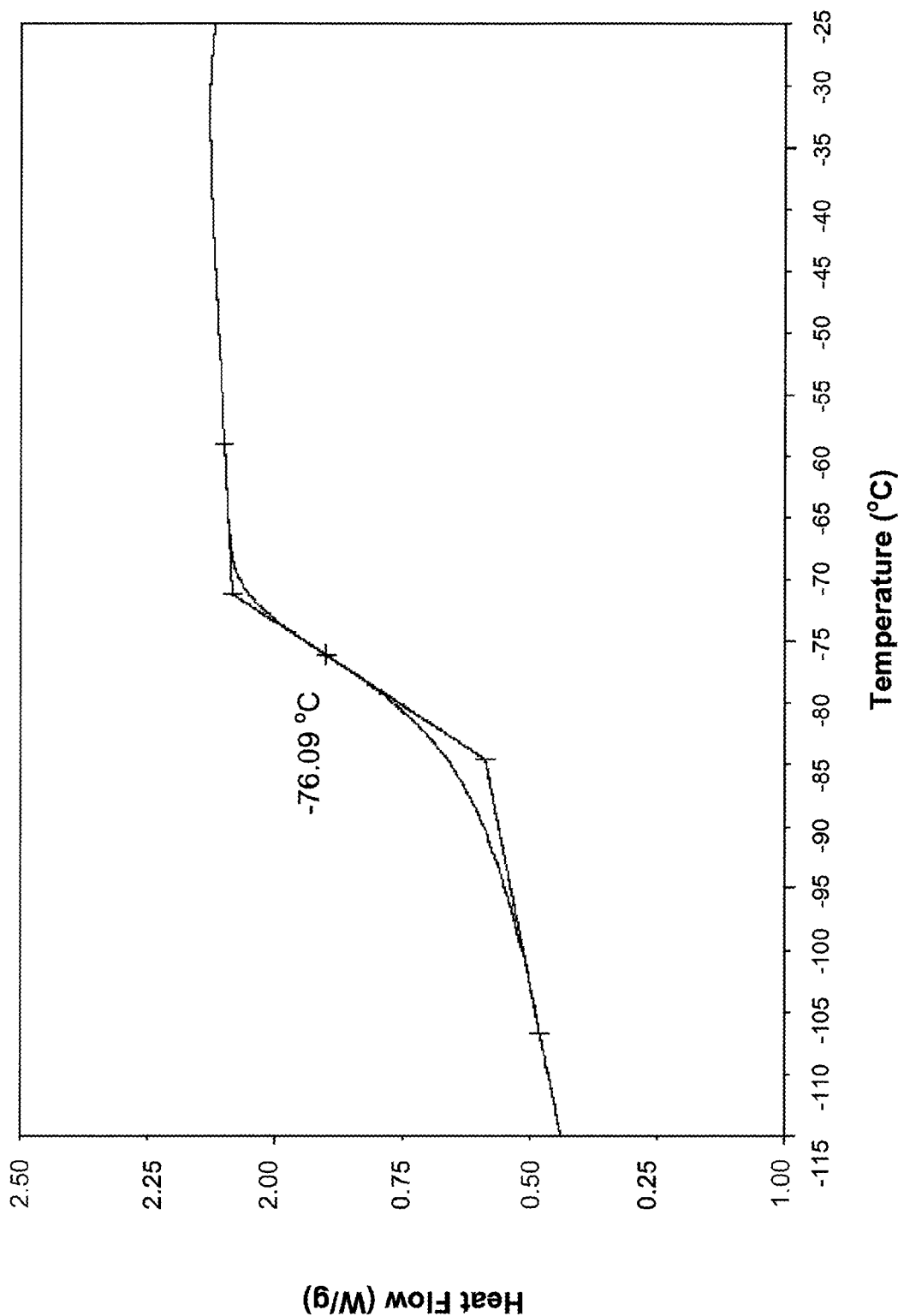
FIG. 15 depicts a DSC curve of Example 3.

The DSC curve of Example 3 is shown in FIG. 15. The thermal characteristics of Example 3 were measured by DSC. The $T_g$ of Example 3 was found to be about −76° C. No other thermal event was detected between −175° C. and 75° C.

Figure 16:
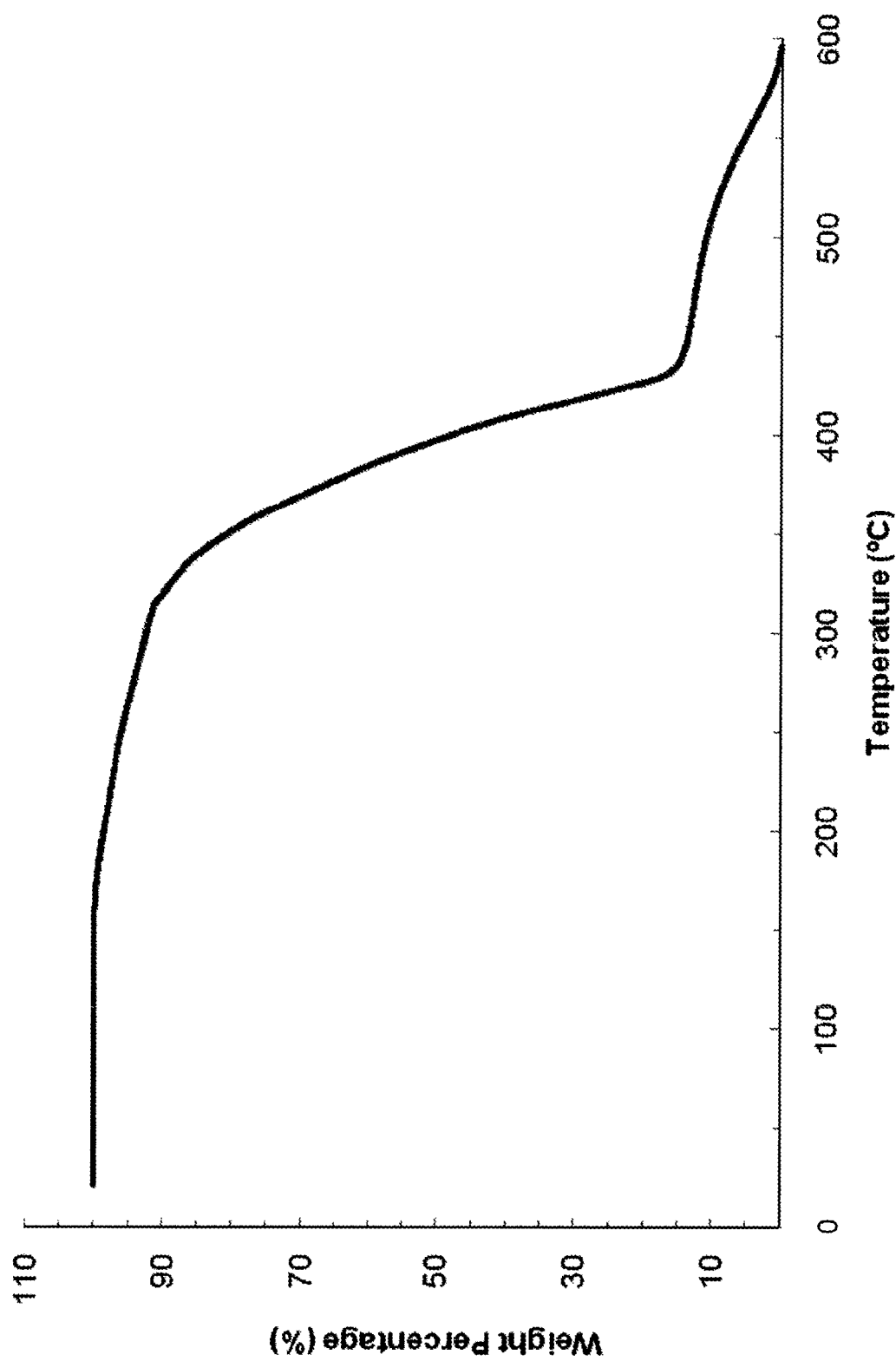
FIG. 16 depicts a TGA curve of Example 3.

The TGA curve of Example 1 measured in air is shown in FIG. 16. The decomposition temperature of Example 3 in air was determined by TGA. The 1% weight loss of Example 1 in air was recorded at 191° C. and the 5% weight loss of Example 1 in air was recorded at 265° C.

Figure 17:
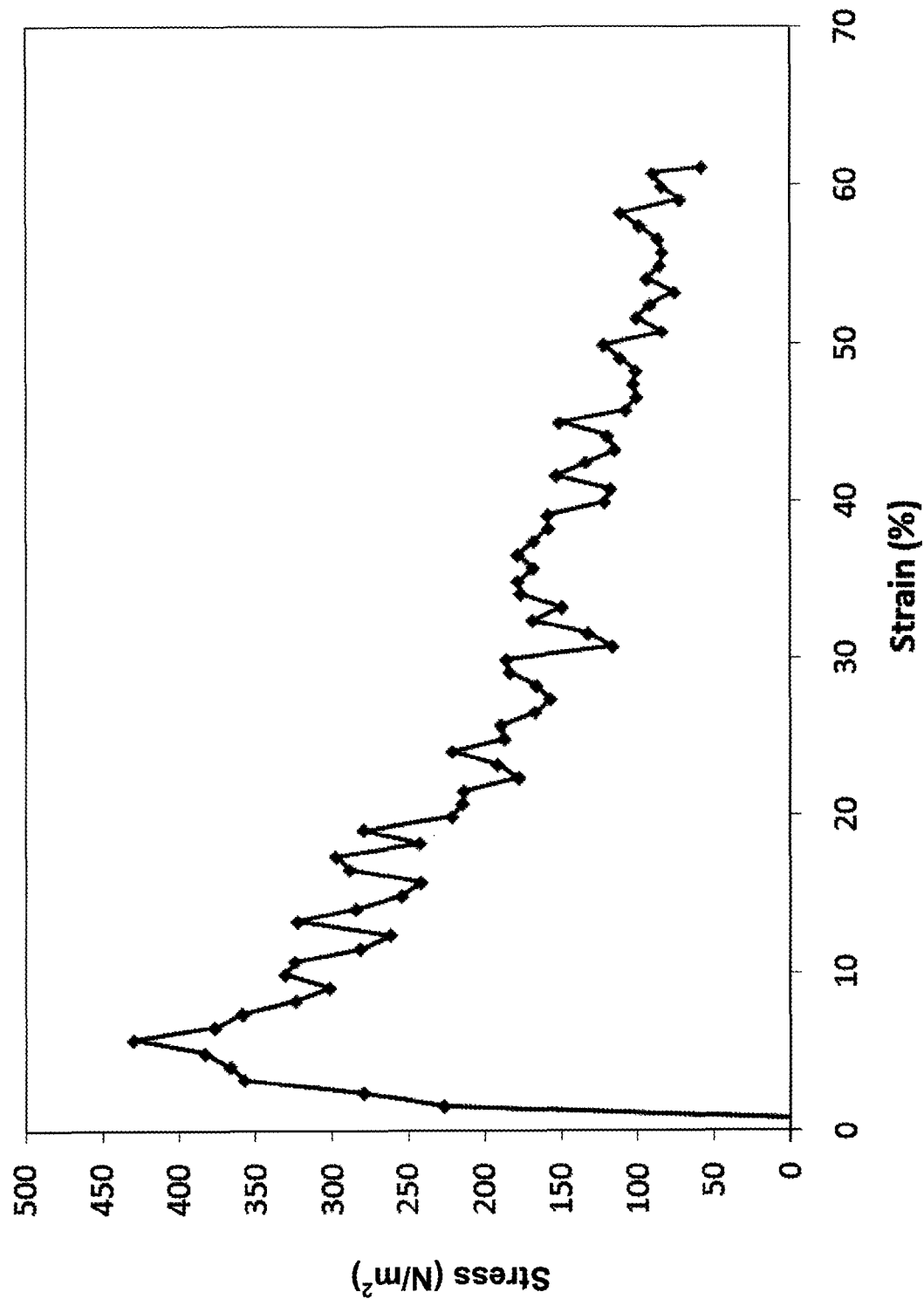
FIG. 17 depicts lap test results of Example 3.

Example 3 was observed to be a highly tacky viscous fluid. The lap test results of Example 3 are shown in FIG. 17. The adhesive capability of Example 3 was measured by the lap test. The adhesive energy of Example 3 was found to be about 12,900 J/m² with a peak stress of about 430 N/m².

Example 4

Polystyrene-1,4-polyfarnesene-polystyrene

To a first dried three neck reactor under argon atmosphere, a pre-dried solution of 12% β-farnesene in cyclohexane was added. To a second dried three neck reactor under argon atmosphere, a 20.65 g solution of 10% styrene in cyclohexane was added. Afterwards, to the styrene solution, n-butyl lithium (6.88×10⁻⁴ mol) was added into the reactor as an initiator, and the reactor was heated at about 50° C. for about 16 hours, until all styrene was consumed, as monitored by GPC. Then, 161.8 β-farnesene solution (i.e., 19.61 g of β-farnesene) was transferred to the reactor under argon atmosphere. The reaction was allowed to react until completion for about 7 hours, monitored by GPC. Three equal aliquots of dichlorosilane coupling agent (3.44×10⁻⁴ mol, obtained from Acros, Morris Plains, N.J.) were then added into the reactor such that the mole ratio of Li to Cl of the reaction mixture was 1:2. The reaction mixture was allowed to react until completion as indicated by a color change from yellow to clear in the reactor. Example 4 was precipitated from the reaction mixture with a 1% solution of t-butyl catachol in ethanol. After drying in a vacuum oven at about 60° C. for about 2 hours, Example 4 was kept under vacuum for about 16 hours. Afterwards, Example 4, collected at 39.15 g (yield 97%), was stored in a refrigerator to prevent any crosslinking before characterization.

Figure 18:
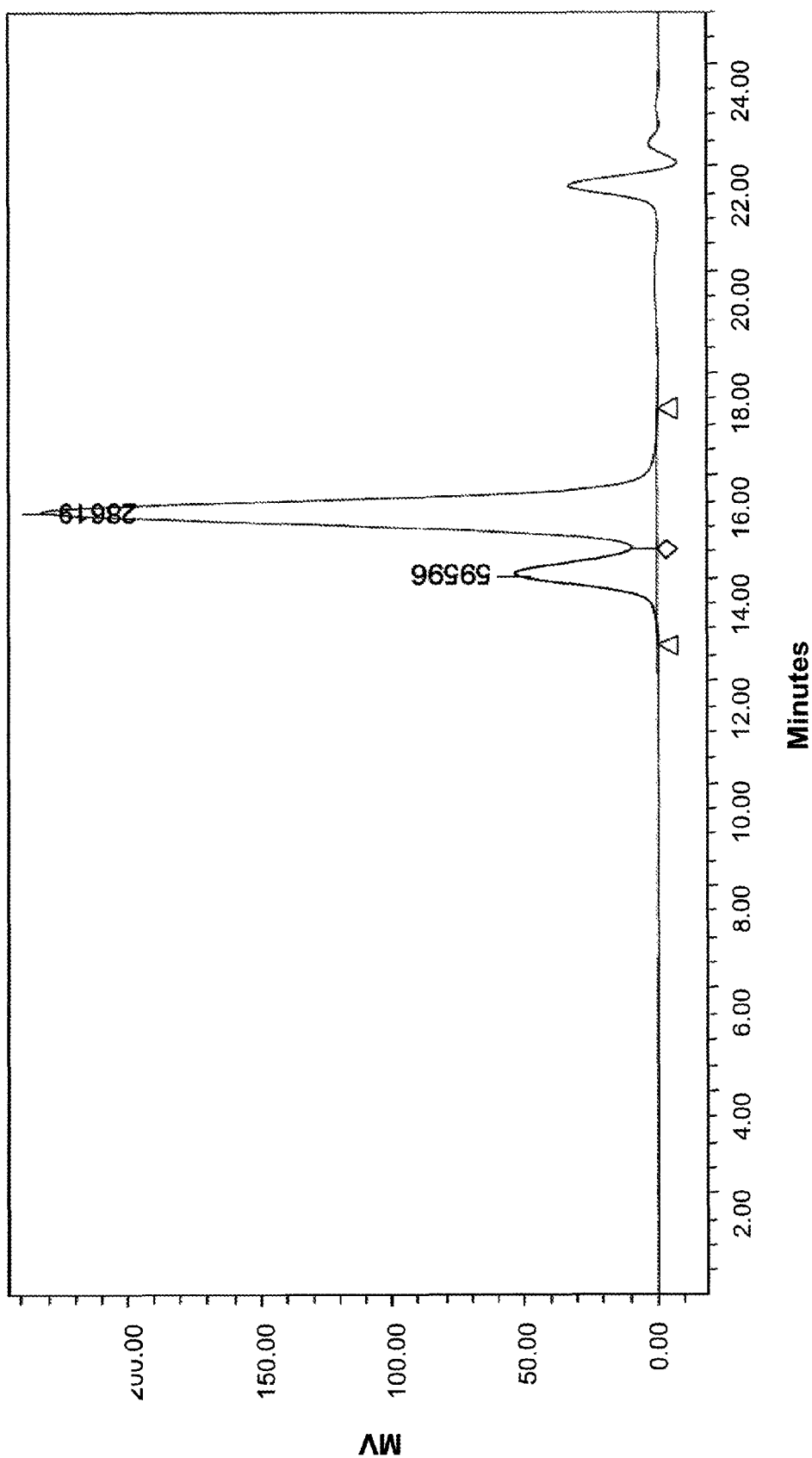
FIG. 18 depicts a GPC curve of polystyrene formed.

The GPC curve of polystyrene is shown in FIG. 18. The progress of polystyrene synthesis reaction was monitored by GPC. The two peaks in FIG. 18 indicated that there were two distinct weight fractions of polystyrene formed. The $M_n$, $M_w$, $M_z$, $M_{z+1}$, polydispersity, $M_z/M_w$, and $M_{z+1}/M_w$ of the polystyrene are shown in Table 4. The $M_p$ of the first peak in FIG. 18 was found to be about 59,596 g/mol. The $M_p$ of the second peak in FIG. 20 was found to be about 28,619 g/mol.

TABLE 4

| Properties | Polystyrene |
| --- | --- |
| $M_n$ | 28,396 g/mol |
| $M_w$ | 29,174 g/mol |
| $M_z$ | 29,895 g/mol |
| $M_{z+1}$ | 30,598 g/mol |
| Polydispersity | 1.027385 |
| $M_z/M_w$ | 1.024739 |
| $M_{z+1}/M_w$ | 1.048810 |

Figure 19:
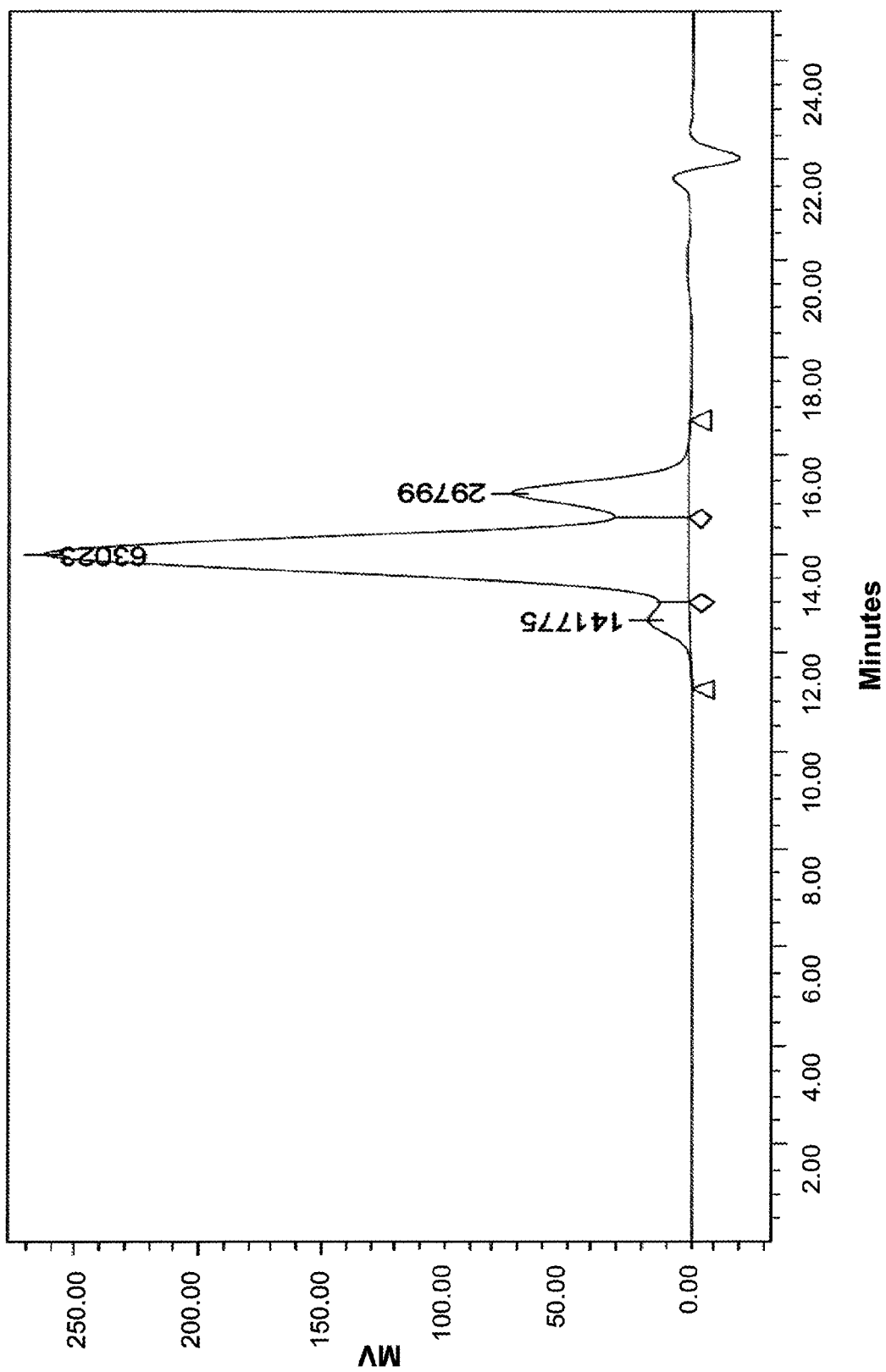
FIG. 19 depicts a GPC curve of polystyrene-1,4-polyfarnesene di-block copolymer formed.

The polystyrene formed then acted as an initiator to initiate the polymerization with β-farnesene to form a polystyrene-1,4-polyfarnesene di-block copolymer. The GPC curve of the di-block copolymer is shown in FIG. 19. The progress of the di-block copolymer synthetic reaction was monitored by GPC. The three peaks in FIG. 19 indicated that there were three distinct weight fractions in the di-block copolymer reaction solution. The $M_n$, $M_w$, $M_p$, $M_z$, $M_{z+1}$, polydispersity, $M_z/M_w$, and $M_{z+1}/M_w$ of the di-block copolymer are shown in Table 5. The $M_p$ of the first peak in FIG. 19, corresponding to polystyrene-1,4-polyfarnesene-polystyrene, was found to be about 141,775 g/mol. The $M_p$ of the second peak in FIG. 19, corresponding to the di-block copolymer, was found to be about 63,023 g/mol. The molecular weight of 1,4-polyfarnesene in the di-block copolymer was calculated to be about 35,000 g/mol. The $M_p$ of the third peak in FIG. 19, corresponding to polystyrene, was found to be about 29,799 g/mol.

TABLE 5

| Properties | Polystyrene-1,4-polyfarnesene Di-block Copolymer |
| --- | --- |
| $M_n$ | 29,434 g/mol |
| $M_w$ | 30,345 g/mol |
| $M_p$ | 29,799 g/mol |
| $M_z$ | 31,172 g/mol |
| $M_{z+1}$ | 31,936 g/mol |
| Polydispersity | 1.030949 |
| $M_z/M_w$ | 1.027264 |
| $M_{z+1}/M_w$ | 1.052449 |

Figure 20:
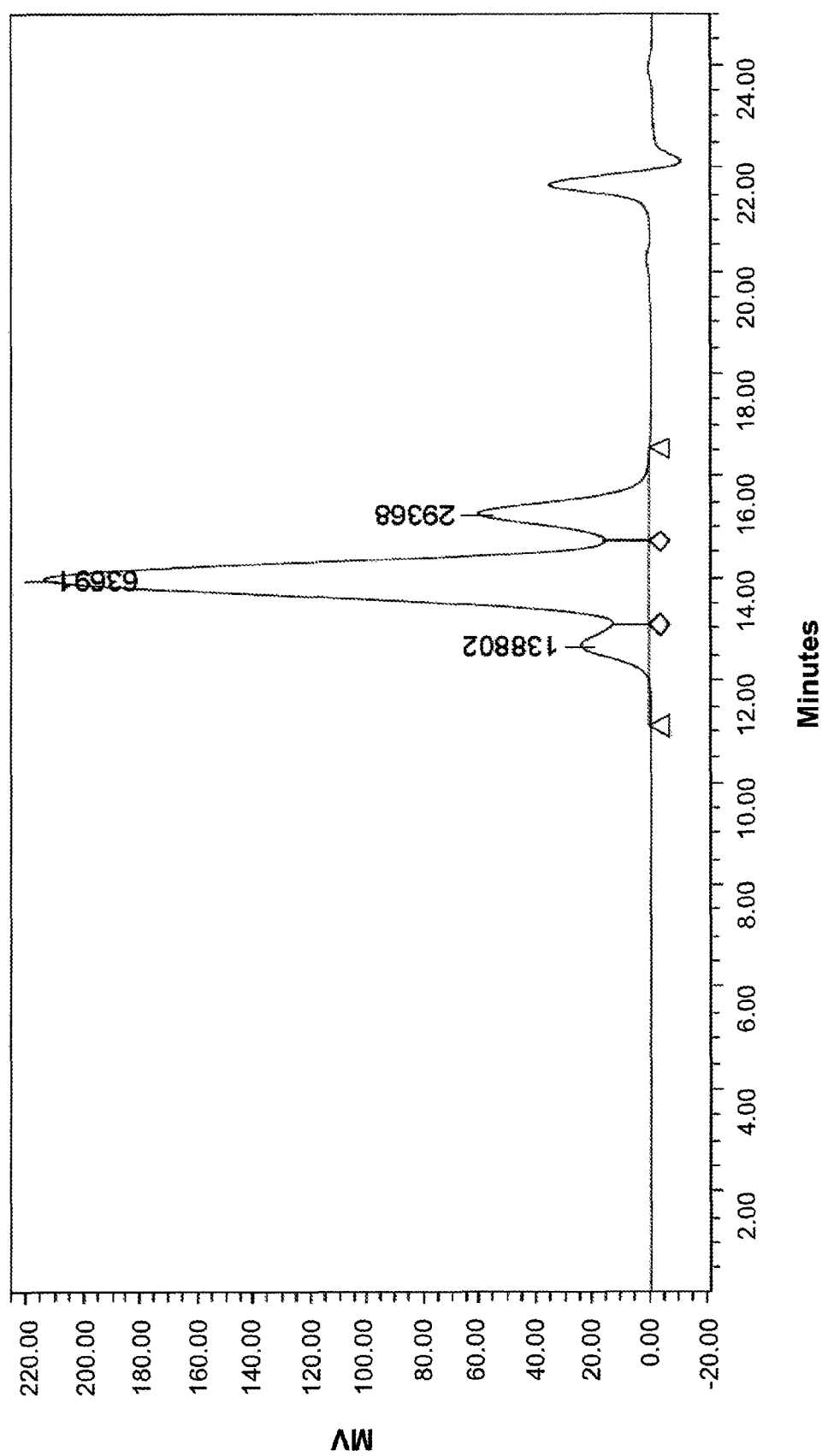
FIG. 20 depicts a GPC curve of Example 4.

The polystyrene-1,4-polyfarnesene di-block copolymer was further coupled to form Example 4. FIG. 20 shows the GPC curve of Example 4. The molecular weight and polydispersity of Example 4 were determined by GPC. The three peaks in FIG. 20 indicated that there were three distinct weight fractions for the coupling product formed. The $M_n$, $M_w$, $M_z$, $M_{z+1}$, polydispersity, $M_z/M_w$, and $M_{z+1}/M_w$ of the coupling product are shown in Table 6. The $M_p$ of the first peak in FIG. 20, corresponding to Example 4, was found to be about 138,802 g/mol. Example 4 was obtained in about 10% of the coupling product. The number of farnesene monomer units in Example 4 was calculated to be about 300. The $M_p$ of the second peak in FIG. 20, which corresponds to polystyrene-1,4-polyfarnesene di-block copolymers, was found to be about 63,691 g/mol. The $M_p$ of the third peak in FIG. 20, corresponding to polystyrene, was found to be about 29,368 g/mol.

TABLE 6

| Properties | Example 4 |
| --- | --- |
| $M_n$ | 138,240 g/mol |
| $M_w$ | 142,147 g/mol |
| $M_z$ | 146,636 g/mol |
| $M_{z+1}$ | 151,848 g/mol |
| Polydispersity | 1.028264 |
| $M_z/M_w$ | 1.031576 |
| $M_{z+1}/M_w$ | 1.068242 |

Figure 21:
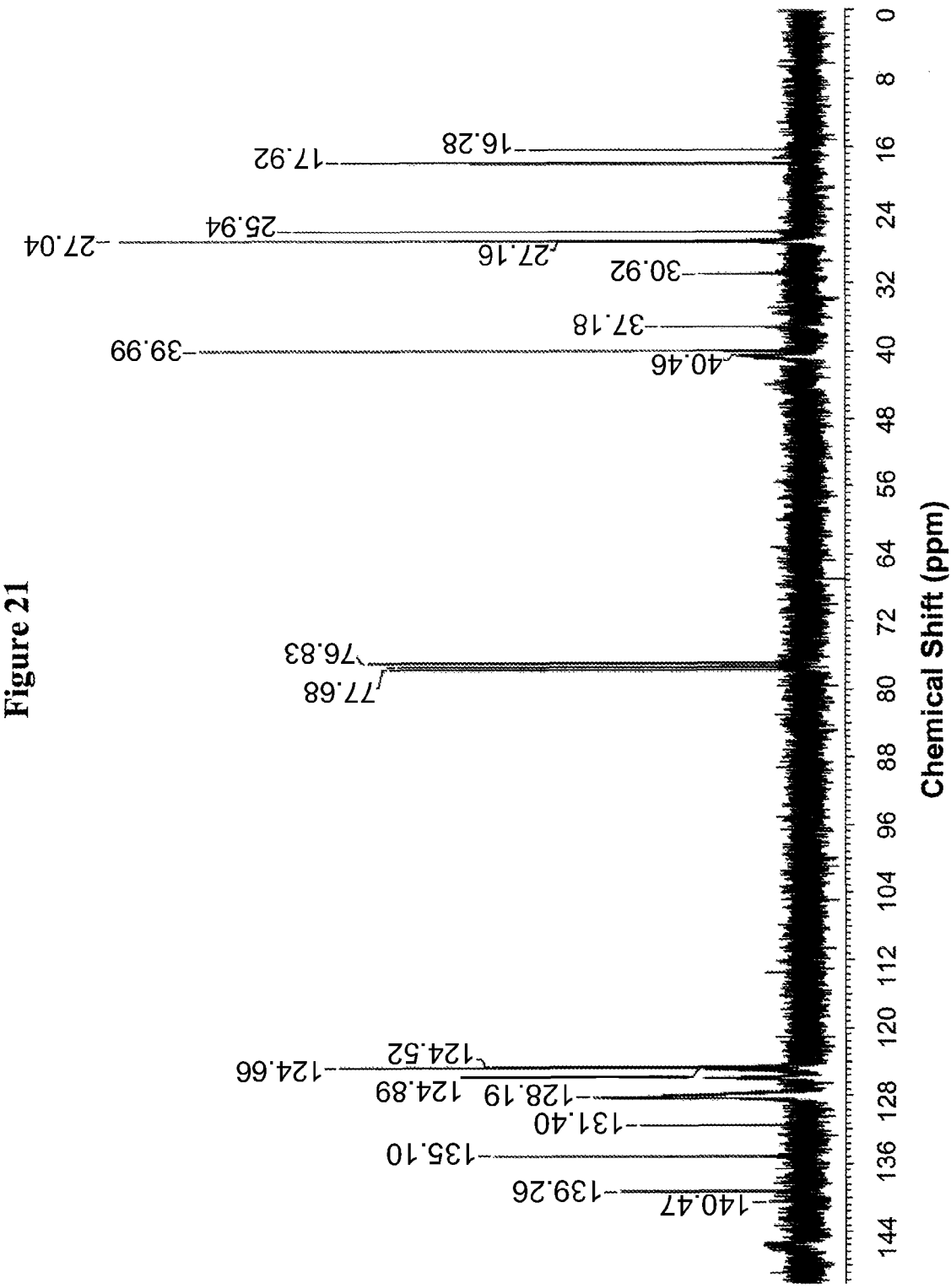
FIG. 21 depicts a $^{13}C$ NMR spectrum of Example 4.

FIG. 21 shows the $^{13}$C NMR spectrum of Example 4. Peaks at 77.69 ppm and 76.80 ppm were peaks of associated with the deuterated chloroform used for collecting the $^{13}$C NMR spectrum. Other peaks in FIG. 21 were peaks associated with 1,4-polyfarnesene and polystyrene. The characteristic peak identifying 1,4-polyfarnesene at 139.25 ppm was present in FIG. 21, indicating the presence of 1,4-polyfarnesene in Example 4.

Figure 22:
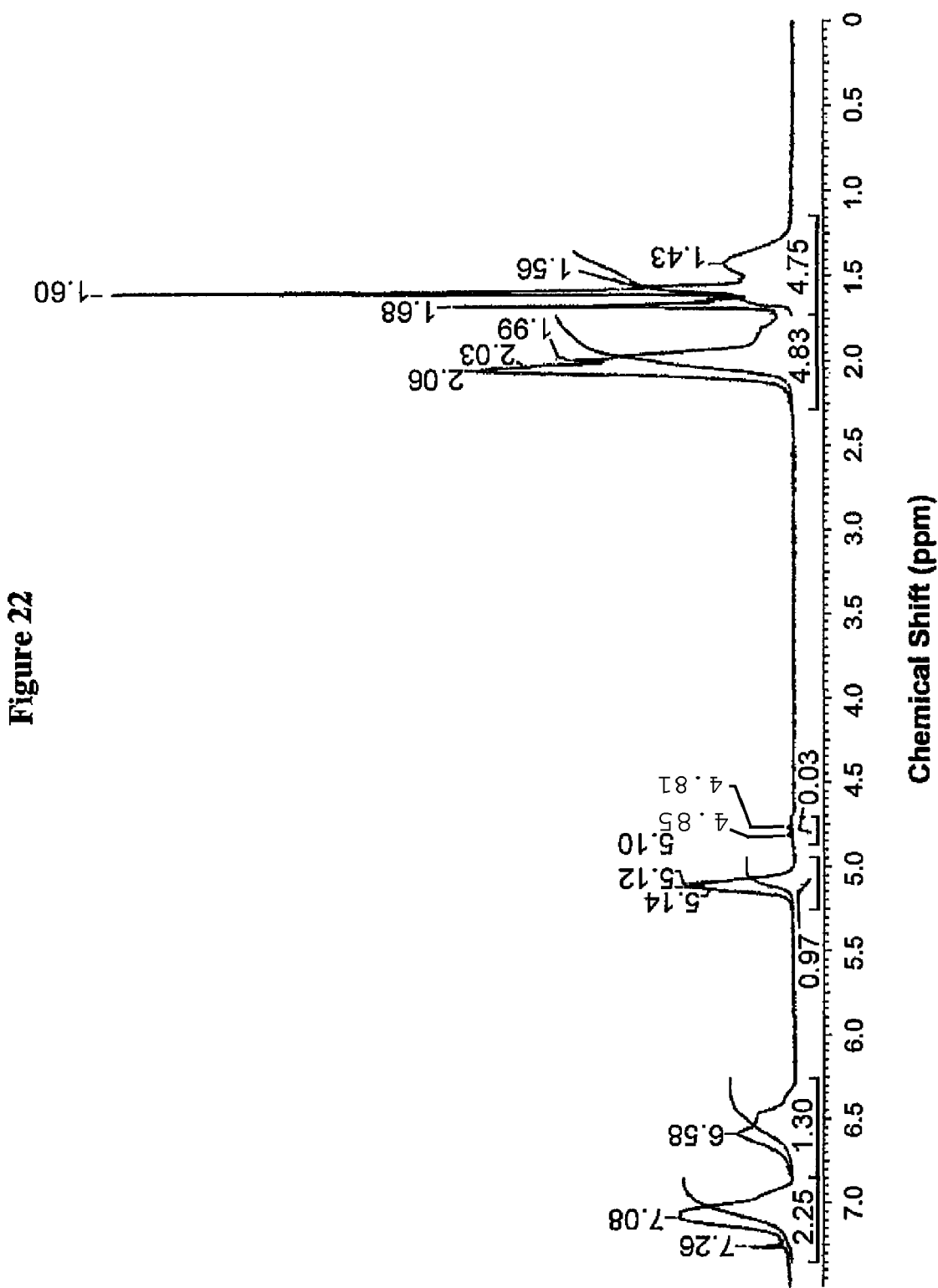
FIG. 22 depicts a $^1H$ NMR spectrum of Example 4.

FIG. 22 shows the $^1$H NMR spectrum of Example 4. Peaks at 4.85 ppm and 4.81 ppm were peaks associated with 3,4-microstructure. Peaks at 5.10 ppm, 5.12 ppm, and 5.14 ppm were peaks associated with 1,4- and 3,4-microstructures. Based on the areas under the peaks of FIG. 22, about 3% of farnesene units in Example 4 was found to have 3,4-microstructure.

Figure 23:
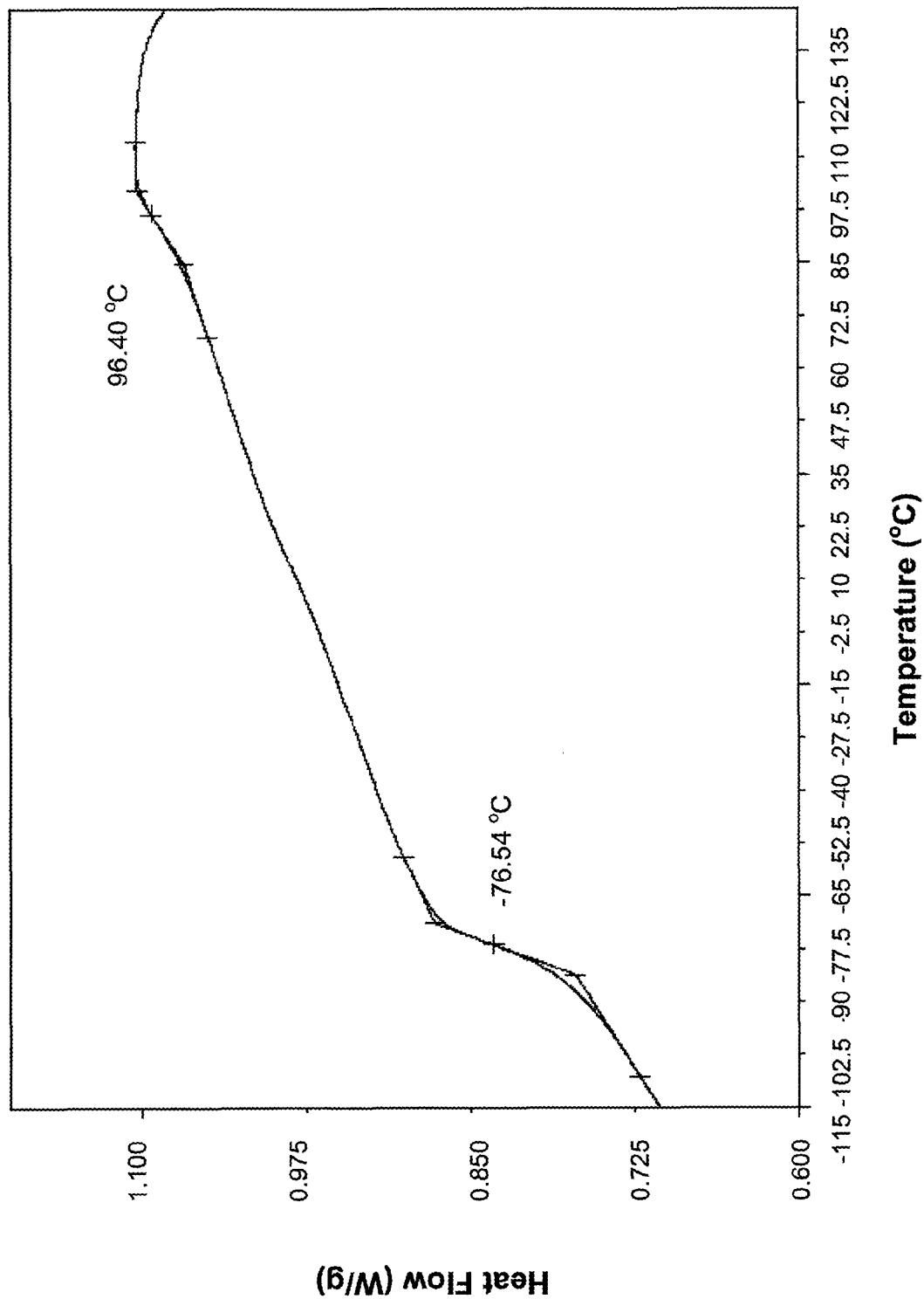
FIG. 23 depicts a DSC curve of Example 4.

The DSC curve of Example 4 is shown in FIG. 23. The thermal characteristics of Example 4 were measured by DSC. The $T_g$ of 1,4-polyfarnesene in Example 4 was found to be about −76° C. The $T_g$ of polystyrene in Example 4 was found to be about 96° C. No other thermal event was detected between −175° C. and 75° C.

Figure 24:
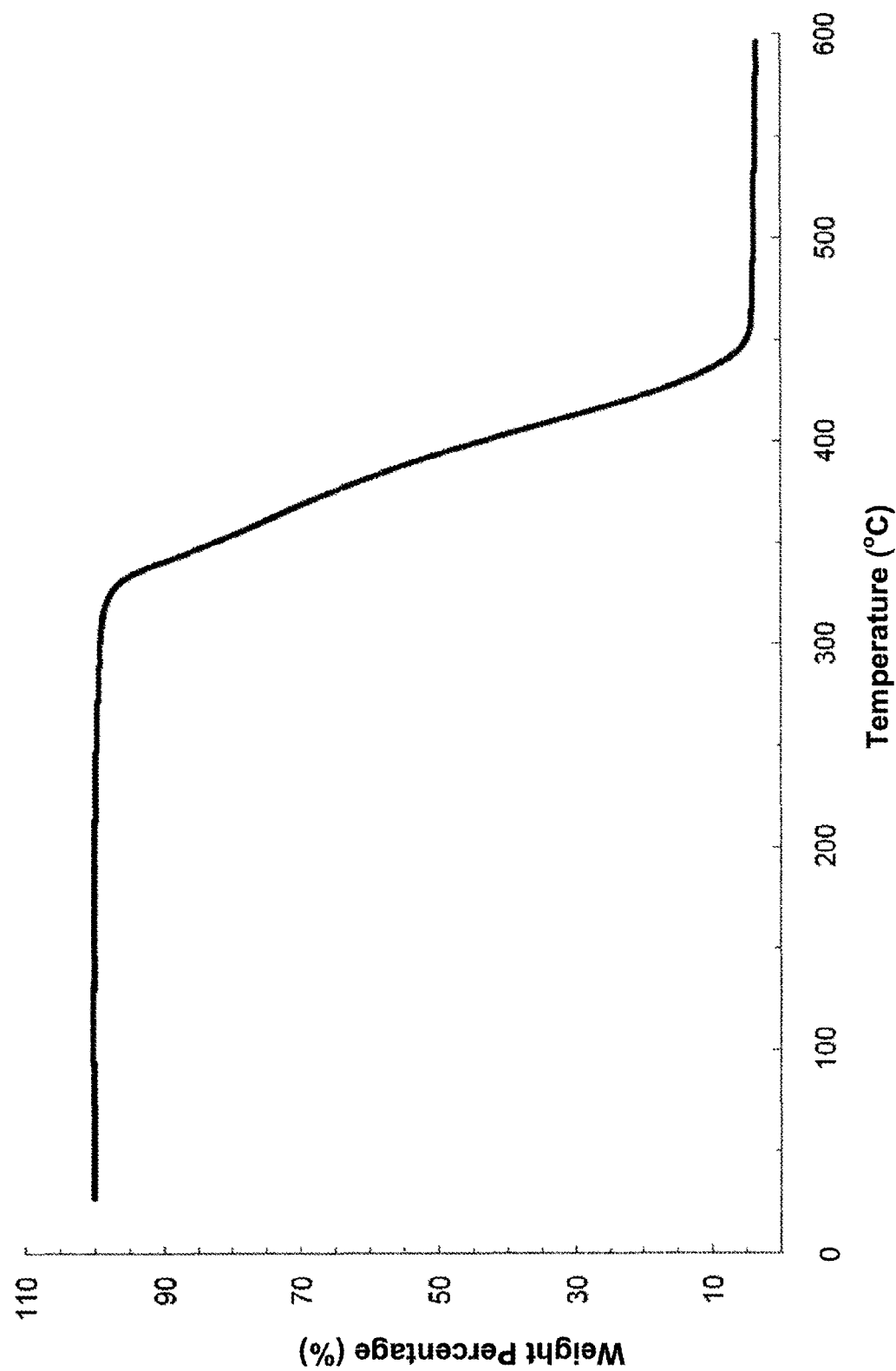
FIG. 24 depicts a TGA curve of Example 4.

The TGA curve of Example 4 measured in air is shown in FIG. 24. The decomposition temperature of Example 4 in air was determined by TGA. The 1% weight loss of Example 4 in air was recorded at 307° C. and the 5% weight loss of Example 4 in air was recorded at 333° C.

Figure 25:
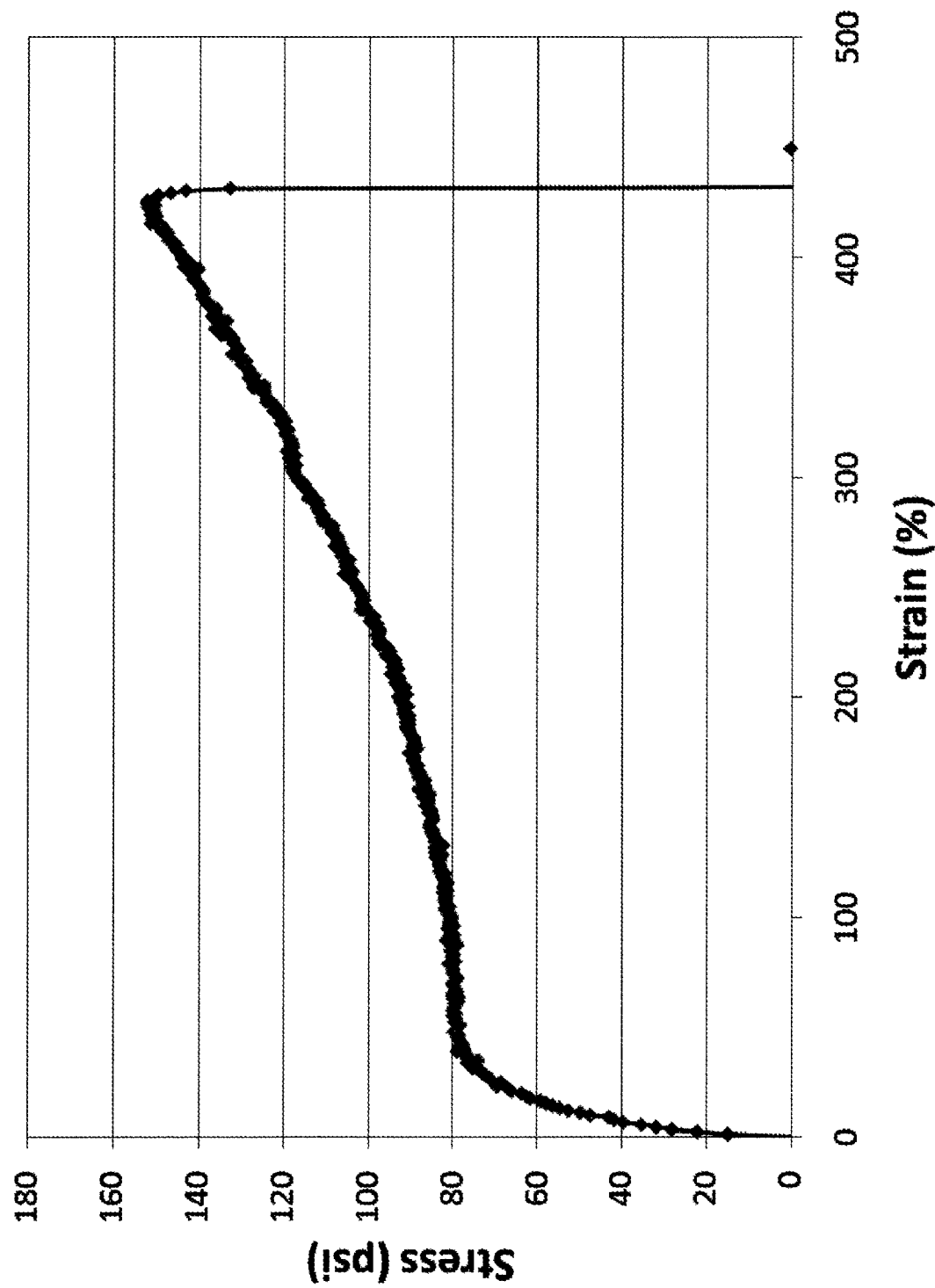
FIG. 25 depicts tensile test results of Example 4.

The tensile test results of Example 4 are shown in FIG. 25. The tensile strength of Example 4 was measured by a tensile test. Example 4 was stiff but yielded. As shown in FIG. 25, the elongation at break of Example 4 was found to be about 425% with a maximum tensile strength of about 152 psi. The modulus of Example 4 was calculated to be about 31.9 kpsi. Stress at 330% elongation of Example 4 was about 122 psi.

Figure 26:
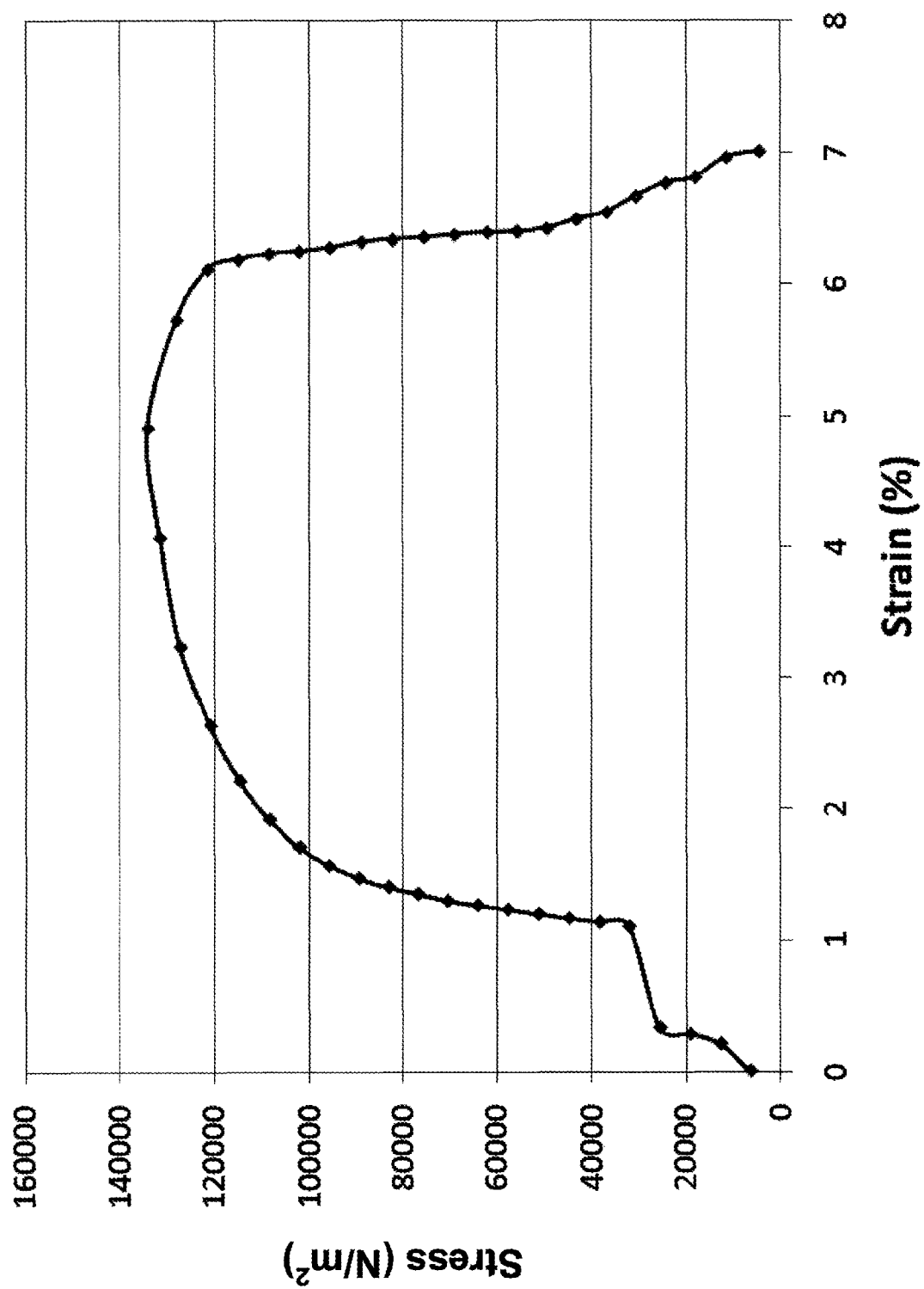
FIG. 26 depicts lap test results of Example 4.

Example 4 was observed to be tacky. The lap test results of Example 4, due to an adhesive failure, are shown in FIG. 26. The adhesive energy of Example 4 was found to be about 2,928,000 J/m$^2$ with a peak stress of about 134,000 N/m$^2$.

Example 5

Polystyrene-3,4-polyfarnesene-polystyrene

To a first dried three neck reactor under argon atmosphere, a pre-dried 12% solution of β-farnesene in cyclohexane was added. To a second dried three neck reactor under argon atmosphere, a pre-dried solution of 10% styrene in cyclohexane was added. Afterwards, 141.1 g of the styrene solution (i.e., 14.82 g of styrene) was transferred to a dried reactor under argon atmosphere. A mixture of n-butyl lithium (5.84× 10$^{-4}$ mol) and TMEDA (5.02×10$^{-4}$ mol) was added into the reactor as an initiator, and the reactor was heated at about 50° C. for about 16 hours, until all styrene was consumed, as monitored by GPC. Then, 143.07 g of β-farnesene solution (i.e., 15.74 g of β-farnesene) was transferred to the reactor under argon atmosphere. The reaction was allowed to react until completion for about 16 hours, as monitored by GPC.

Dichlorosilane coupling agent was then added into the reactor in three equal aliquots, such that the mole ratio of Li to Cl was 1:2. The reaction mixture was allowed react until completion as indicated by a color change from yellow to clear in the reactor. Example 5 was precipitated from the reaction mixture by a 1% solution of t-butyl catachol in ethanol. After drying in a vacuum oven at about 60° C. for about 2 hours, Example 5 was kept under vacuum for about 16 hours. Afterwards, Example 5, collected at 28.75 g (yield 96%), was stored in a refrigerator to prevent any crosslinking before characterization.

Figure 27:
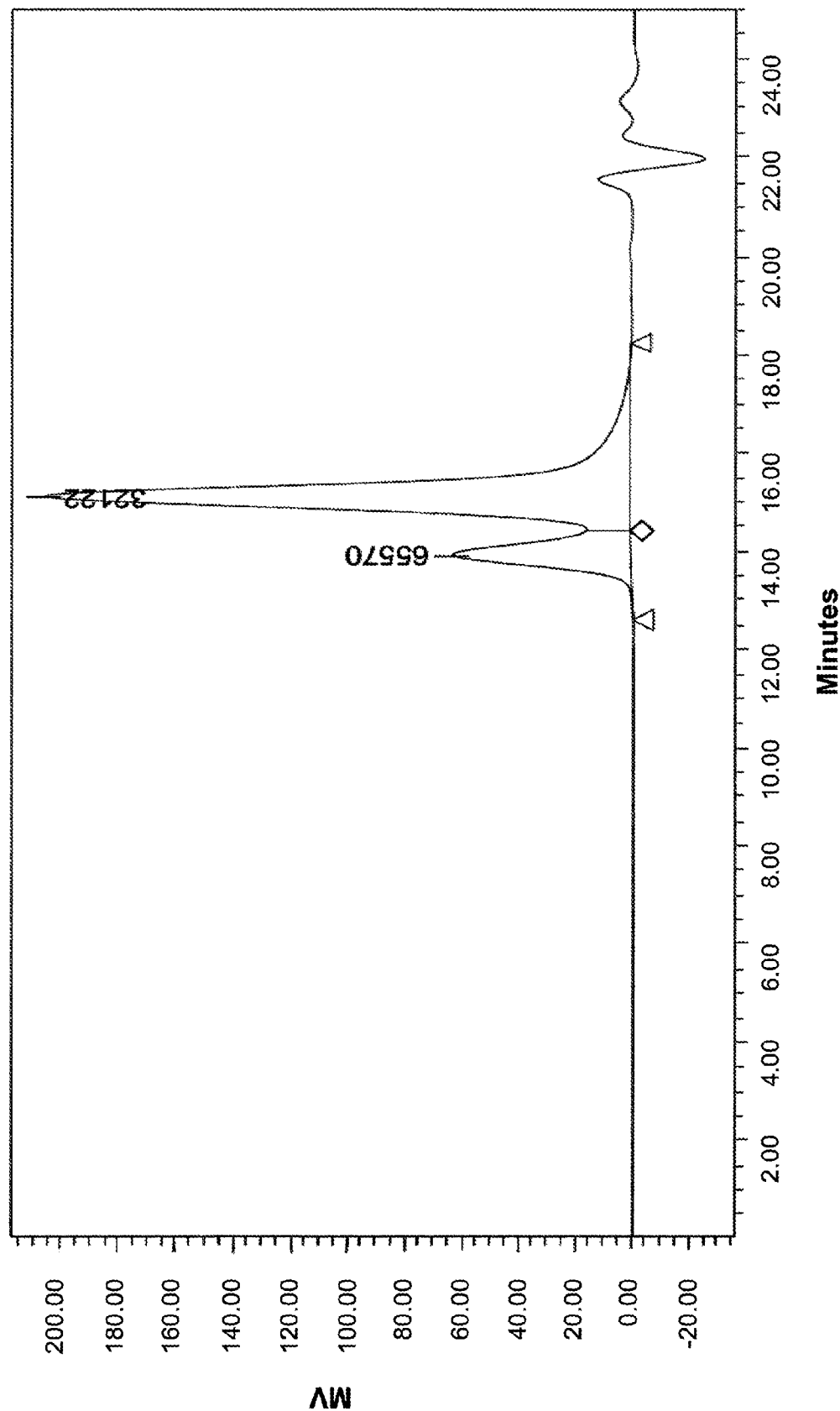
FIG. 27 depicts a GPC curve of polystyrene formed.

The GPC curve of polystyrene is shown in FIG. 27. The progress of synthesizing polystyrene was monitored by GPC. The two peaks in FIG. 27 indicated that there were two distinct weight fractions of polystyrene. The $M_n$, $M_w$, $M_z$, $M_{z+1}$, polydispersity, $M_z/M_w$, and $M_{z+1}/M_w$ of polystyrene are shown in Table 7. The $M_p$ of the first peak in FIG. 27 was found to be about 65,570 g/mol. The $M_p$ of the second peak in FIG. 27 was found to be about 32,122 g/mol.

TABLE 7

| Properties | Polystyrene |
| --- | --- |
| $M_n$ | 27,915 g/mol |
| $M_w$ | 30,898 g/mol |
| $M_z$ | 32,608 g/mol |
| $M_{z+1}$ | 33,819 g/mol |
| Polydispersity | 1.106849 |
| $M_z/M_w$ | 1.055361 |
| $M_{z+1}/M_w$ | 1.094557 |

Figure 28:
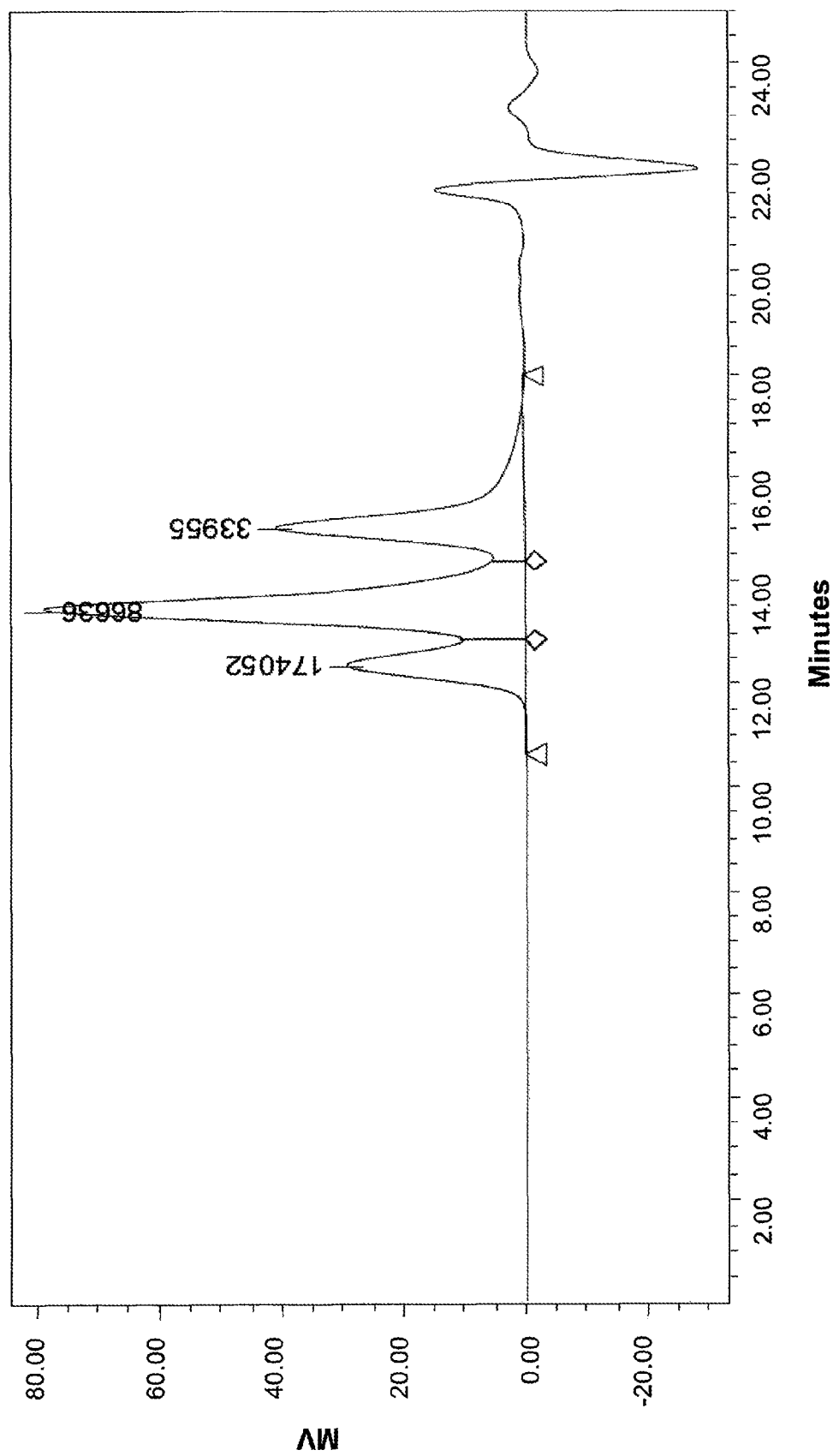
FIG. 28 depicts a GPC curve of polystyrene-3,4-polyfarnesene di-block copolymer formed.

The polystyrene formed then acted as an initiator to initiate the polymerization with β-farnesene to form a polystyrene-3,4-polyfarnesene di-block copolymer. The GPC curve of the di-block copolymer is shown in FIG. 28. The progress of the di-block copolymer synthesis was monitored by GPC. The three peaks in FIG. 28 indicated that there were three distinct weight fractions in the di-block copolymer reaction solution. The $M_n$, $M_w$, $M_z$, $M_{z+1}$, polydispersity, $M_z/M_w$, and $M_{z+1}/M_w$ of the di-block copolymer are shown in Table 8. The $M_p$ of the first peak in FIG. 28, corresponding to polystyrene-3,4-polyfarnesene-polystyrene, was found to be about 174,052 g/mol. The $M_p$ of the second peak in FIG. 28, corresponding to the di-block copolymer, was found to be about 86,636 g/mol. The molecular weight of 3,4-polyfarnesene in the di-block copolymer was calculated to be about 54,000 g/mol. The $M_p$ of the third peak in FIG. 28, corresponding to polystyrene, was found to be about 33,955 g/mol.

TABLE 8

| Properties | Polystyrene-3,4-polyfarnesene Di-block Copolymer |
| --- | --- |
| $M_n$ | 27,801 g/mol |
| $M_w$ | 31,379 g/mol |
| $M_z$ | 33,539 g/mol |
| $M_{z+1}$ | 35,033 g/mol |
| Polydispersity | 1.128697 |
| $M_z/M_w$ | 1.068833 |
| $M_{z+1}/M_w$ | 1.116447 |

Figure 29:
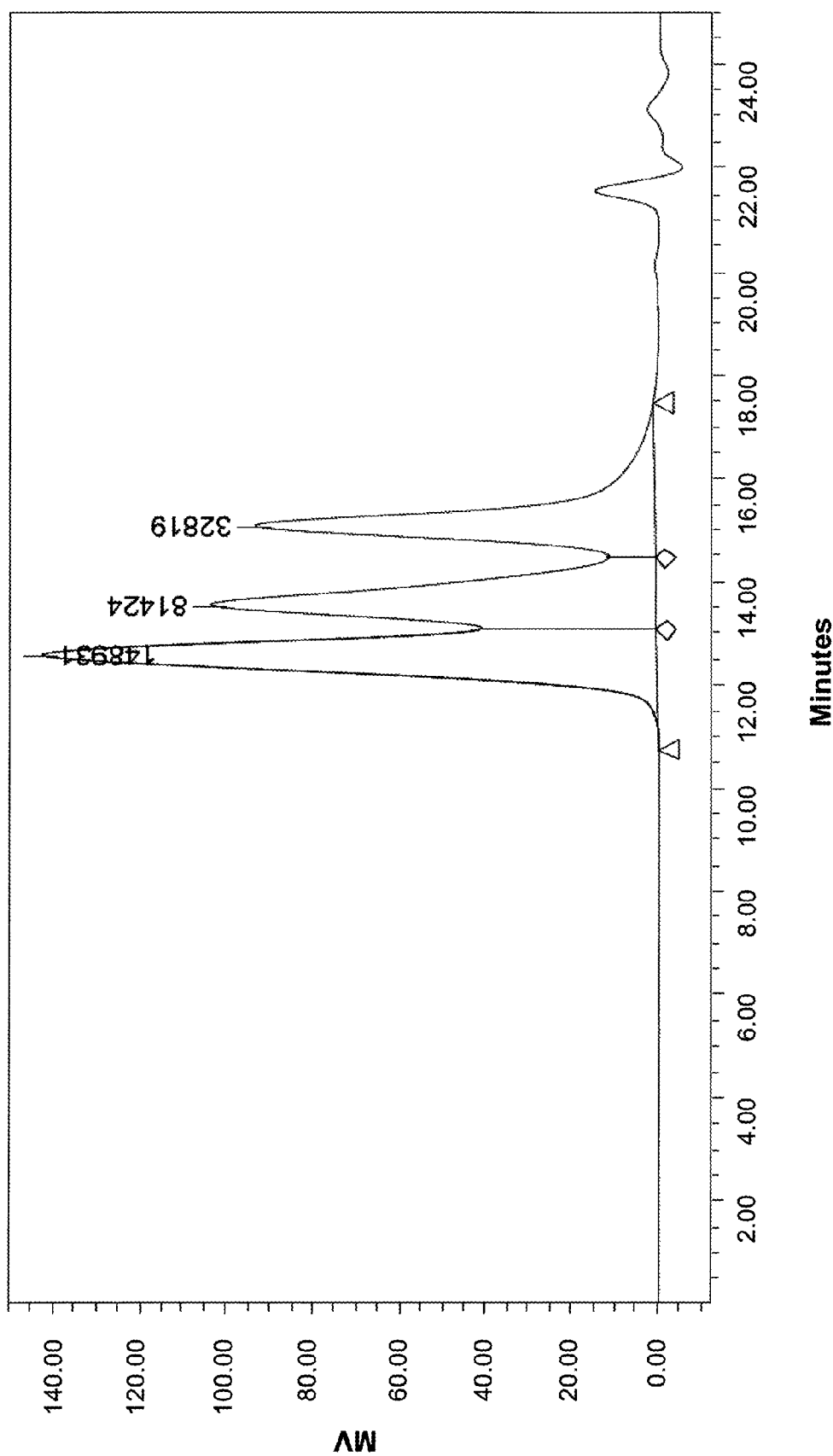
FIG. 29 depicts a GPC curve of Example 5.

The polystyrene-3,4-polyfarnesene di-block copolymer was further coupled to form Example 5. FIG. 29 shows the GPC curve of Example 5. The molecular weight and polydispersity of Example 5 were determined by GPC. The three peaks in FIG. 29 indicated that there were three distinct weight fractions for the coupling product formed. The $M_n$, $M_w$, $M_z$, $M_{z+1}$, polydispersity, $M_z/M_w$, and $M_{z+1}/M_w$ of Example 5 are shown in Table 9. The $M_p$ of the first peak in FIG. 29, corresponding to Example 5, was found to be about 148,931 g/mol. Example 5 was obtained at about 33% of the coupling product. The number of farnesene monomer units in Example 5 was calculated to be about 300. The peak molecular weight of the blocks in Example 5 was found to be about 32,000-108,000-32,000 g/mol. The $M_p$ of the second peak in FIG. 29, corresponding to the polystyrene-3,4-polyfarnesene di-block copolymer, was found to be about 81,424 g/mol. The $M_p$ of the third peak in FIG. 29, corresponding to polystyrene, was found to be about 32,819 g/mol.

TABLE 9

| Properties | Example 4 |
| --- | --- |
| $M_n$ | 28,179 g/mol |
| $M_w$ | 30,815 g/mol |
| $M_z$ | 32,590 g/mol |
| $M_{z+1}$ | 33,905 g/mol |
| Polydispersity | 1.093554 |
| $M_z/M_w$ | 1.057606 |
| $M_{z+1}/M_w$ | 1.100250 |

Figure 30:
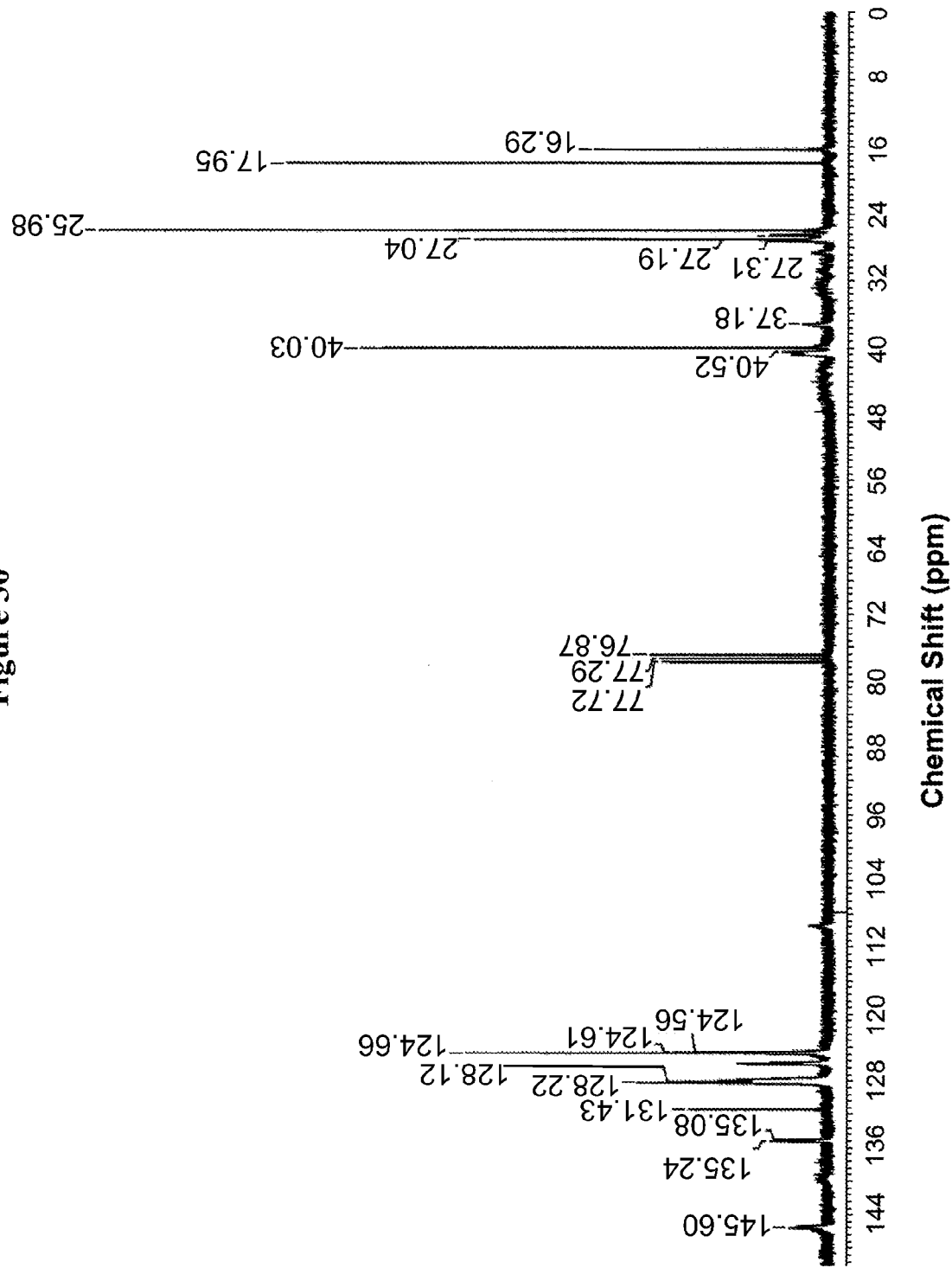
FIG. 30 depicts a $^{13}C$ NMR spectrum of Example 5.

FIG. 30 shows the $^{13}$C NMR spectrum of Example 5. Peaks at 77.72 ppm, 77.29 ppm, and 76.87 ppm were peaks of associated with the deuterated chloroform used for collecting the $^{13}$C NMR spectrum. Other peaks in FIG. 30 were peaks associated with 3,4-polyfarnesene and polystyrene. The characteristic peak identifying 1,4-polyfarnesene at 139.05 ppm was absent in FIG. 30, indicating a regular microstructure of Example 5.

Figure 31:
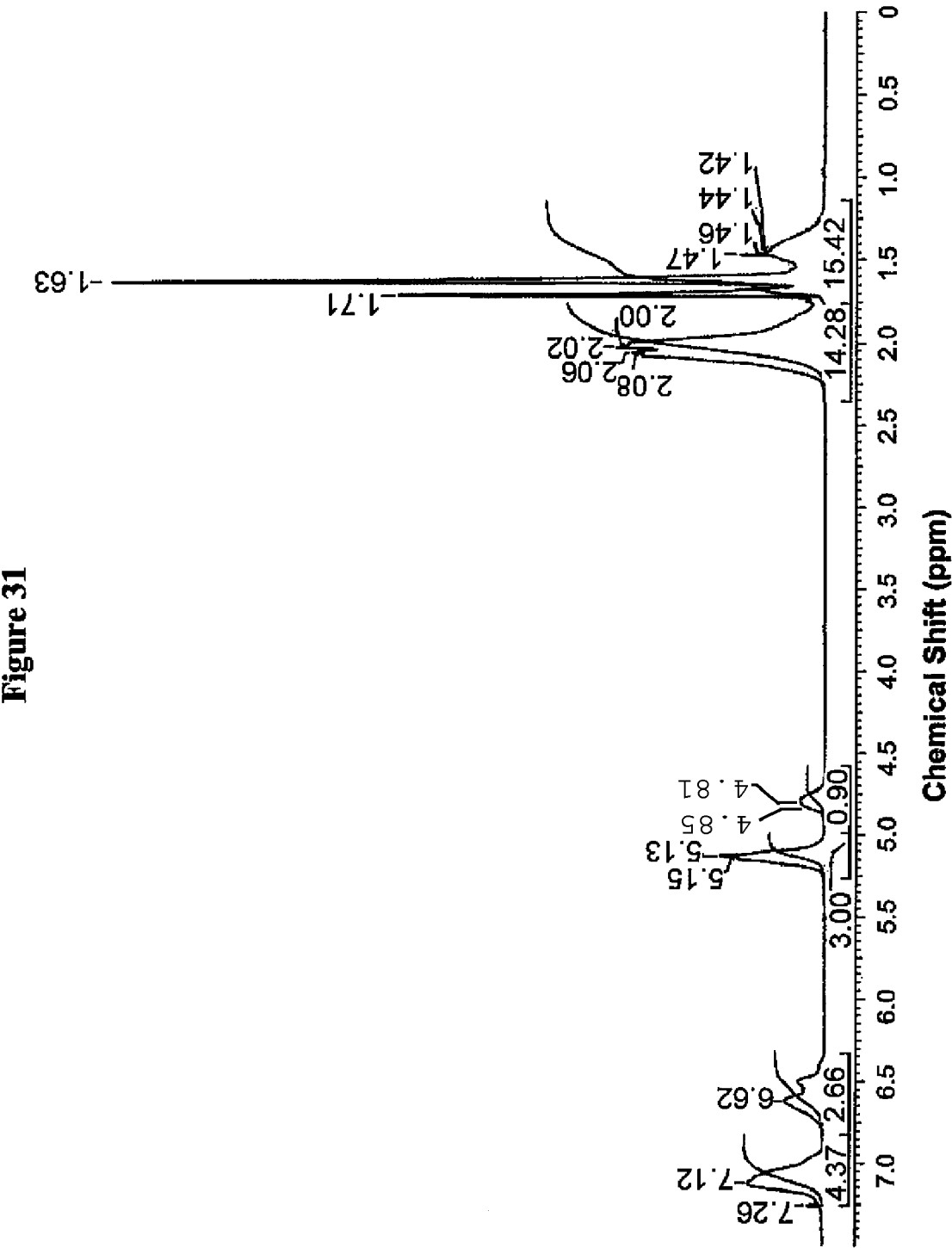
FIG. 31 depicts a $^1H$ NMR spectrum of Example 5.

FIG. 31 shows the $^1$H NMR spectrum of Example 5. Peaks at 4.85 ppm and 4.81 ppm were peaks associated with 3,4-microstructure. Peaks at 5.15 ppm and 5.13 ppm were peaks associated with 1,4- and 3,4-microstructures. Based on the areas under the peaks of FIG. 31, about 5% of farnesene units in Example 5 was found to have 1,4-microstructure.

Figure 32:
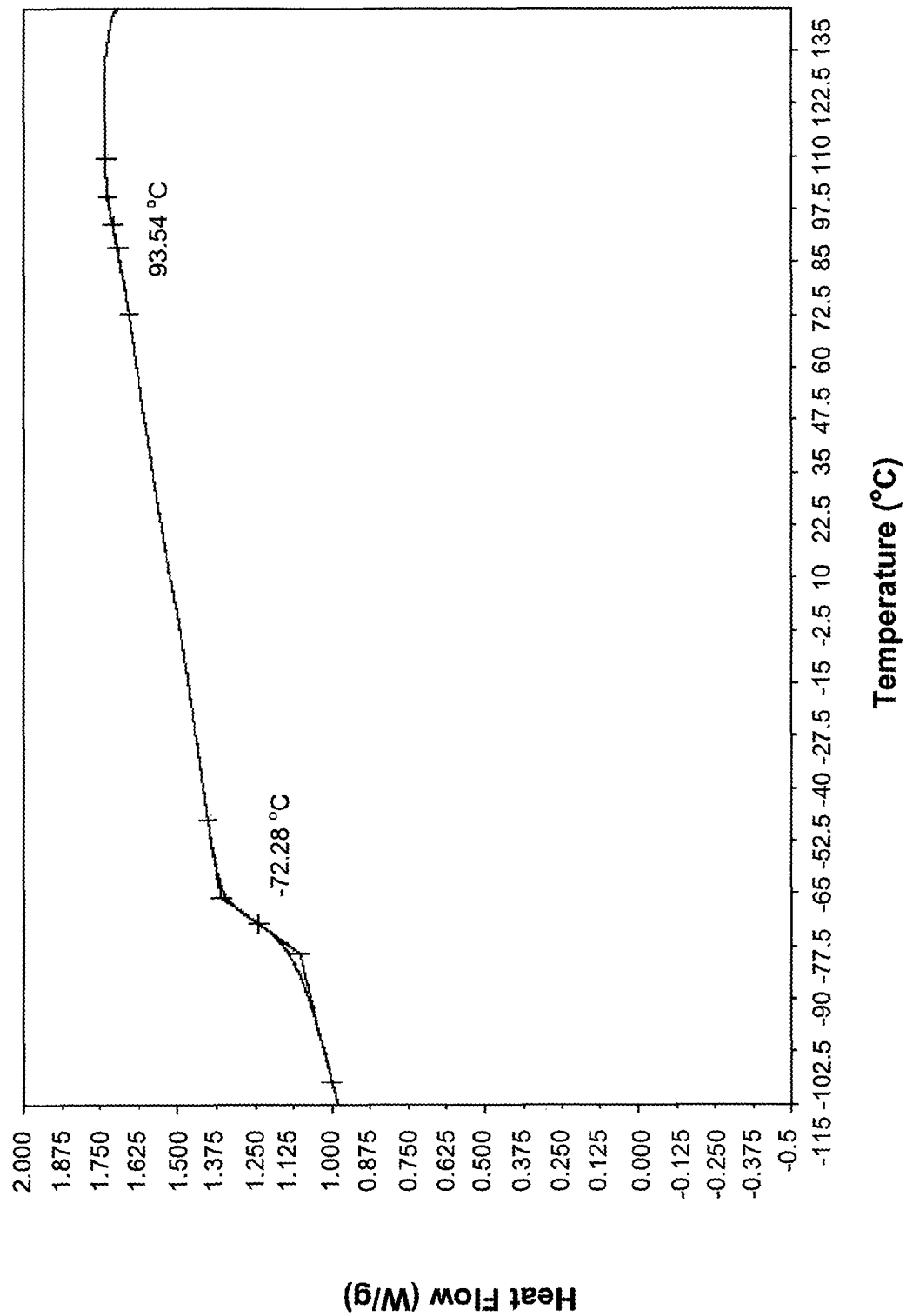
FIG. 32 depicts a DSC curve of Example 5.

The DSC curve of Example 5 is shown in FIG. 32. The thermal characteristics of Example 5 were measured by DSC. The $T_g$ of 3,4-polyfarnesene in Example 5 was found to be about −72° C. The $T_g$ of polystyrene in Example 5 was found to be about 94° C. No other thermal event was detected between −175° C. and 75° C.

Figure 33:
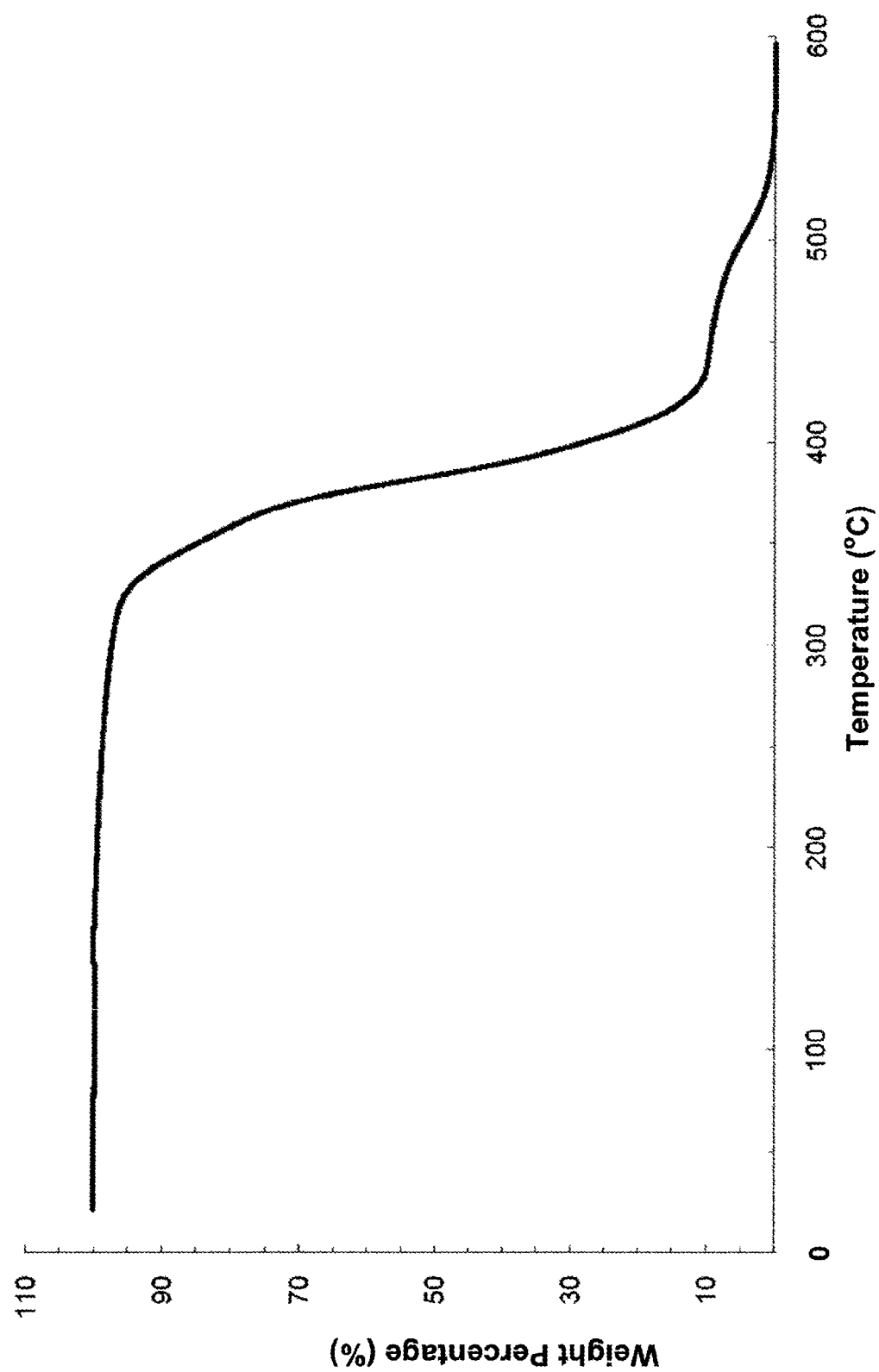
FIG. 33 depicts a TGA curve of Example 5.

The TGA curve of Example 5 measured in air is shown in FIG. 33. The decomposition temperature of Example 5 in air was determined by TGA. The 1% weight loss of Example 5 in air was recorded at 240° C. and the 5% weight loss of Example 5 in air was recorded at 327° C.

Figure 34:
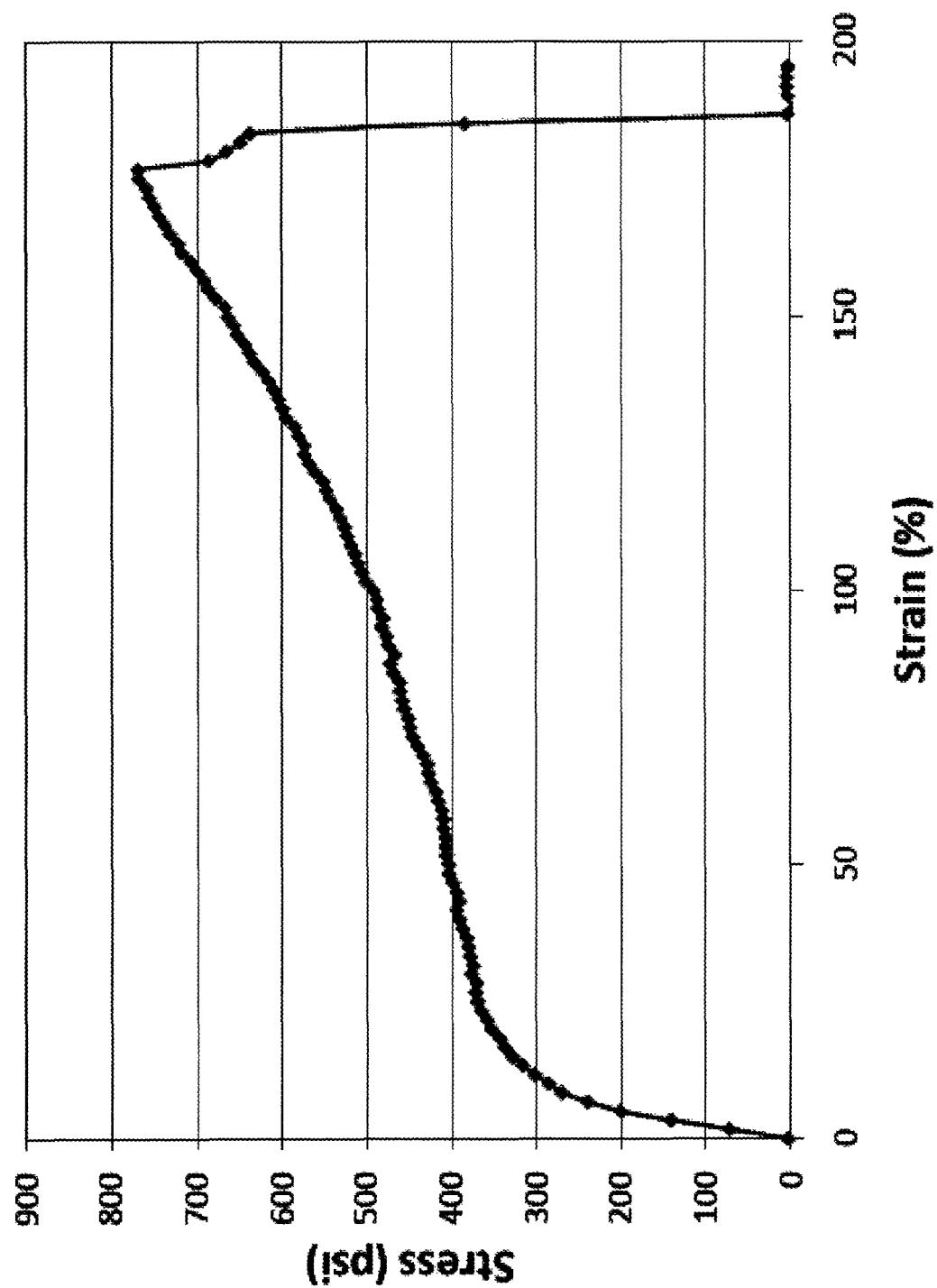
FIG. 34 depicts tensile test results of Example 5.

The tensile test results of Example 5 are shown in FIG. 34. The tensile strength of Example 5 was measured by a tensile test. Example 5 was stiff but yielded. As shown in FIG. 34, the elongation at break of Example 5 was found to be about 175% with a maximum tensile strength of about 768 psi. The modulus of Example 5 was calculated to be about 39.5 kpsi.

Figure 35:
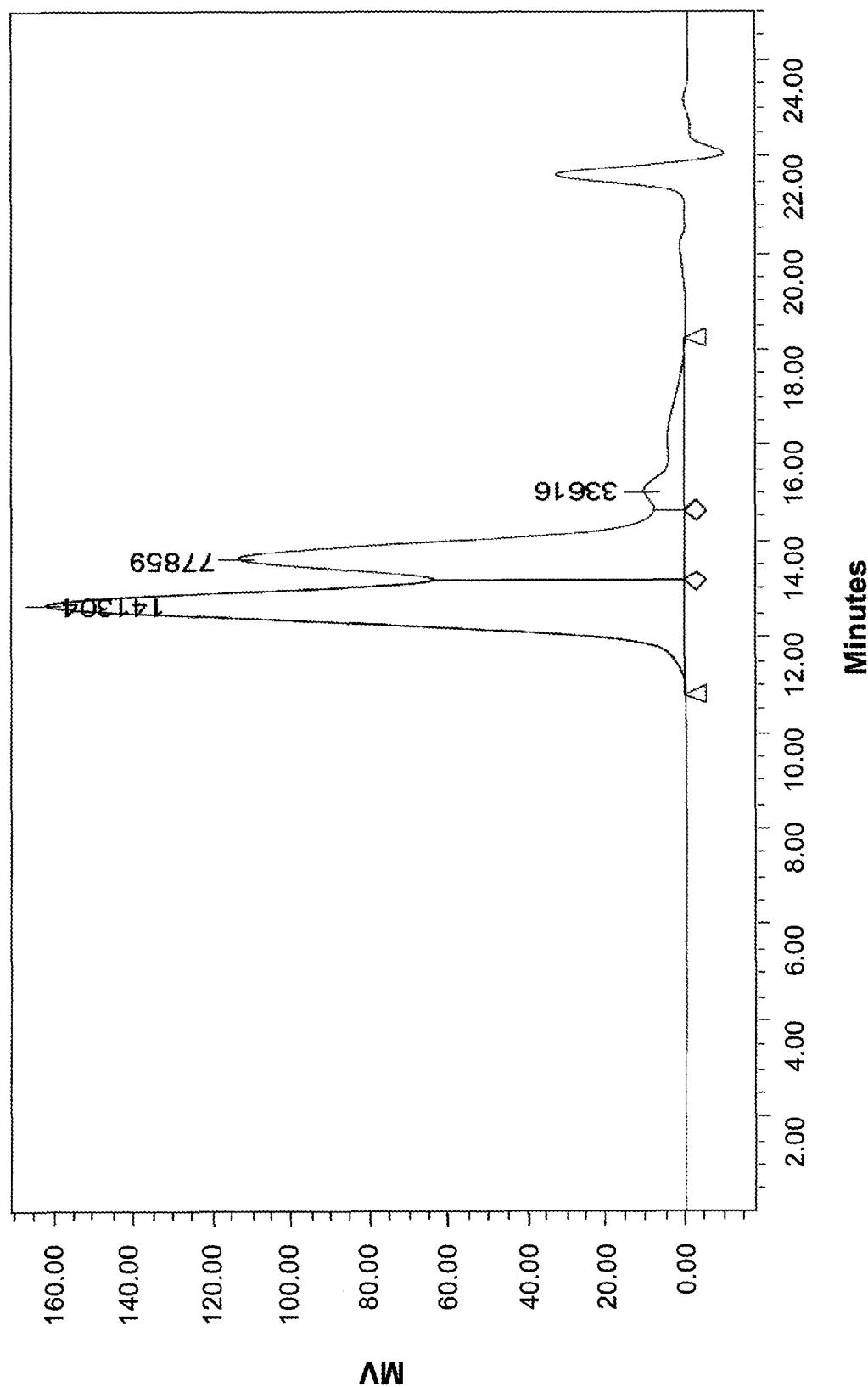
FIG. 35 depicts a GPC curve of Example 5 after extraction with hexane.

Example 5 was further purified by repeated extraction with solvent hexane 4 times. The GPC curve of the purified Example 5 is shown in FIG. 35. The extraction of Example 5 from the coupling product was evaluated by GPC. After the extraction, Example 5, shown as the first peak in FIG. 35, was increased to about 60% of the extracted product. The polystyrene-3,4-polyfarnesene di-block copolymer, shown as the second peak in FIG. 35, was reduced to about 30% of the extracted product. Polystyrene, shown as the third peak in FIG. 35, was reduced to about 10% of the extracted product.

Figure 36:
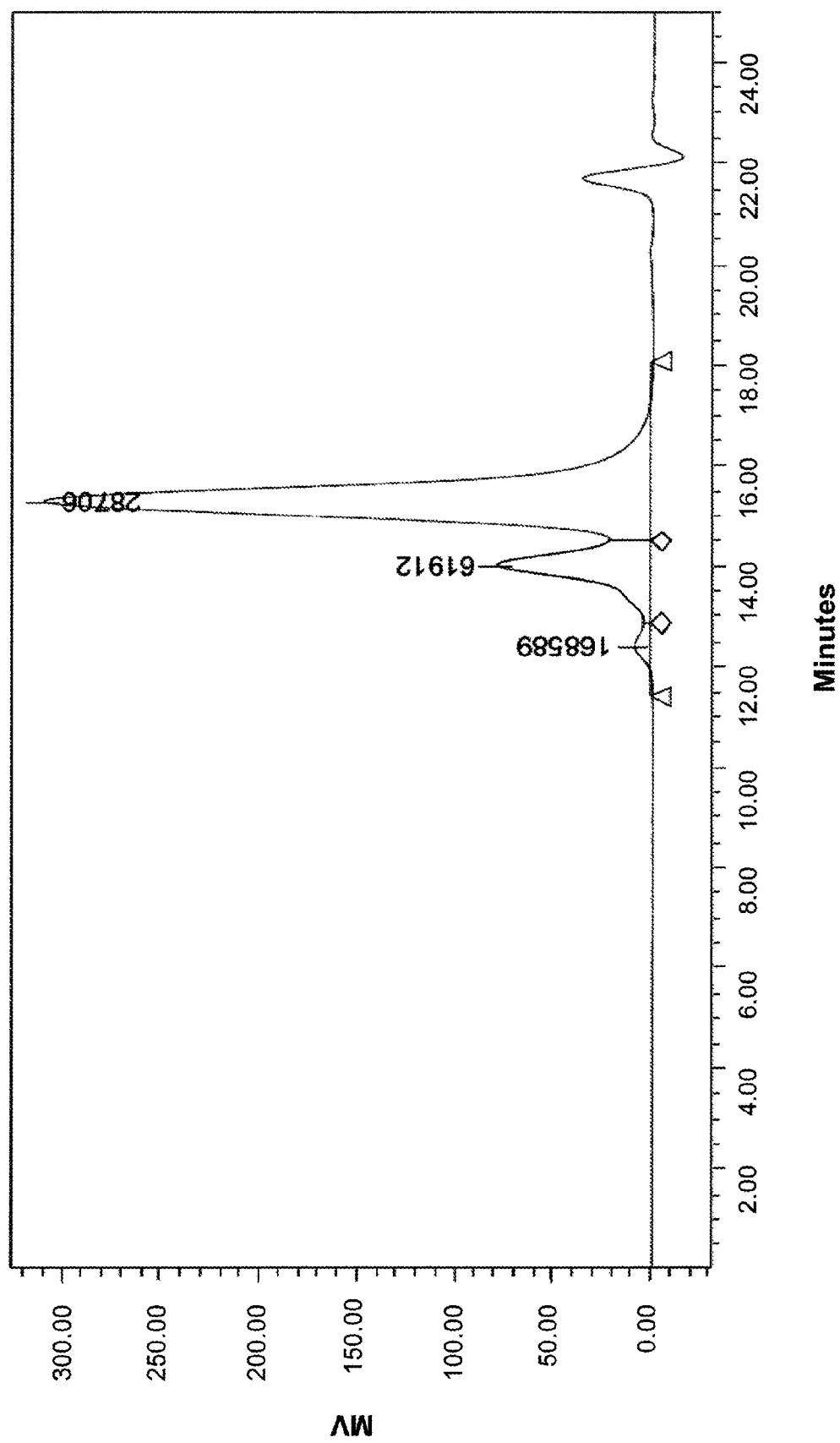
FIG. 36 depicts a GPC curve of hexane after extraction for Example 5.

The GPC curve of the extraction solvent hexane is shown in FIG. 36. After the extraction, Example 5 existed in very low amount in the extraction solvent, shown as the first peak in FIG. 36. A significant amount of the polystyrene-3,4-polyfarnesene di-block copolymer was extracted to the extraction solvent, shown as the second peak in FIG. 36. A majority of polystyrene was extracted to the extraction solvent, shown as the third peak in FIG. 36.

Figure 37:
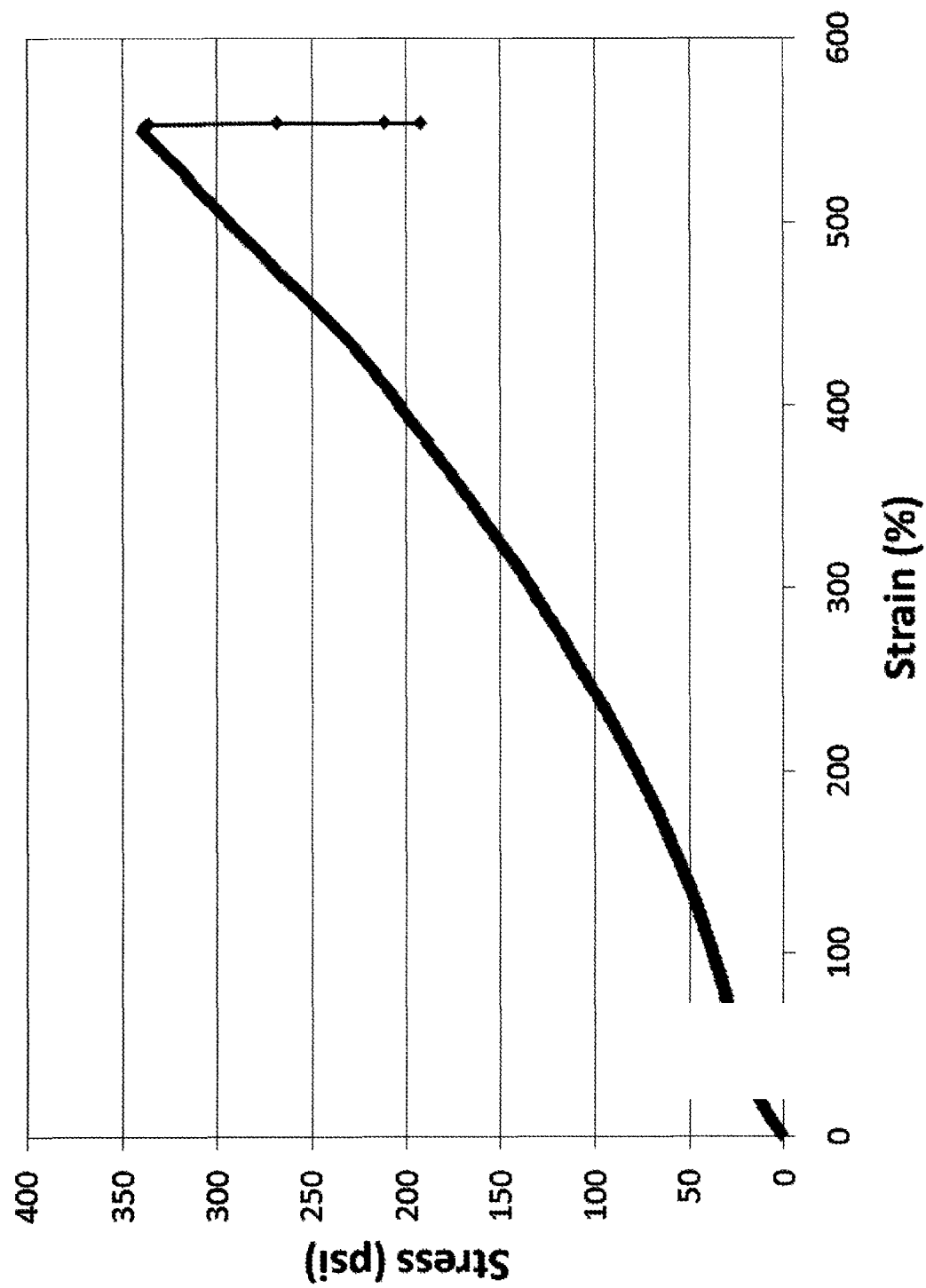
FIG. 37 depicts tensile test results of Example 5.

The tensile test results of the purified Example 5 are shown in FIG. 37. The tensile strength of the purified Example 5 was measured by a tensile test. Example 5 was soft and readily yielded. As shown in FIG. 37, the elongation at break of the purified Example 5 was found to be about 550% with a maximum tensile strength of about 340 psi. The modulus of the purified Example 5 was calculated to be about 65.9 kpsi. Stress at 300% elongation of the purified Example 5 was found to be about 13357.1 psi.

Figure 38:
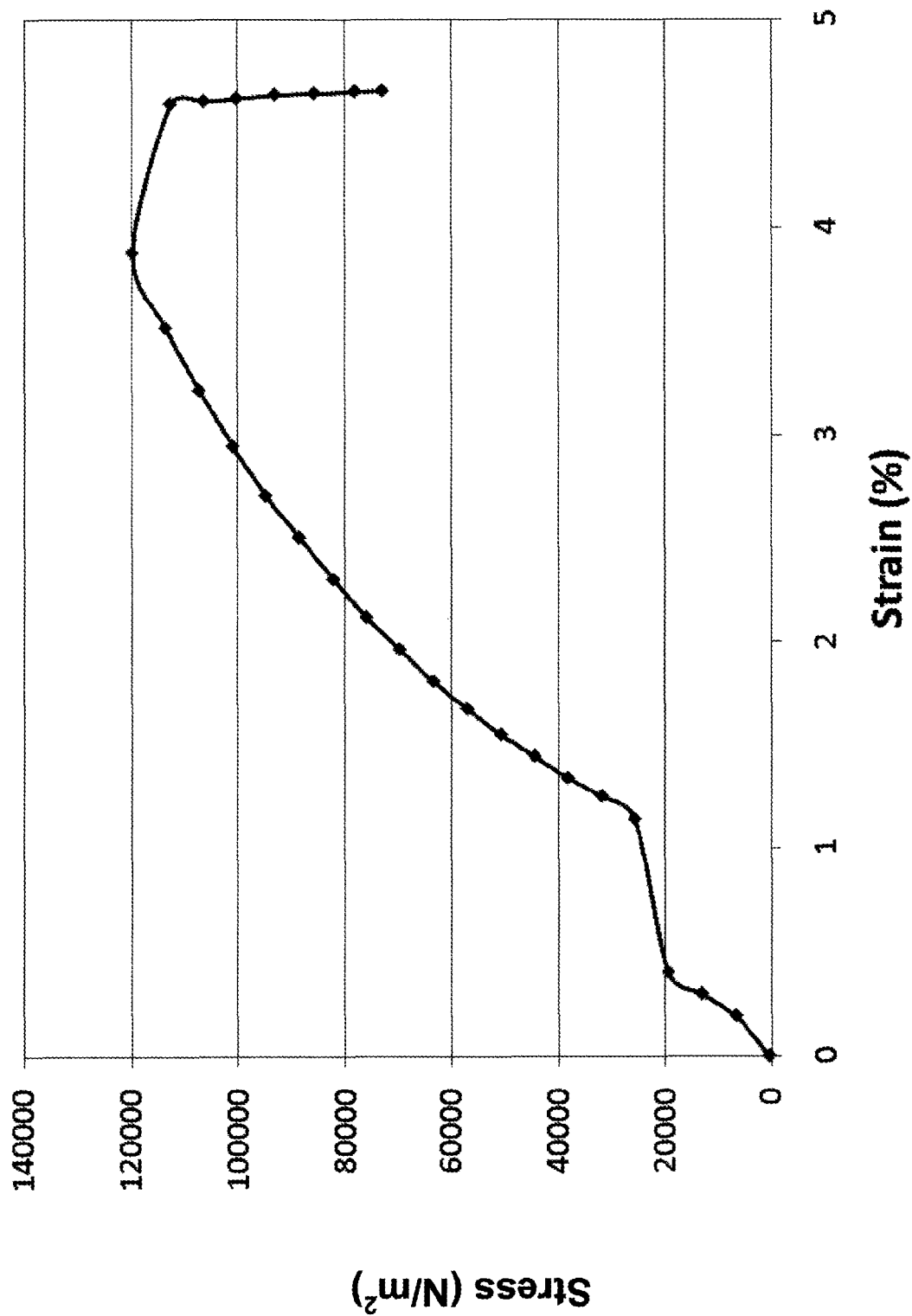
FIG. 38 depicts lap test results of Example 5.

The purified Example 5 was observed to be highly tacky. The lap test results of the purified Example 5, due to an adhesive failure, are shown in FIG. 38. The adhesive capability of the purified Example 5 was measured by a lap test. The adhesive energy of the purified Example 5 was found to be about 1,787,000 $J/m^2$ with a peak stress of about 120,000 $N/m^2$.

Example 6

Example 6 was formed by the vulcanization of Example 1. To formulate the reaction mixture, 62.7 g of Example 1 was mixed with 3.20 g zinc oxide, 1.25 g stearic acid, 0.94 g Rubbermakers Sulfur MC-98, 0.13 g Accelerator TMTD (tetramethylthiuram disulfide), and 0.63 g Accelerator OBTS (N-oxydiethylene-2-benzothiazole sulfenamide). Zinc oxide, stearic acid, Rubbermakers Sulfur MC-98, Accelerator TMTD, and Accelerator OBTS were obtained from Akrochem Corporation, Akron, Ohio. The mixture was then placed in a vulcanization mold and degassed at about 140° C. for about 30 minutes. After degassing, the mixture was cured at about 170° C. for about 15 minutes. After de-molding, Example 6, an elastic solid, was collected at 70.4 g (yield 81%).

Figure 39:
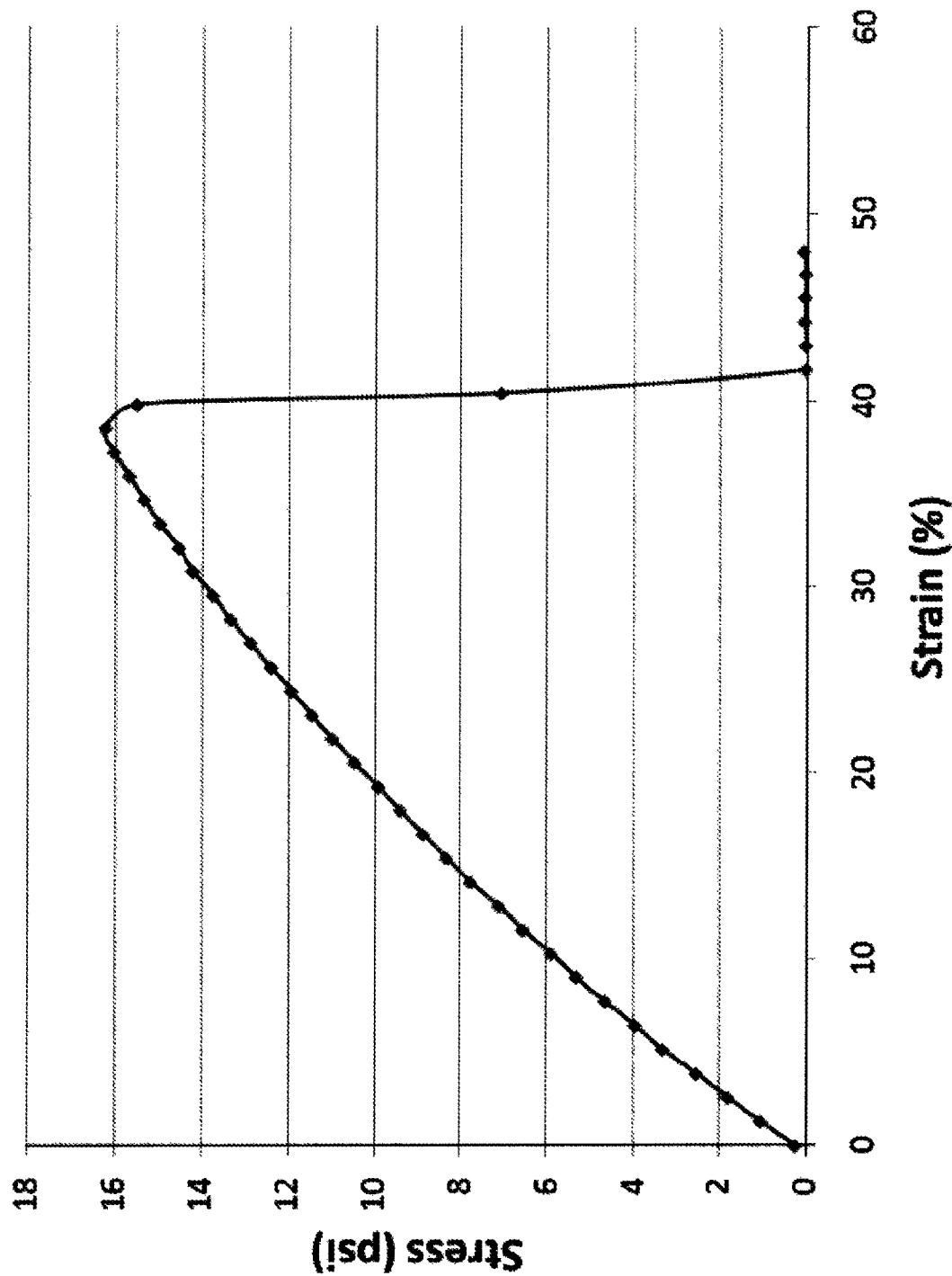
FIG. 39 depicts tensile test results of Example 6.

The tensile test results of Example 6 are shown in FIG. 39. The tensile strength of Example 6 was measured by a tensile test. As shown in FIG. 39, the elongation at break of Example 6 was about 38% with a maximum tensile strength of about 16 psi. The modulus of Example 6 was calculated to be about 58 psi.

Example 7

Example 7 was formed by the vulcanization of Example 2. Example 7 was synthesized similarly according to the procedure for Example 6 except that Example 1 was replaced by 60.3 g Example 2. The net weight of Example 7 was found to be 68.1 g (yield 78%).

Figure 40:
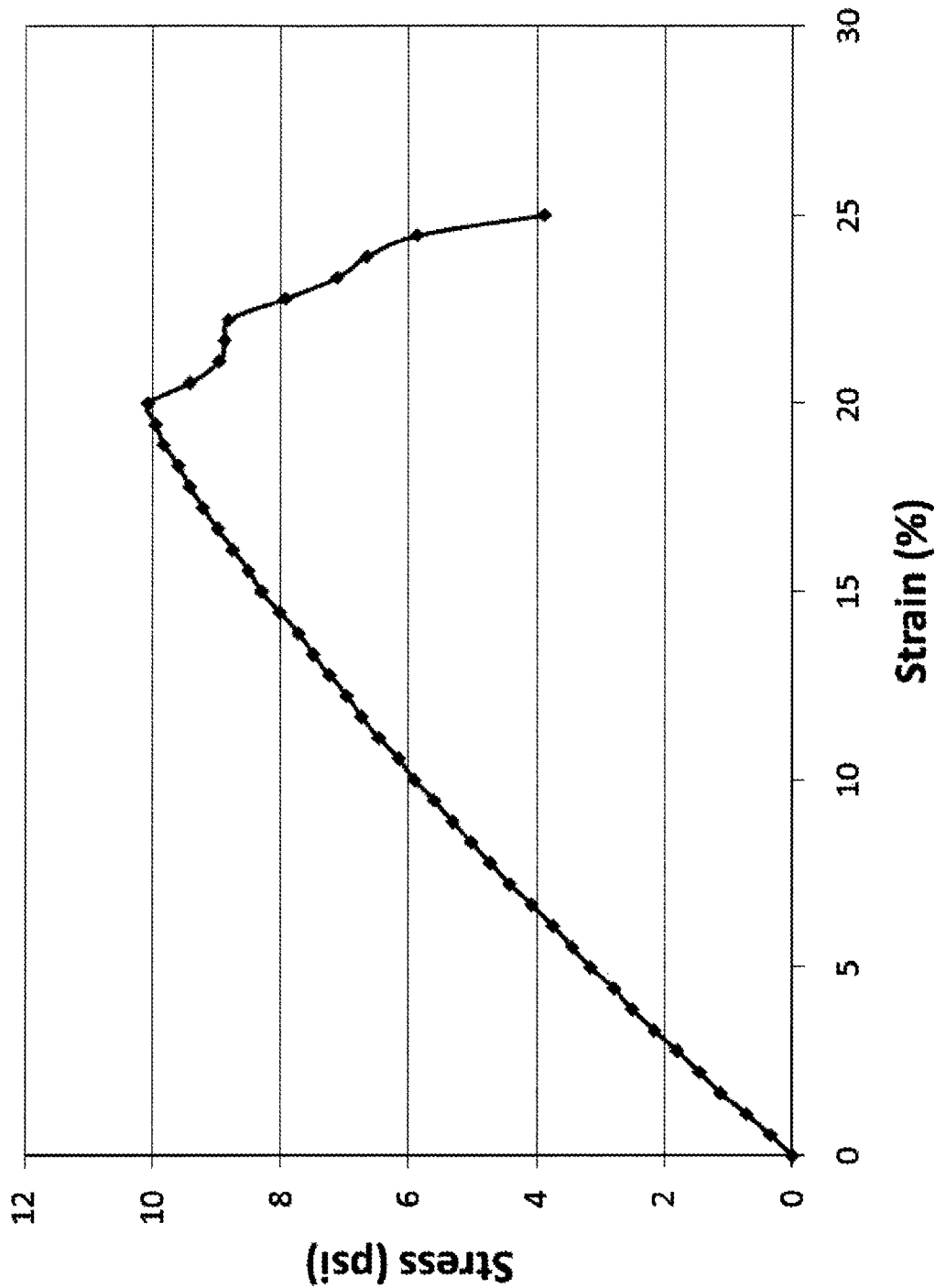
FIG. 40 depicts tensile test results of Example 7.

The tensile test results of Example 7 are shown in FIG. 40. The tensile strength of Example 7 was measured by a tensile test. As shown in FIG. 40, the elongation at break of Example 7 was found to be about 25% with a maximum tensile strength of about 10 psi. The modulus of Example 7 was calculated to be about 66 psi.

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. Finally, any number disclosed herein should be construed to mean approximate, regardless of whether the word "about" or "approximately" is used in describing the number. The appended claims intend to cover all those modifications and variations as falling within the scope of the invention.

What is claimed is:

1. A farnesene interpolymer comprising one or more polymer molecules having formula (X'):

wherein each of n and m is independently an integer from 1 to about 100,000; X has one or more of formulae (I')-(VIII'):

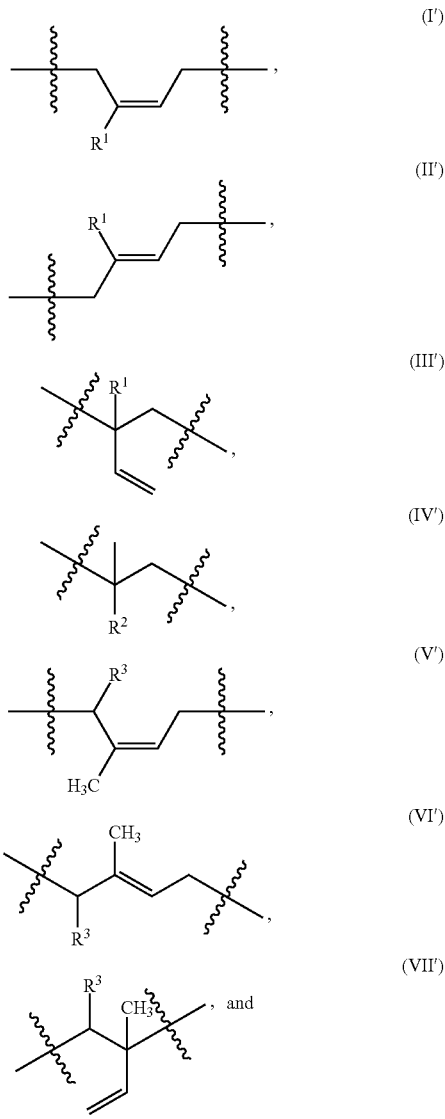

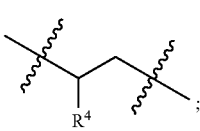

Y has formula (IX'):

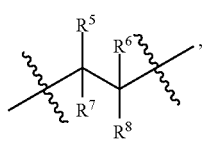

wherein R¹ has formula (XI):

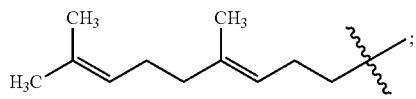

R² has formula (XII):

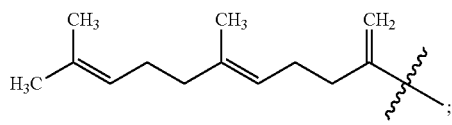

R³ has formula (XIII):

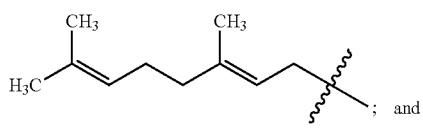

and
R⁴ has formula (XIV):

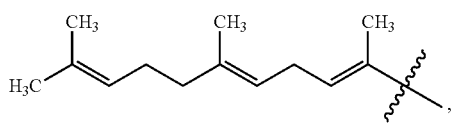

wherein each of $R^5$, $R^6$, $R^7$ and $R^8$ is independently H, alkyl, cycloalkyl, aryl, cycloalkenyl, alkynyl, heterocyclyl, alkoxy, aryloxy, carboxy, alkoxycarbonyl, aminocarbonyl, alkylaminocarbonyl, dialkylaminocarbonyl, acyloxy, nitrile or halo, and wherein a mole percent ratio of X to Y is from about 1:4 to about 100:1.

2. The farnesene interpolymer of claim 1, wherein one of $R^5$, $R^6$, $R^7$ and $R^8$ is aryl; and each of the other three of $R^5$, $R^6$, $R^7$ and $R^8$ is H.

3. The farnesene interpolymer of claim 2, wherein the aryl is phenyl.

4. The farnesene interpolymer of claim 3, wherein the farnesene interpolymer is a block farnesene interpolymer.

5. The farnesene interpolymer of claim 4, wherein the block farnesene interpolymer according to formula X' comprises one block of one or more X and two blocks each of one or more Y and wherein the one block of one or more X is between the two blocks each of one or more Y.

6. The farnesene interpolymer of claim 1, wherein at least one of $R^5$, $R^6$, $R^7$ and $R^8$ is alkoxy, aryloxy, carboxy, alkoxycarbonyl, aminocarbonyl, alkylaminocarbonyl, dialkylaminocarbonyl, acyloxy, nitrile, or halo.

7. The farnesene interpolymer of claim 1, wherein formula (I') is in an amount of at most about 80 wt. %, based on a total weight of the farnesene interpolymer.

8. The farnesene interpolymer of claim 1, wherein formula (II') is in an amount from about 15 wt. % to about 99 wt. %, based on a total weight of the farnesene interpolymer.

9. A method of making the farnesene interpolymer according to claim 1 comprising copolymerizing a farnesene and at least one vinyl monomer in the presence of a catalyst, wherein a mole percent ratio of the farnesene to the at least one vinyl monomer is from about 1:4 to about 100:1, and wherein the vinyl monomer does not comprise an isoprene.

10. The method of claim 9, wherein the farnesene is α-farnesene, β-farnesene or a combination thereof.

11. The method of claim 9, wherein the at least one vinyl monomer is ethylene, an α-olefin, a substituted or unsubstituted vinyl halide, vinyl ether, acrylonitrile, acrylic ester, methacrylic ester, acrylamide or methacrylamide or a combination thereof.

12. The method of claim 9, wherein the at least one vinyl monomer is styrene.

13. The method of claim 9, wherein the farnesene is prepared by a microorganism.

14. The method of claim 9, wherein the farnesene is derived from a simple sugar.

15. A farnesene interpolymer prepared by the method of claim 9.

16. A method of making the farnesene interpolymer according to claim 1 comprising:
 (a) making a farnesene from a simple sugar by a microorganism; and
 (b) copolymerizing the farnesene and at least one vinyl monomer in the presence of a catalyst.

17. The method of claim 16, wherein a mole percent ratio of the farnesene to the vinyl monomer is from about 1:4 to about 100:1.

18. The method of claim 16, wherein the at least one vinyl monomer is ethylene, an α-olefin, or a substituted or unsubstituted vinyl halide, vinyl ether, acrylonitrile, acrylic ester, methacrylic ester, acrylamide or methacrylamide, or a combination thereof.

19. The method of claim 16, wherein the at least one vinyl monomer is styrene.

20. A farnesene interpolymer prepared by the method of claim 16.

* * * * *